US012728162B2

(12) United States Patent
Lopez-Chavez et al.

(10) Patent No.: US 12,728,162 B2
(45) Date of Patent: Sep. 8, 2026

(54) METHODS OF TREATING LUNG CANCER WITH A PD-1 AXIS BINDING ANTAGONIST, A PLATINUM AGENT, AND A TOPOISOMERASE II INHIBITOR

(71) Applicant: Genentech, Inc., South San Francisco, CA (US)

(72) Inventors: Ariel Lopez-Chavez, South San Francisco, CA (US); Daniel Antonius Waterkamp, Riehen (CH)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 18/364,431

(22) Filed: Aug. 2, 2023

(65) Prior Publication Data

US 2024/0261399 A1 Aug. 8, 2024

Related U.S. Application Data

(63) Continuation of application No. 16/449,105, filed on Jun. 21, 2019, now abandoned.

(60) Provisional application No. 62/736,326, filed on Sep. 25, 2018, provisional application No. 62/719,461, filed on Aug. 17, 2018, provisional application No. 62/689,105, filed on Jun. 23, 2018.

(51) Int. Cl.

| | |
|---|---|
| ***A61K 39/395*** | (2006.01) |
| ***A61K 9/00*** | (2006.01) |
| ***A61K 31/365*** | (2006.01) |
| ***A61K 33/243*** | (2019.01) |
| ***A61P 35/00*** | (2006.01) |
| *A61K 39/00* | (2006.01) |

(52) U.S. Cl.

CPC ........ *A61K 39/3955* (2013.01); *A61K 9/0019* (2013.01); *A61K 31/365* (2013.01); *A61K 33/243* (2019.01); *A61P 35/00* (2018.01); *A61K 2039/505* (2013.01)

(58) Field of Classification Search

None

See application file for complete search history.

(56) References Cited

U.S. PATENT DOCUMENTS

| | | | |
|---|---|---|---|
| 4,016,043 | A | 4/1977 | Schuurs |
| 4,018,653 | A | 4/1977 | Mennen |
| 4,275,149 | A | 6/1981 | Litman |
| 4,318,980 | A | 3/1982 | Boguslaski |
| RE30,985 | E | 6/1982 | Cartaya |
| 4,424,279 | A | 1/1984 | Bohn |
| 4,560,655 | A | 12/1985 | Baker |
| 4,657,866 | A | 4/1987 | Kumar |
| 4,676,980 | A | 6/1987 | Segal et al. |
| 4,737,456 | A | 4/1988 | Weng |
| 4,767,704 | A | 8/1988 | Cleveland |
| 4,816,567 | A | 3/1989 | Cabilly |
| 4,927,762 | A | 5/1990 | Darfler |
| 4,943,533 | A | 7/1990 | Mendelsohn |
| 4,965,199 | A | 10/1990 | Capon et al. |
| 5,122,469 | A | 6/1992 | Mather et al. |
| 5,212,290 | A | 5/1993 | Vogelstein |
| 5,457,105 | A | 10/1995 | Barker |
| 5,475,001 | A | 12/1995 | Barker |
| 5,500,362 | A | 3/1996 | Robinson |
| 5,545,806 | A | 8/1996 | Lonberg |
| 5,545,807 | A | 8/1996 | Surani et al. |
| 5,569,825 | A | 10/1996 | Lonberg |
| 5,571,894 | A | 11/1996 | Wels |
| 5,587,458 | A | 12/1996 | King |
| 5,591,828 | A | 1/1997 | Bosslet |
| 5,616,582 | A | 4/1997 | Barker |
| 5,624,821 | A | 4/1997 | Winter |
| 5,625,126 | A | 4/1997 | Lonberg |
| 5,633,425 | A | 5/1997 | Lonberg |
| 5,641,870 | A | 6/1997 | Rinderknecht |
| 5,648,237 | A | 7/1997 | Carter |
| 5,648,260 | A | 7/1997 | Winter |
| 5,654,307 | A | 8/1997 | Bridges |
| 5,661,016 | A | 8/1997 | Lonberg |
| 5,679,683 | A | 10/1997 | Bridges |
| 5,731,168 | A | 3/1998 | Carter |
| 5,747,498 | A | 5/1998 | Schnur |
| 5,750,373 | A | 5/1998 | Garrard |
| 5,760,041 | A | 6/1998 | Wissner |
| 5,770,429 | A | 6/1998 | Lonberg et al. |

(Continued)

FOREIGN PATENT DOCUMENTS

| | | | |
|---|---|---|---|
| DE | 266710 | A3 | 4/1989 |
| EP | 0183070 | A2 | 6/1986 |

(Continued)

OTHER PUBLICATIONS

Horn et al (Annals of Oncology, 2016, vol. 27, supplement 6, VI496, abstract 1431TiP).*

Mok et al Power Point Presentation at the Nov. 2018 ESMO Asia Congress (Annals of Oncology (2018) 29 (suppl_9): ix173-ix178. 10.1093/annonc/mdy483).*

Clinicaltrial.gov, NCT02763579, Revision History posted Jun. 7, 2017, "A Study of Carboplatin Plus Etoposide With or Without Atezolizumab in Participants With Untreated Extensive-Stage (ES) Small Cell Lung Cancer (SCLC) (IMpower133")."*

Lima et al.(2017 ASCO Annual Meeting, Jun. 2-6, 2017, Poster abstract #194528; https://www.g1therapeutics.com/file.cfm/34/docs/tr-G1_ASCO2017_RochaLima.pdf); and Yilmaz et al (Indian Journal of Cancer, 2011, 48:454-459).*

(Continued)

*Primary Examiner* — Laura B Goddard

(74) *Attorney, Agent, or Firm* — Clark & Elbing LLP; Thomas J. Takara

(57) ABSTRACT

The present disclosure provides methods for treating lung cancer (such as small cell lung cancer, e.g., extensive stage small cell lung cancer) in an individual. The methods comprise administering to the individual a PD-1 axis binding antagonist (such as an anti-PD-L1 antibody, e.g., atezolizumab), a platinum agent (e.g., cisplatin or carboplatin), and a topoisomerase II inhibitor (e.g., etoposide).

35 Claims, 24 Drawing Sheets

Specification includes a Sequence Listing.

(56) References Cited

U.S. PATENT DOCUMENTS

| | | | |
|---|---|---|---|
| 5,770,599 | A | 6/1998 | Gibson |
| 5,789,199 | A | 8/1998 | Pettit et al. |
| 5,804,396 | A | 9/1998 | Plowman |
| 5,807,706 | A | 9/1998 | Carter |
| 5,821,333 | A | 10/1998 | Carter |
| 5,821,337 | A | 10/1998 | Carter |
| 5,866,572 | A | 2/1999 | Barker |
| 5,869,046 | A | 2/1999 | Presta et al. |
| 5,891,996 | A | 4/1999 | Mateo |
| 5,959,177 | A | 9/1999 | Hein et al. |
| 6,002,008 | A | 12/1999 | Wissner |
| 6,040,498 | A | 3/2000 | Stomp et al. |
| 6,075,181 | A | 6/2000 | Kucherlapati |
| 6,084,095 | A | 7/2000 | Bridges |
| 6,140,332 | A | 10/2000 | Traxler |
| 6,150,584 | A | 11/2000 | Kucherlapati |
| 6,171,586 | B1 | 1/2001 | Lam |
| 6,194,551 | B1 | 2/2001 | Idusogie |
| 6,235,883 | B1 | 5/2001 | Jakobovits |
| 6,248,516 | B1 | 6/2001 | Winter et al. |
| 6,265,410 | B1 | 7/2001 | Bridges |
| 6,267,958 | B1 | 7/2001 | Andya |
| 6,344,455 | B1 | 2/2002 | Bridges |
| 6,344,459 | B1 | 2/2002 | Bridges |
| 6,391,874 | B1 | 5/2002 | Cockerill |
| 6,399,602 | B1 | 6/2002 | Barker |
| 6,417,429 | B1 | 7/2002 | Hein et al. |
| 6,420,548 | B1 | 7/2002 | Vezina et al. |
| 6,455,534 | B2 | 9/2002 | Bridges |
| 6,521,620 | B1 | 2/2003 | Bridges |
| 6,596,726 | B1 | 7/2003 | Bridges |
| 6,602,684 | B1 | 8/2003 | Umana et al. |
| 6,602,863 | B1 | 8/2003 | Bridges |
| 6,713,484 | B2 | 3/2004 | Bridges |
| 6,737,056 | B1 | 5/2004 | Presta |
| 6,919,436 | B2 | 7/2005 | Lihme |
| 6,982,321 | B2 | 1/2006 | Winter |
| 7,041,870 | B2 | 5/2006 | Tomizuka |
| 7,078,492 | B2 | 7/2006 | Pirofski |
| 7,087,409 | B2 | 8/2006 | Barbas, III |
| 7,125,978 | B1 | 10/2006 | Vézina et al. |
| 7,153,507 | B2 | 12/2006 | Van |
| 7,189,826 | B2 | 3/2007 | Rodman |
| 7,332,581 | B2 | 2/2008 | Presta |
| 7,371,826 | B2 | 5/2008 | Presta |
| 7,504,256 | B1 | 3/2009 | Ogawa |
| 7,527,791 | B2 | 5/2009 | Adams |
| 7,642,228 | B2 | 1/2010 | Carter |
| 7,695,936 | B2 | 4/2010 | Carter |
| 8,216,805 | B2 | 7/2012 | Carter |
| 8,217,149 | B2 | 7/2012 | Irving |
| 9,205,148 | B2 | 12/2015 | Langermann |
| 2002/0164328 | A1 | 11/2002 | Shinkawa et al. |
| 2003/0115614 | A1 | 6/2003 | Kanda |
| 2003/0157108 | A1 | 8/2003 | Presta |
| 2004/0093621 | A1 | 5/2004 | Shitara et al. |
| 2004/0109865 | A1 | 6/2004 | Niwa et al. |
| 2004/0110282 | A1 | 6/2004 | Kanda et al. |
| 2004/0110704 | A1 | 6/2004 | Yamane et al. |
| 2004/0132140 | A1 | 7/2004 | Satoh et al. |
| 2005/0014934 | A1 | 1/2005 | Hinton et al. |
| 2005/0026229 | A1 | 2/2005 | Reiter |
| 2005/0031613 | A1 | 2/2005 | Nakamura |
| 2005/0079574 | A1 | 4/2005 | Bond |
| 2005/0100546 | A1 | 5/2005 | Jakobovits |
| 2005/0119455 | A1 | 6/2005 | Fuh et al. |
| 2005/0123546 | A1 | 6/2005 | Umana et al. |
| 2005/0176122 | A1 | 8/2005 | Lihme |
| 2005/0260186 | A1 | 11/2005 | Bookbinder et al. |
| 2005/0266000 | A1 | 12/2005 | Bond et al. |
| 2005/0276805 | A1 | 12/2005 | Hanai |
| 2005/0287149 | A1 | 12/2005 | Keler |
| 2006/0059575 | A1 | 3/2006 | Kusunoki |
| 2006/0104968 | A1 | 5/2006 | Bookbinder et al. |
| 2006/0258841 | A1 | 11/2006 | Michl |
| 2007/0117126 | A1 | 5/2007 | Sidhu et al. |
| 2007/0134759 | A1 | 6/2007 | Nishiya |
| 2007/0160598 | A1 | 7/2007 | Dennis et al. |
| 2007/0237764 | A1 | 10/2007 | Birtalan et al. |
| 2007/0292936 | A1 | 12/2007 | Barthelemy et al. |
| 2008/0241884 | A1 | 10/2008 | Shitara |
| 2009/0002360 | A1 | 1/2009 | Chen et al. |
| 2010/0092997 | A1 | 4/2010 | Nakamura et al. |
| 2013/0034559 | A1 | 2/2013 | Queva |
| 2013/0089553 | A1 | 4/2013 | Carter |
| 2015/0210769 | A1 | 7/2015 | Freeman |
| 2015/0210772 | A1 | 7/2015 | Kim |
| 2016/0009805 | A1 | 1/2016 | Kowanetz |
| 2016/0108123 | A1 | 4/2016 | Freeman |
| 2020/0030443 | A1 | 1/2020 | Lopez-Chavez |

FOREIGN PATENT DOCUMENTS

| | | | |
|---|---|---|---|
| EP | 0244234 | A2 | 11/1987 |
| EP | 0308936 | A2 | 3/1989 |
| EP | 0402226 | A1 | 12/1990 |
| EP | 0404097 | A2 | 12/1990 |
| EP | 0659439 | A2 | 6/1995 |
| WO | 1987000195 | A1 | 1/1987 |
| WO | 1990003430 | A1 | 4/1990 |
| WO | 1991000360 | A1 | 1/1991 |
| WO | 1991010741 | A1 | 7/1991 |
| WO | 199200373 | A1 | 1/1992 |
| WO | 199301161 | A1 | 1/1993 |
| WO | 199308829 | A1 | 5/1993 |
| WO | 199316185 | A2 | 8/1993 |
| WO | 199316185 | A3 | 9/1993 |
| WO | 1994004690 | A1 | 3/1994 |
| WO | 199429351 | A2 | 12/1994 |
| WO | 199429351 | A3 | 2/1995 |
| WO | 199627011 | A1 | 9/1996 |
| WO | 199630347 | A1 | 10/1996 |
| WO | 199633977 | A1 | 10/1996 |
| WO | 199633978 | A1 | 10/1996 |
| WO | 199633980 | A1 | 10/1996 |
| WO | 1996033735 | A1 | 10/1996 |
| WO | 1996034096 | A1 | 10/1996 |
| WO | 199640210 | A1 | 12/1996 |
| WO | 1997030087 | A1 | 8/1997 |
| WO | 199814451 | A1 | 4/1998 |
| WO | 199824893 | A2 | 6/1998 |
| WO | 199824893 | A3 | 8/1998 |
| WO | 199843960 | A1 | 10/1998 |
| WO | 199850038 | A1 | 11/1998 |
| WO | 199850433 | A2 | 11/1998 |
| WO | 1998058964 | A1 | 12/1998 |
| WO | 199850433 | A3 | 2/1999 |
| WO | 199906378 | A1 | 2/1999 |
| WO | 199906396 | A1 | 2/1999 |
| WO | 199909016 | A1 | 2/1999 |
| WO | 199924037 | A1 | 5/1999 |
| WO | 1999022764 | A1 | 5/1999 |
| WO | 199951642 | A1 | 10/1999 |
| WO | 200061739 | A1 | 10/2000 |
| WO | 2001029246 | A1 | 4/2001 |
| WO | 200231140 | A1 | 4/2002 |
| WO | 2003011878 | A2 | 2/2003 |
| WO | 2003084570 | A1 | 10/2003 |
| WO | 2003085107 | A1 | 10/2003 |
| WO | 2003085119 | A1 | 10/2003 |
| WO | 2003011878 | A3 | 11/2003 |
| WO | 2004056312 | A2 | 7/2004 |
| WO | 2005035586 | A1 | 4/2005 |
| WO | 2005035778 | A1 | 4/2005 |
| WO | 2004056312 | A3 | 5/2005 |
| WO | 2005053742 | A1 | 6/2005 |
| WO | 2005100402 | A1 | 10/2005 |
| WO | 2006029879 | A2 | 3/2006 |
| WO | 2006044908 | A2 | 4/2006 |
| WO | 2006044908 | A3 | 8/2006 |
| WO | 2006029879 | A3 | 9/2006 |
| WO | 2006121168 | A1 | 11/2006 |
| WO | 2007005874 | A2 | 1/2007 |
| WO | 2007005874 | A3 | 7/2007 |

(56) References Cited

FOREIGN PATENT DOCUMENTS

| | | | | |
|---|---|---|---|---|
| WO | 2008077546 A1 | | 7/2008 | |
| WO | 2009101611 A1 | | 8/2009 | |
| WO | 2009114335 A2 | | 9/2009 | |
| WO | 2010027827 A2 | | 3/2010 | |
| WO | 2010027827 A3 | | 5/2010 | |
| WO | 2009114335 A3 | | 6/2010 | |
| WO | 2010077634 A1 | | 7/2010 | |
| WO | 2011066342 A2 | | 6/2011 | |
| WO | 2011066389 A1 | | 6/2011 | |
| WO | 2011066342 A3 | | 7/2011 | |
| WO | 2011161699 A2 | | 12/2011 | |
| WO | 2011161699 A3 | | 5/2012 | |
| WO | 2012145493 A1 | | 10/2012 | |
| WO | 2012168944 A1 | | 12/2012 | |
| WO | 2013132317 A1 | | 9/2013 | |
| WO | 2013144704 A1 | | 10/2013 | |
| WO | 2013181634 A2 | | 12/2013 | |
| WO | 2013181634 A3 | | 3/2014 | |
| WO | WO-2014151006 A2 | * | 9/2014 | A61K 39/39558 |
| WO | 2014151006 A3 | | 11/2014 | |
| WO | 2014179664 A2 | | 11/2014 | |
| WO | 2014194302 A2 | | 12/2014 | |
| WO | 2014206107 A1 | | 12/2014 | |
| WO | 2014179664 A3 | | 2/2015 | |
| WO | 2014194302 A3 | | 2/2015 | |
| WO | 2015033299 A1 | | 3/2015 | |
| WO | 2015033301 A1 | | 3/2015 | |
| WO | 2015033303 A1 | | 3/2015 | |
| WO | 2015035606 A1 | | 3/2015 | |
| WO | 2015036927 A1 | | 3/2015 | |
| WO | 2015044900 A1 | | 4/2015 | |
| WO | 2015085847 A1 | | 6/2015 | |
| WO | 2015095404 A2 | | 6/2015 | |
| WO | 2015112800 A1 | | 7/2015 | |
| WO | 2015112805 A1 | | 7/2015 | |
| WO | 2015112900 A1 | | 7/2015 | |
| WO | 2015095404 A3 | | 8/2015 | |
| WO | 2015119923 A1 | | 8/2015 | |
| WO | 2015119930 A1 | | 8/2015 | |
| WO | 2016000619 A1 | | 1/2016 | |
| WO | 2016032927 A1 | | 3/2016 | |
| WO | 2016061142 A1 | | 4/2016 | |
| WO | 2016089873 A1 | | 6/2016 | |
| WO | 2016106160 A1 | | 6/2016 | |
| WO | WO-2016/149201 A2 | | 9/2016 | |
| WO | WO-2018035413 A1 | | 2/2018 | |
| WO | WO-2018115051 A1 | * | 6/2018 | A61P 35/00 |

OTHER PUBLICATIONS

Yilmaz et al (Indian Journal of Cancer, 2011, 48:454-459).*

Velcheti et al (J Clinical Oncology, May 20, 2018, 36, 15_suppl, abstract 12001).*

Lawrence (Oct. 18, 2017; CancerNetwork.com, https://www.cancernetwork.com/view/high-tumor-mutation-burden-sclc-may-predict-improved-immunotherapy-response).*

Socinski et al (NEJM, Jun. 14, 2018, 378:2288-2301).*

Socinski et al PROTOCOL of NEJM, Jun. 14, 2018, 378:2288-2301.*

Gandhi et al (NEJM, May 31, 2018, 378:2078-2092).*

Gandhi et al PROTOCOL of NEJM, May 31, 2018, 378:2078-2092.*

Horn et al., "Mpower133: a Phase 1/111 Study of 1L Atezolizumab with Carboplatin and Etoposide in Patients with Extensive-Stage SCLC," Journal of Thoracic Oncology, 11(11);S305-S306, Nov. 1, 2016.

Nct02763570, A Study of Carboplatin Plus Etoposide With or Without Atezolizumab in Participants With Untreated Extensive-Stage (ES) Small Cell Lung Cancer (SCLC) (IMpower133), Jun. 18, 2018.

ABT-874/J695 is A Fully Human Anti-IL-12/23 Monoclonal Antibody Designed to Target and Neutralize IL-12, A Protein That Regulates Inflammatory Response and Is Expressed in MS Lesions, 2 pages.

Almagro, J.C. et al. (Jan. 1, 2008). "Humanization of Antibodies," Frontiers in Bioscience 13:1619-1633.

American Cancer Society "Small Cell Lung Cancer Survival Rates, by Stage," retrieved from www.cancer.org/cancer/small-cell-lung-cancer/detection-diagnosis-staging/survival-rates.html, last visited Oct. 15, 2019, 4 pages.

ATCC Product Sheet 12,424 (2018), 1 page.

ATCC Product Sheet 16,045 (2018), 2 pages.

ATCC Product Sheet 20,622 (2019), 1 page.

ATCC Product Sheet 24,178 (2018), 2 pages.

ATCC Product Sheet 27,325 (2018), 2 pages.

ATCC Product Sheet 31,446 (2018), 2 pages.

ATCC Product Sheet 31,537 (2018), 1 page.

ATCC Product Sheet 36,906 (2018), 1 page.

ATCC Product Sheet 38,626 (2019), 1 page.

ATCC Product Sheet 56,500 (2018), 2 pages.

ATCC Product Sheet CCL 10 (2018), 3 pages.

ATCC Product Sheet CCL 2 (2018), 3 pages.

ATCC Product Sheet CCL 34 (2018), 3 pages.

ATCC Product Sheet CCL 51 (2018), 3 pages.

ATCC Product Sheet CCL 75 (2018), 3 pages.

ATCC Product Sheet CRL 1442 (2018), 3 pages.

ATCC Product Sheet CRL 1651 (2018), 2 pages.

ATCC Product Sheet CRL-1587 (2018), 2 pages.

ATCC Product Sheet CRL-9096, (2018), 2 pages.

ATCC Product Sheet HB 8506, (2019), 1 page.

ATCC Product Sheet HB 8507, (2019), 1 page.

ATCC Product Sheet HB-8508, (2019). 1 page.

ATCC Product Sheet HB-8509, (2019), 1 page.

Baca, M. et al. (Apr. 18, 1997). "Antibody Humanization Using Monovalent Phage Display," J. Biol. Chem. 272 (16):10678-10684.

Barnes, D et al. (Mar. 1, 1980). "Methods for Growth of Cultured Cells In Serum-Free Medium," Anal. Biochem. 102(2):255-270.

Bergman, B et al. (1994). "The EORTC QLQ-LC13: A Modular Supplement to the EORTC Core Quality of Life Questionnaire (QLQ-C30) for Use in Lung Cancer Clinical Trials. EORTC Study Group on Quality of Life," Eur J Cancer 30A(5):635-642.

Boerner, P. et al. (Jul. 1, 1991). "Production of Antigen-Specific Human Monoclonal Antibodies From in Vitro-Primed Human Splenocytes," J. Immunol. 147(1):86-95.

Borrebaeck, C.A.K. (1995). "Strategies for Humanizing Antibodies," in Antibody Engineering 2nd Ed. pp. 179-181.

Brennan, M. et al. (Jul. 5, 1985). "Preparation of Bispecific Antibodies by Chemical Recombination of Monoclonal Immunoglobulin G1 Fragments," Science 229:81-83.

Brodeur, B.R. et al. (1987). "Mouse-Human Myeloma Partners for the Production of Heterohybridomas," Chapter 4 in Monoclonal Antibody Production Techniques and Applications, Marcel Dekker, Inc. New York, New York, pp. 51-63.

Brüggemann, M. et al. (1993). "Designer Mice: The Production of Human Antibody Repertoires in Transgenic Animals," Year in Immunol. 7:33-40.

Brüggemann, M. et al. (Nov. 1, 1987). "Comparison of the Effector Functions of Human Immunoglobulins Using a Matched Set of Chimeric Antibodies," J. Exp. Med. 166:1351-1361.

Calvert et al. (Nov. 1989). "Carboplatin Dosage: Prospective Evaluation of a Simple Formula Based on Renal Function." J. Clin. Oncol. 7(11):1748-1756.

Cancer Fact Sheets Worldwide in 2012. Retrieved from http://globocan.iarc.fr/Pages/fact_sheets_cancer.aspx, last visited Oct. 15, 2019, 6 pages.

Carter, P et al. (Feb. 1992). "High Level Escherichia Coli Expression and Production of a Bivalent Humanized Antibody Fragment," Bio/Technology 10:163-167.

Carter, P. et al. (May 1992). "Humanization of an Anti-p185HER2 Antibody for Human Cancer Therapy," Proc. Natl. Acad. Sci. USA 89:4285-4289.

CAS Registry No. 1036730-42-3, 3 pages.

CAS Registry No. 1374853-91-4, 2 pages.

CAS Registry No. 1422184-00-6, Oct. 18, 2019, 2 pages.

CAS Registry No. 1422185-06-5, Oct. 18, 2019, 2 pages.

CAS Registry No. 1428935-60-7, Oct. 18, 2019, 2 pages.

CAS Registry No. 1537032-82-8, Oct. 18, 2019, 2 pages.

(56) References Cited

OTHER PUBLICATIONS

CAS Registry No. 1859072-53-9, 2 pages.
Champe, M. et al. (Jan. 20, 1995). "Monoclonal Antibodies That Block the Activity of Leukocyte Function-Associated Antigen 1 Recognize Three Discrete Epitopes in the Inserted Domain of CD11a," J. Biol. Chem. 270 (3):1388-1394.
Charlton, K.A. (2004). "Expression and Isolation of Recombinant Antibody Fragments in *E. coli,*" Methods Mol Biol 248:245-254.
ChemIDplus. (Apr. 1, 2019). "ChemIDSplus, RN: CAS Registry No. 946414-94-4M Unii: 31YO63LBSN, Substance Name: Nivolumab," located at http://chem.nlm.nih.gov/chemidplus/rn/946414-94-4, last visited on Apr. 1, 2019, 2 pages.
Chen, Y. et al. (1999). "Selection and Analysis of an Optimized Anti-VEGF Antibody: Crystal Structure of an Affinity-Matured Fab in Complex With Antigen," J. Mol. Biol 293:865-881.
Chothia, C. (1976). "The Nature of the Accessible and Buried Surfaces in Proteins," J. Mol. Biol. 105:1-14.
Chothia, C et al. (Aug. 20, 1987). "Canonical Structures for the Hypervariable Regions of Immunoglobulins," J. Mol. Biol. 196(4):901-917.
Chowdhury, P.S. (2008). "Engineering Hot Spots for Affinity Enhancement of Antibodies," Methods Mol. Biol. 207:179-196.
Clackson, T. et al. (Aug. 15, 1991). "Making Antibody Fragments Using Phage Display Libraries," Nature 352:624-628.
CLINICALTRIALS.gov Identifier NCT00889954, "Her2 and TGFBeta Cytotoxic T Cells in Treatment of Her2 Positive Malignancy (HERCREEM)," 8 pages.
Clynes, R. et al. (Jan. 1998). "Fc Receptors are Required in Passive and Active Immunity to Melanoma," Proc. Natl. Acad. Sci. USA 95:652-656.
Cockcroft, D.W. et al. (1976). "Prediction of Creatinine Clearance From Serum Creatinine," Nephron 16(1):31-41.
Cole, S.P.C. et al. (1985). "The EBV-Hybridoma Technique and its Application to Human Lung Cancer," Monoclonal Antibodies and Cancer Therapy, Alan R. Liss, Inc., New York, New York, pp. 77-96.
Cragg, M.S. et al. (Apr. 1, 2004, e-pub. Oct. 9, 2003). "Antibody Specificity Controls In Vivo Effector Mechanisms of Anti-CD20 Reagents," Blood 103(7):2738-2743, 7 pages.
Cragg, M.S. et al. (Feb. 1, 2003). "Complement-Mediated Lysis by Anti-CD20 Mab Correlates With Segregation Into Lipid Rafts," Blood 101(3):1045-1052.
Cunningham, B.C. et al. (Jun. 2, 1989). "High-Resolution Epitope Mapping of hGH-Receptor Interactions by Alanine-Scanning Mutagenesis," Science 244:1081-1085.
Dall'Acqua, W.F. et al. (2005). "Antibody Humanization by Framework Shuffling," Methods 36:43-60.
Demedts, I.K. et al. (Jan. 2010). "Treatment of Extensive-Stage Small Cell Lung Carcinoma: Current Status and Future Prospects," Eur Respir J. 35(1):202-215.
Duncan, A.R. et al. (Apr. 21, 1988). "The Binding Site for C1q on IgG," Nature 322:738-740.
Eisenhauer, E.A. et al. (2009) "New Response Evaluation Criteria in Solid Tumors: Revised RECIST Guideline (version 1.1)," Eur. J. Cancer 45:228-247.
Even, M.S. et al. (Mar. 2006). "Serum-Free Hybridoma Culture: Ethical, Scientific and Safety Considerations," Trends in Biotechnology 24(3):105-108.
Fellouse, F.A. et al. (Aug. 24, 2004). "Synthetic Antibodies From a Four-Amino-Acid Code: A Dominant Role for Tyrosine in Antigen Recognition," Proc. Natl. Acad. Sci. USA 101(34):12467-12472.
Ferrara, C. et al. (2006, e-pub. Jan. 24, 2006). "Modulation of Therapeutic Antibody Effector Functions by Glycosylation Engineering: Influence of Golgi Enzyme Localization Domain and Co-Expression of Heterologous β1, 4-N-Acetylglucosaminyltransferase III and Golgi α-Mannosidase II," Biotechnology and Bioengineering 93(5):851-861.
Fleer, R. et al. (Oct. 1, 1991). "Stable Multicopy Vectors for High-Level Secretion of Recombinant Human Serum Albumin by Kluyveromyces Yeasts," Bio/Technology 9(10):968-975.
Foster, N.R. et al. (Jun. 15, 2009). "Prognostic Factors Differ by Tumor Stage for Small Cell Lung Cancer: A Pooled Analysis of North Central Cancer Treatment Group Trials," Cancer 115(12):2721-2731, 21 pages.
Franek, F. (2005). "Oligopeptides as Tools for Improving Productivity of Hypbridoma Cells Cultures," Chapter VI in Trends in Monoclonal Antibody Research, Marie A. Simmons, ed., Nova Science Publishers, Inc. pp. 111-122.
Gazzano-Santoro, H. et al. (1997). "A Non-Radioactive Complement-Dependent Cytotoxicity Assay for Anti-CD20 Monoclonal Antibody," J. Immunol. Methods 202:163-171.
Gerngross, T.U. (Nov. 2004). "Advances in the Production of Human Therapeutic Proteins in Yeasts and Filamentous Fungi," Nature Biotechnology 22(11):1409-1414.
Goding, J.W. (1983). Monoclonal Antibodies: Principles and Practice, pp. 56-103.
Govindan, R. et al. (Oct. 1, 2006). "Changing Epidemiology of Small-Cell Lung Cancer in the United States Over The Last 30 Years: Analysis of the Surveillance, Epidemiologic, and End Results Database," J Clin Oncol. 24 (28):4539-4544.
Graham. F.L. et al. (1977). "Characteristics of a Human Cell Line Transformed by DNA from Human Adenovirus Type 5," J. Gen Virol. 36:59-72.
Griffiths, A.D. et al. (1993). "Human Anti-Self Antibodies With High Specificity From Phage Display Libraries," EMBO J. 12(2):725-734.
Gruber, M. et al. (1994). "Efficient Tumor Cell Lysis Mediated by a Bispecific Single Chain Antibody Expressed in *Escherichia coli,*" J. Immunol. 152:5368-5374.
Guss, B. et al. (Jul. 1986). "Structure of the lgG-Binding Regions of Streptococcal Protein G," EMBO J. 5 (7):1567-1575.
Guyer, R.L. et al. (Aug. 1976). "Immunoglobulin Binding by Mouse Intestinal Epithelial Cell Receptors," J. Immunol. 117(2):587-593.
Ham, R.J. et al. (1979). "Media and Growth Requirements," Meth. Enz. 58:44-93.
Hamers-Casterman, C. et al. (Jun. 3, 1993). "Naturally Occurring Antibodies Devoid of Light Chains," Nature 363:446-448.
Hammerling, G.J. et al. (1981). "Production of Antibody-Producing Hybridomas in the Rodent Systems," in Research Monographs in Immunology, Elsevier/North-Holland Biomedical Press 3:563-587.
Harlow, E. et al. (1988). Antibodies: A Laboratory Manual, Cold Spring Harbor Laboratory pp. 53-137.
Harris, W.J. (1995). "Therapeutic Monoclonal. Production of Humanized Monoclonal Antibodies for In Vivo Imaging and Therapy," Biochem. Soc. Transactions 23:1035-1038.
Hellstrom, I. et al. (Mar. 1985). "Strong Antitumor Activities of IgG3 Antibodies to a Human Melanoma-Associated Ganglioside," Proc. Natl. Acad. Sci. USA 82:1499-1502.
Hellstrom, I. et al. (Sep. 1986). "Antitumor Effects of L6, an IgG2a Antibody That Reacts With Most Human Carcinomas," Proc. Natl. Acad. Sci. USA 83:7059-7063.
Holliger, P. et al. (Jul. 1993). "Diabodies": Small Bivalent And Bispecific Antibody Fragments, Proc. Natl. Acad. Sci. USA 90:6444-6448.
Hongo, J.A.S. et al. (1995). "Development and Characterization of Murine Monoclonal Antibodies to the Latency-Associated Peptide of Transforming Growth Factor β1," Hybridoma 14(3):253-260.
Hoogenboom, H.R. et al. (Sep. 20, 1992). "By-Passing Immunisation. Human Antibodies From Synthetic Repertoires of Germline VH Gene Segments Rearranged in Vitro," J. Mol. Biol. 227:381-388.
Hoogenboom, H.R. et al. (2001) "Overview of Antibody Phage-Display Technology and Its Applications," Methods in Molecular Biology 178:1-37.
Horn, L. et al. (2016). "A Phase III Study of Atezolizumab With Cartoplatin Plus Etopside in Patients With Extensive-Stage Small Cell Lung Cancer (IMpower133)," Annals of Oncology 27(Supple. 6):vi493-vi496, Abstract 1431TIP, 1 page.
Horn, L. et al. (Nov. 2016)."IMpower133: A Phase I/III Study of 1L Atezolimzumab with Carboplatin and Etoposide in Patients with Extensive-Stage SCLC," Abstract: PS01.57, Journal of Thoracic Oncology 11(11):S305-S306.

(56) References Cited

OTHER PUBLICATIONS

Hudson, P.J. et al. (Jan. 2003). "Engineered Antibodies," Nat. Med. 9(1):129-134.
Hurle, M.R. et al. (1994). "Protein Engineering Techniques for Antibody Humanization," Curr. Op. Biotech. 5:428-433.
Idusogie, E.E. et al. (2000). "Mapping of the C1q Binding Site on Rituxan, a Chimeric Antibody With a Human IgG1 Fc," J. Immunol. 164:4178-4184.
International Preliminary Report on Patentability, issued Dec. 29, 2020, for PCT Application No. PCT/US2019/038534, filed Jun. 21, 2019, 7 pages.
International Search Report and Written Opinion, mailed Aug. 29, 2019, for PCT Application No. PCT/US2019/038534, filed Jun. 21, 2019, 15 pages.
Jakobovits, A. et al. (Mar. 18, 1993). "Germ-Line Transmission and Expression of a Human-Derived Yeast Artificial Chromosome," Nature 362:255-258.
Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90:2551-2555.
Jean, F. et al. (2017). "Atezolizumab: Feasible Second-Line Therapy for Patients with Non-Small Cell Lung Cancer? A Review of Efficacy, Safety and Place in Therapy," Therapeutic Advances in Medical Oncology 9(12):769-779.
Jemal, A et al. (Mar.-Apr. 2011, e-pub. Feb. 4, 2011). "Global Cancer Statistics," CA Cancer J. Clin 61(2):69-90.
Johns, F.G. et al. (Jul. 16, 2004, e-pub. Apr. 9, 2004). "Identification of the Epitope for the Epidermal Growth Factor Receptor-Specific Monoclonal Antibody 806 Reveals that it Preferentially Recognizes an Untethered Form of the Receptor," J. Biol. Chem. 279(29):30375-30374.
Johnson, B.E. et al. (Apr. 2004). "Basic Treatment Considerations Using Chemotherapy for Patients With Small Cell Lung Cancer," Hematol Oncol Clin North Am. 18(2):309-322.
Johnson, G. et al. (2003). "The Kabat Database and a Bioinformatics Example," Chapter 2 in Methods in Molecular Biology, Lo, B.K.C., ed., Human Press, Totowa, N.J., 248:1-25.
Jones, E.W. (Jan. 1977). "Proteinase Mutants of *Saccharomyces cerevisiae,*" Genetics 85(1):23-33.
Jones, P.T. et al. (May 29, 1986). "Replacing the Complementarity-Determining Regions in a Human Antibody With Those From a Mouse," Nature 321:522-525.
Kabat, E.A. et al. (1991). Sequences of Proteins of Immunological Interest, 5th ed., Public Health Service, National Institutes of Health, Bethesda, MD. TOC, 21 pages.
Kanda, Y. et al. (Jul. 5, 2006, e-pub. Apr. 11, 2006). "Comparison of Cell Line for Stable Production of Fucose-Negative Antibodies with Enhanced ADCC," Biotechnol. Bioeng. 94(4):680-688.
Kashmiri, S.V et al. (2005). "SDR Grafting—A New Approach to Antibody Humanization," Methods 36:25-34.
Kim, J-K. et al. (1994). "Localization of the Site of the Murine IgGI Molecule That is Involved in Binding to the Murine Intestinal Fc Receptor," Eur. J. Immunol. 24:2429-2434.
Klimka, A et al. (2000). "Human Anti-CD30 Recombinant Antibodies by Guided Phage Antibody Selection Using Cell Panning," Br. J. Cancer 83(2):252-260.
Kostelny, S.A. et al. (Mar. 1, 1992). "Formation of a Bispecific Antibody by the Use of Leucine Zippers," J. Immunol. 148(5):1547-1553.
Kozbor, D. et al. (Dec. 1984). "A Human Hybrid Myeloma for Production of Human Monoclonal Antibodies," J. Immunol. 133(6):3001-3005.
Köhler, G. et al. (Aug. 7, 1975). "Continuous Cultures of Fused Cells Secreting Antibody of Predefined Specificity," Nature 256:495-497.
Lawrence, L. et al. (Oct. 18, 2017). "High Tumor Mutation Burden in SCLC May Predict Improved Immunotherapy Response," Retrieved from the Internet https://www.cancernetwork.com/view/high-tumor-mutation-burden-scic-may-predict-improved-immunotherapy-response, last visited Oct. 19, 2021, 4 pages.
Lee, C.V. et al. (2004). "Bivalent Antibody Phage Display Mimics Natural Immunoglobulin," J. Immunol. Methods 284 (1-2):119-132.
Lee, C.V. et al. (2004). "High-Affinity Human Antibodies From Phage-Displayed Synthetic Fab Libraries With a Single Framework Scaffold," J. Mol. Biol. 340:1073-1093.
Li, H. et al. (Feb. 2006, e-published on Jan. 22, 2006). "Optimization of Humanized IgGs in Glycoengineered Pichia Pastoris," Nature Biotechnology 24(2):210-215.
Li, J. et al. (Mar. 7, 2006). Human Antibodies for Immunotherapy Development Generated via a Human B Cell Hybridoma Technology, Proc. Natl. Acad. Sci. USA 103(10):3557-3562.
Lima, C.M.S.D. et al. (Jun. 2-6, 2017). "Trilaciclib (G1T28): A Cyclin Dependent Kinase 4/6 Inhibitor, in Combination With Etoposide and Carboplatin (EP) Foll Extensive State Small Cell Lung Cancer (ES-SCLC): Phase 1b Results," ASCO Annual Meeting Poster Abstract # 194528, 1 page. Poor Copy
Lindmark, R. et al. (1983). "Binding of Immunoglobulins to Protein A and Immunoglobulin Levels in Mammalian Sera," J. Immunol. Meth. 62:1-13.
Lonberg, N. (2008, e-pub. Jul. 21, 2008). "Fully Human Antibodies From Transgenic Mouse and Phage Display Platforms," Curr. Opin. Immunol. 20:450-459.
Lonberg, N. (Sep. 2005). "Human Antibodies From Transgenic Animals," Nat. Biotech. 23(9):1117-1125.
Lonberg, N. et al. (1995, e-pub. Jul. 10, 2009). "Human Antibodies From Transgenic Mice," Int. Rev. Immunol. 13 (1):65-93.
Lonberg, N. et al. (Apr. 28, 1994). "Antigen-Specific Human Antibodies From Mice Comprising Four Distinct Genetic Modifications," Nature 368(6474):856-859.
Marks et al., "By-passing immunization. Human antibodies from V-gene libraries displayed on phage," J Mol Biol (1991) 222(3):581-597.
Marks, J.D. et al. (2004) "Selection of Human Antibodies from Phage Display Libraries," Chapter 8 in Methods in Molecular Biology, Lo, B.K.C. (ed.), Humana Press Inc., Totowa, NJ, 248:161-176, 29 pages.
Marks, J.D. et al. (Jul. 1992). "By-Passing Immunization: Building High Affinity Human Antibodies by Chain Shuffling," Bio/Technology 10:779-783.
Mather, J.P. (1980). "Establishment and Characterization of Two Distinct Mouse Testicular Epithelial Cell Lines," Biol. Reprod. 23:243-251.
Mather, J.P. et al. (1982). "Culture of Testicular Cells in Hormone-Supplemented Serum-Free Medium," Annals N.Y. Acad. Sci. 383:44-68.
Mccafferty, J. et al. (Dec. 6, 1990). "Phage Antibodies: Filamentous Phage Displaying Antibody Variable Domains," Nature 348:552-554.
Micke, P. et al. (Sep. 2002) "Staging Small Cell Lung Cancer: Veterans Administration Lung Study Group Versus International Association for the Study of Lung Cancer-What Limits Limited Disease?" Lung Cancer 37 (3):271-276.
Milstein, C. et al. (Oct. 6, 1983). "Hybrid Hybridomas and Their Use in Immunohistochemistry," Nature 305:537-540.
Mok, T.S.K et al. (Nov. 2018). "Impower133: Primary Efficacy and Safety + CNS-Related Adverse Events in a Ph1/3 Study of First-Line Atezolizumab + Carboplatin + Etoposide in Extensive Stage SCLC (ES-SCLC)," Annals of Oncology 29(Suppl. 9):ix173-ix178, 20 pages.
Morimoto, K. et al. (1992). "Single-Step Purification of F(AB')2 Fragments of Mouse Monoclonal Antibodies (Immunoglobulins G1) by Hydrophobic Interaction High Performance Liquid Chromatography Using TSKgel Phenyl-5PW," J. Biochem. Biophys. Method 24:107-117.
Morrison, S.L. (Apr. 28, 1994). "Success in Specification," Nature 368:812-813.
Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.

(56) References Cited

OTHER PUBLICATIONS

Munson, P.J. et al. (1980). "LIGAND: A Versatile Computerized Approach for Characterization of Ligand-Binding Systems," Anal. Biochem. 107:220-239.
Murakami, M.S. et al. (1995). "Cell Cycle Regulation, Oncogenes, and Antineoplastic Drugs," in The Molecular Basis of Cancer, Chapter 1, 17 pages.
Neuberger, M. (Jul. 1996). "Generating High-Avidity Human Mabs in Mice," Nature Biotechnol. 14:826.
Ni, J. (2006). "Research Progress and Future Perspectives in Antibodomics and Antibodomic Drugs," Xiandai Mianyixue 26(4):265-268.(Translation of the Abstract 3 pages.).
Nicolaou, K.C. et al. (1994). "Calicheamicin θ1[1]: A Rationally Designed Molecule with Extremely Potent and Selective DNA Cleaving Properties and Apoptosis Inducing Activity," Angew. Chem. Intl. Ed. Engl. 33(2):183-186.
Nishino, M. et al. (Jul. 15, 2013). "Developing a Common Language for Tumor Response to Immunotherapy: Immune-Related Criteria Using Unidimentional Measurements," Clin Can Res. 19:3936-3943, 17 pages.
Non-Final Office Action, dated Oct. 22, 2021, for U.S. Appl. No. 16/449,105, filed Jun. 21, 2019, 21 pages.
Non-Final Office Action, mailed Feb. 13, 2023, for U.S. Appl. No. 16/449,105, filed Jun. 21, 2019, 22 pages.
Non-Final Office Action, mailed Jun. 10, 2022, for U.S. Appl. No. 16/449,105, filed Jun. 21, 2019, 16 pages.
Okazaki, A. et al. (Mar. 5, 2004). "Fucose Depletion From Human IgG1 Oligosaccharide Enhances Binding Enthalpy and Association Rate Between IgG1 and FcyRIIIa," J. Mol. Biol. 336(5):1239-1249.
Oken, M.M. et al. (Dec. 1982). "Toxicity and Response Criteria of the Eastern Cooperative Oncology Group," Am J Clin Oncol. 5(6):649-655.
Osbourn, J. et al. (2005). "From Rodent Reagents to Human Therapeutics Using Antibody Guided Selection," Methods 36:61-68.
Padlan, E.A. (1991). "A Possible Procedure for Reducing the Immunogenicity of Antibody Variable Domains While Preserving Their Ligand-Binding Properties," Mol. Immunol. 28(4/5):489-498.
Pesch, B. et al. (Sep. 1, 2012, e-pub. Dec. 14, 2011). "Cigarette Smoking and Lung Cancer—Relative Risk Estimates for the Major Histological Types From a Pooled Analysis of Case-Control Studies," Int J Cancer 131 (5):1210-1219), 19 pages.
Petkova, S.B. et al. (2006, e-pub. Oct. 31, 2006). "Enhanced Half-Life of Genetically Engineered Human IgG1 Antibodies in a Humanized FcRn Mouse Model: Potential Application in Humorally Mediated Autoimmune Disease," Int'l. Immunol. 18(12):1759-1769.
Plückthun, A. (1994). "Antibodies from *Escherichia coli*," in Chapter 11 The Pharmacology of Monoclonal Antibodies, vol. 113, Rosenburg and Moore eds., Springer-Verlag, New York, pp. 269-315, 48 pages.
Poklar, N. et al. (Jul. 1996). "Influence Of Cisplatin Intrastrand Crosslinking on the Conformation, Thermal Stability, and Energetics of a 20-Mer DNA Duplex," Proc. Natl. Acad. Sci. U.S.A. 93(15):7606-7611.
Presta, L.G. (1992). "Antibody Engineering," Current Opinion in Structural Biology 2:593-596.
Presta, L.G. et al. (Sep. 1, 1993). "Humanization of an Antibody Directed Against IgE," J. Immunol. 151 (5):2623-2632.
Queen, C. et al. (Dec. 1989). "A Humanized Antibody That Binds to the Interleukin 2 Receptor," Proc. Natl Acad. Sci. USA 86:10029-10033.
Ravetch, J.V. et al. (1991). "Fc Receptors," Annu. Rev. Immunol. 9:457-492.
Remington's Pharmaceutical Sciences. (1980). 16th edition, Osol, A. Ed, pp. 1-2, (Table of Contents Only).
Riechmann, L. et al. (Mar. 24, 1988). "Reshaping Human Antibodies for Therapy," Nature 332:323-327.
Ripka, J. et al. (Sep. 1986). "Two Chinese Hamster Ovary Glycosylation Mutants Affected in the Conversion of GDP-Mannose to GDP-Fucose," Arch Biochem Biophys. 249(2):533-545.
Rosok, M.J. et al. (Sep. 13, 1996). "A Combinatorial Library Strategy for the Rapid Humanization of Anticarcinoma BR96 Fab," J. Biol. Chem. 271(37):22611-22618.
Rudd, G.N. et al. (1995). "Persistence of Cisplatin-Induced DNA Interstrand Crosslinking in Peripheral Blood Mononuclear Cells From Elderly and Young Individuals," Cancer Chemother. Pharmacol. 35(4):323-326.
Shalaby, M.R. et al. (Jan. 1, 1992). "Development of Humanized Bispecific Antibodies Reactive With Cytotoxic Lymphocytes and Tumor Cells Overexpressing the HER2 Protooncogene," J. Exp. Med. 175:217-225.
Shaw, A.T. et al. (Sep. 2017). "1380TiP—A Randomized, Open-Label Comparison of Lorlatinib Versus Crizotinib as First-Line Treatment for Advanced Anaplastic Lymphoma Kinase (ALK)-Positive Non-Small Cell Lung Cancer," Annals of Oncology 28(Suppl. 5):493, 1 page.
Sheriff, S. et al. (Sep. 1996). "Redefining the Minimal Antigen-Binding Fragment," Nature Struct. Biol. 3 (9):733-736.
Shields, R.L. et al. (Mar. 2, 2001). "High Resolution Mapping of the Binding Site on Human IgG1 for FcγRI, FcγRII. FcγRIII, and FcRn and Design of IgG1 Variants With Improved Binding to the FcγR," J. Biol. Chem. 276(9):6591-6604.
Sidhu, S.S. et al. (2004). "Phage-Displayed Antibody Libraries Synthetic Heavy Chain Complementarity Determining Regions," J. Mol. Biol. 338(2):299-310.
Siegel, R.L. et al. (Jan.-Feb. 2015, e-pub. Jan. 5, 2015). "Cancer Statistics, 2015," CA Cancer J Clin. 65 (1):5-29.
Sims, M.J. et al. (Aug. 15, 1993). "A Humanized CD18 Antibody Can Block Function Without Cell Destruction," J. Immunol. 151(4):2296-2308.
Socinski, M.A. et al. (Oct. 1, 2009, e-pub. Aug. 31, 2009). "Phase III Study of Pemetrexed Plus Carboplatin Compared With Etoposide Plus Carboplatin in Chemotherapy-Naive Patients With Extensive-Stage Small-Cell Lung Cancer," J Clin Oncol. 27(28):4787-4792.
Spiess, C. et al. (Aug. 2013, e-pub. Jul. 7, 2013). "Bispecific Antibodies With Natural Architecture Produced by Co-Culture of Bacteria Expressing Two Distinct Half-Antibodies," Nature Biotech. 31(8):753-758.
Stinchcomb, D.T. et al. (Nov. 1, 1979). "Isolation and Characterisation of a Yeast Chromosomal Replicator", Nature, 282:39-43.
Stinchcombe, T.E. et al. (2010, e-pub. Feb. 9, 2010). "Limited-Stage Small Cell Lung Cancer: Current Chemoradiotherapy Treatment Paradigms," Oncologist 15(2):187-195.
Stragliotto, G. et al. (Apr. 1996). "Multiple Infusion of Anti-Epidermal Growth Factor Receptor (EGFR) Monoclonal Antibody (EMD 55,900) in Patient with Recurrent Malignant Gliomas," Eur. J. Cancer 32A(4):636-640.
Suresh, M.R. et al. (1986). "Bispecific Monoclonal Antibodies From Hybrid Hybridomas," Methods in Enzymology 121:210-228, 19 pages.
The EuroQol Group (Dec. 1990). "EuroQol—A New Facility for the Measurement of Health-Related Quality of Life," Health Policy 16(3):199-208.
Therasse, P. et al. (Feb. 2, 2000). "New Guidelines to Evaluate the Response to Treatment in Solid Tumors," J. Natl. Cancer Inst. 92(3):205-216.
Topalian, S.L. et al. (Jun. 28, 2012). "Safety, Activity, and Immune Correlates of Anti-PD-1 Antibody in Cancer," N. Engl. J. Med. 366(26):2443-2454, 19 pages.
Traunecker, A. et al. (1991). "Bispecific Single Chain Molecules (Janusins) Target Cytotoxic Lymphocytes on HIV Infected Cells," EMBO J. 10(12):3655-3659.
Tutt, A. et al. (Jul. 1, 1991). "Trispecific F(ab')3 Derivatives that use Cooperative Signaling via the TCR/CD3 Complex and CD2 to Activate and Redirect Resting Cytotoxic T Cells," J. Immunol. 147(1):60-69.
UniProtKB/Swiss-Prot Accession No. Q9NZQ7.1, 15 pages.
Urlaub, G. et al. (Jul. 1980). "Isolation of Chinese Hamster Cell Mutants Deficient in Dihydrofolate Reductase Activity," Proc. Natl. Acad. Sci. USA 77(7):4216-4220.

(56) References Cited

OTHER PUBLICATIONS

Van Den Berg, J.A. et al. (Feb. 1990). "Kluyveromyces as a Host for Heterologous Gene Expression: Expression and Secretion of Prochymosin," Bio/Technology 8:135-139.
Van Dijk, M.A. et al. (2001). "Human Antibodies as Next Generation Therapeutics," Curr. Opin. Pharmacol 5:368-374.
Van Warmerdam, L.J. et al. (1995). "The Use of the Calvert Formula to Determine the Optimal Carboplatin Dosage," J. Cancer Res. Clin. Oncol. 121(8):478-486.
Vaswani, S.K. et al. (Aug. 1998). "Humanized Antibodies as Potential Therapeutic Drugs," Ann. Allergy, Asthma & Immunol. 1:105-115.
Velcheti, V. et al. (May 20, 2018). "Prospective Clinical Evaluation of Blood-Based Tumor Mutational Burden (bTMB) as a Predictive Biomarker for Atexolizumab (atezo) in 1L Non-Small Cell Lung Cancer (NSCLC): Interim B-F1RST Results," J. Clinical Oncology 36(15 Suppl.):12001, Abstract Only, 4 pages.
Vollmers, H.P. et al. (2005). "Death by Stress: Natural IgM-Induced Apoptosis," Methods and Findings in Experimental and Clinical Pharmacology 27(3):185-191.
Vollmers, H.P. et al. (2005). "The "Early Birds": Natural IgM Antibodies and Immune Surveillance," Histology and Histopathology 20(3):927-937.
Winter, G. et al. (1994). "Making Antibodies by Phage Display Technology," Ann. Rev. Immunol. 12:433-455.
Wolchok, J.D. et al. (Dec. 1, 2009, e-pub. Nov. 24, 2009). "Guidelines for The Evaluation of Immune Therapy Activity in Solid Tumors: Immune-Related Response Criteria," Clin. Can. Res. 15(23):7412-7420.
Wright, A. et al. (Jan. 1997). "Effect of Glycosylation on Antibody Function: Implications for Genetics Engineering," Trends Biotechnol. 15:26-32.
Xu, J.L. et al. (Jul. 2000). "Diversity in the CDR3 Region of VH is Sufficient for Most Antibody Specificities," Immunity 13:37-45.
Yamada, A. et al. (Jan. 2013, e-pub. Dec. 4, 2012). "Next-generation Peptide Vaccines for Advanced Cancer," Cancer Sci. 104(1):15-21.
Yamane-Ohnuki, N. et al. (Sep. 5, 2004, e-pub. Aug. 6, 2004). "Establishment of FUT8 Knockout Chinese hamster Ovary Cells: An Ideal Host Cell Line for Producing Completely Defucosylated Antibodies With Enhances Antibody-Dependent Cellular Cytotoxicity," Biotech. Bioeng. 87(5):614-622.
Yazaki, P.J. et al. (2003). "Expression of Recombinant Antibodies in Mammalian Cell Lines," Methods in Molecular Biology 248:255-268.
Yilmaz, U. et al. (Oct.-Dec. 2011). "Carboplatin Plus Etoposide for Extensive Stage Small-Cell Lung Cancer: An Experience with AUC 6 Doses of Carboplatin," Indian Journal of Cancer 48(4):454-459.
Yip, D. et al. (Jun. 2000). "Predictive and Prognostic Factors in Small Cell Lung Cancer: Current Status," Lung Cancer 28(3):173-185.
Zamyatnin, A.A. (1972). "Protein Volume in Solution," Prog. Biophys. Mol. Biol. 24:107-123.
Zapata, G. et al. (1995). "Engineering Linear F(ab')2 Fragments for Efficient Production in *Escherichia coli* and Enhanced Antiproliferative Activity," Protein Eng. 8(10):1057-1062.
"FDA Approves Genentech's Tecentriq in Combination With Chemotherapy for the Initial Treatment of Adults With Extensive-Stage Small Cell Lung Cancer," Drugs.com. dated Mar. 18, 2019, retrieved from: <https://www.drugs.com/newdrugs/fda-approves-genentechs-tecentriq-combination-chemotherapy-initial-adults-extensive-stage-small-4932.html> (6 pages).
"TECENTRIQ® (atezolizumab) injection, for intravenous use Initial U.S. Approval: 2016," <https://www.accessdata.fda.gov/spl/data/f4fe4626-4d6c-4c50-9d52-51aae17f27d6/f4fe4626-4d6c-4c50-9d52-51aae17f27d6.xml>, revised Nov. 11, 2024 (58 pages).
"TECENTRIQ® (atezolizumab) injection, for intravenous use Initial U.S. Approval: 2016," <https://www.accessdata.fda.gov/drugsatfda_docs/label/2016/761041s000lbl.pdf>, dated Oct. 27, 2016 (23 pages).
"TECENTRIQ® (atezolizumab) injection, for intravenous use Initial U.S. Approval: 2016," <https://www.accessdata.fda.gov/drugsatfda_docs/label/2017/761034s001lbl.pdf> , dated Apr. 2017 (27 pages).
"TECENTRIQTM (atezolizumab) injection, for intravenous use Initial U.S. Approval: 2016," <https://www.accessdata.fda.gov/drugsatfda_docs/label/2016/761034s000lbl.pdf>, dated May 24, 2016 (17 pages).
Armstrong et al., "Immune Checkpoint Inhibitors in Small Cell Lung Cancer: A Partially Realized Potential," Adv Ther. 36:1826-32 (Jun. 2019) (7 pages).
Byers et al., "Small Cell Lung Cancer: Where Do We Go From Here?" Cancer. 121(5):664-72 (Mar. 2015).
Farago et al., "Current standards for clinical management of small cell lung cancer," Transl Lung Cancer Res. 7(1):69-79 (Jan. 2018) (11 pages).
Gadgeel et al., "1296O: Clinical efficacy of atezolizumab (Atezo) in PD-L1 subgroups defined by SP142 and 22C3 Ihc assays in 2L+ NSCLC: Results from the randomized OAK study," Ann Oncol. 28(Supplement 5):v460-1 (Sep. 2017) (Abstract only) (2 pages).
Gadgeel et al., "Phase II Study of Maintenance Pembrolizumab in Patients with Extensive-Stage Small Cell Lung Cancer (SCLC)," J Thorac Oncol. 13(9):1393-99 (May 2018) (7 pages).
Horn et al., "First-Line Atezolizumab plus Chemotherapy in Extensive-Stage Small-Cell Lung Cancer," NEJM. 379(23):2220-9 (Sep. 2018) (10 pages).
Jean et al., "Atezolizumab: feasible second-line therapy for patients with non-small cell lung cancer? A review of efficacy, safety and place in therapy," Therapeutic Advances in Medical Oncology. 9(12):769-79 (Dec. 2017).
Leal, "Evidence Builds for Immunotherapy Combos in SCLC," Oncology Live, <https://www.onclive.com/view/evidence-builds-for-immunotherapy-combos-in-sclc> , dated Jan. 10, 2018, retrieved on May 14, 2025 (4 pages).
Liu, "IMpower133: Finally Moving the Needle in SCLC," IASLC Lung Cancer News. dated Mar. 1, 2019, retrieved from: <https://www.ilcn.org/impower133-finally-moving-the-needle-in-sclc/> (3 pages).
Narozniak, "Immunotherapies, Novel Agents Push Envelope in SCLC," Oncology Live, <https://www.onclive.com/view/immunotherapies-novel-agents-push-envelope-in-sclc>, dated Oct. 23, 2019, retrieved on May 31, 2025 (13 pages).
Reck et al., "Five-year survival in patients with extensive-stage small cell lung cancer treated with atezolizumab in the Phase III IMpower133 study and the Phase III IMbrella A extension study," Lung Cancer. 196:107924 (Oct. 2024) (5 pages).
Reck et al., "Phase III Randomized Trial of Ipilimumab Plus Etoposide and Platinum Versus Placebo Plus Etoposide and Platinum in Extensive-Stage Small-Cell Lung Cancer," J Clin Oncol. 34(31):3740-8 (Jul. 2016) (20 pages).
Rudin, "Looking Ahead to New Therapies in Small Cell Lung Cancer," Clin Adv Hematol Oncol. 16(4):269-72 (Apr. 2018).
Sequist et al., "1425PD: Clinical activity, safety and predictive biomarkers results from a phase la atezolizumab (atezo) trial in extensive-stage small cell lung cancer (ES-SCLC)," Ann Oncol. 27(Supplement 6):vi493 (Oct. 2016) (Abstract only) (1 page).
Byers et al. "Proteomic profiling identifies dysregulated pathways in small cell lung cancer and novel therapeutic target including PARP1," Cancer Discovery. 2(9): 798-811 (Sep. 2012).
Cohen et al,. "FDA Drug Approval Summary: Bevacizumab (Avastin) Plus Carboplatin and Paclitaxel as First-Line Treatment of Advanced/Metastatic Recurrent Nonsquamous Non-Small Cell Lung Cancer," The Oncologist. 12(6): 713-8. (Jun. 2007).
Dayen et al., "New insights into stage and prognosis in small cell lung cancer: an analysis of 968 cases," J Thorac Dis. 9(12):5101-5111 (Dec. 2017).
Georgetown Press Release, "Georgetown-Led Study Leads to First FDA-Approved Drug in Decades to Improve Survival in Small Cell Lung Cancer," MedStar Health. (Mar. 18, 2019) (3 pages).
Hoffmann-La Roche, "A Study of Carboplatin Plus Etoposide With or Without Atezolizumab in Participants With Untreated Extensive-Stage (ES) Small Cell Lung Cancer (SCLC) (IMpower133)", ClinicalTrials.gov, NCT02763579, V28, Jun. 18, 2018 (Jun. 18, 2018) (35 pages).

(56) References Cited

OTHER PUBLICATIONS

Kim et al., "Real-world evaluation of atezolizumab and etoposide-carboplatin as a first-line treatment for extensive-stage small cell lung cancer," Korean J Intern Med. 38(2):218-225 (Mar. 2023).
Liu et al., "Updated overall survival and PD-L1 subgroup analysis of patients with extensive-stage small-cell lung cancer treated with Atezolizumab, Carboplatin, and Etoposide (IMpower 133)," J Clin Oncol. 39(6): 619-30. (Jan. 2021).
"NCCN Clinical Practice Guidelines in Oncology Small Cell Lung Cancer Version 2.2020," National Comprehensive Cancer Network. (Nov. 15, 2019) (66 pages).
Oronsky et al., "What's New in Sclc? A Review," Neoplasia. 19(10):842-847 (Oct. 2017).

* cited by examiner

ECOG PS = Eastern Cooperative Oncology Group performance status; SCLC = small cell lung cancer; RECIST = Response Evaluation Criteria in Solid Tumors.

| DOR | PBO+CE (N=130) | Atezo+CE (N=121) |
| --- | --- | --- |
| Median (95% CI) month | 3.9 (3.1, 4.2) | 4.2 (4.1, 4.5) |
| No. of ongoing response, n (%) | 7 (5.4%) | 18 (14.9%) |

| Baseline Risk Factors | Total n | P n | P Events | P Median (months) | A n | A Events | A Median (months) | Hazard Ratio | 95% Wald CI |
|---|---|---|---|---|---|---|---|---|---|
| All Patients | 403 | 202 | 189 | 4.3 | 201 | 171 | 5.22 | 0.76 | (0.61, 0.94) |
| BECOG | | | | | | | | | |
| 0 | 140 | 67 | 64 | 4.34 | 73 | 64 | 4.9 | 0.84 | (0.59, 1.2) |
| 1 | 263 | 135 | 125 | 4.3 | 128 | 107 | 5.39 | 0.72 | (0.55, 0.94) |
| MBRAIN | | | | | | | | | |
| N | 368 | 184 | 171 | 4.3 | 184 | 156 | 5.32 | 0.75 | (0.6, 0.93) |
| Y | 35 | 18 | 18 | 4.37 | 17 | 15 | 4.21 | 0.98 | (0.48, 2) |
| MLIVER | | | | | | | | | |
| N | 278 | 143 | 133 | 4.44 | 135 | 112 | 5.45 | 0.7 | (0.54, 0.91) |
| Y | 125 | 59 | 56 | 4.14 | 66 | 59 | 4.3 | 0.87 | (0.6, 1.26) |
| SEX | | | | | | | | | |
| F | 142 | 70 | 66 | 4.24 | 72 | 59 | 5.62 | 0.59 | (0.41, 0.85) |
| M | 261 | 132 | 123 | 4.4 | 129 | 112 | 4.37 | 0.87 | (0.67, 1.13) |
| AGE65 | | | | | | | | | |
| < 65 | 217 | 106 | 98 | 4.27 | 111 | 93 | 5.13 | 0.76 | (0.57, 1.01) |
| > = 65 | 186 | 96 | 91 | 4.65 | 90 | 78 | 5.32 | 0.76 | (0.56, 1.04) |

Population
No. of Patients (%)
Median Progression-Free Survival (mo)
Atezolizumab Group
Placebo Group
Hazard ratio (95% CI)
Male 261 (65%) 4.4 4.4 0.87 (0.67, 1.13)
Female 142 (35%) 5.6 4.2 0.59 (0.41, 0.85)
< 65 years 217 (54%) 5.1 4.3 0.76 (0.57, 1.01)
≥ 65 years 186 (46%) 5.3 4.6 0.76 (0.56, 1.03)
ECOG PS 0 140 (35%) 4.9 4.3 0.84 (0.59, 1.20)
ECOG PS 1 263 (65%) 5.4 4.3 0.72 (0.55, 0.94)
Brain metastases 35 (9%) 4.2 4.4 0.98 (0.49, 2.00)
No brain metastases 368 (91%) 5.3 4.3 0.75 (0.60, 0.93)
Liver metastases 149 (37%) 4.3 4.2 0.80 (0.57, 1.13)
No liver metastases 254 (63%) 5.6 4.4 0.72 (0.55, 0.94)
bTMB <10 139 (34%) 4.3 4.2 0.78 (0.54, 1.12)
bTMB ≥ 10 212 (53%) 5.5 4.4 0.69 (0.52, 0.93)
bTMB < 16 271 (67%) 5.2 4.3 0.73 (0.56, 0.94)
bTMB ≥ 16 80 (20%) 5.6 4.3 0.68 (0.43, 1.10)
ITT 403 (100%) 5.2 4.3 0.77 (0.62, 0.96)
0
0.5
1
1.5
2
2.5
Atezolizumab Better
Placebo Better PBO+CE (N=40) vs Atezo+CE (N=40)

Median: 11.9 vs 17.8

Unstratified p: 0.1306

Unstratified HR: 0.633 (0.349, 1.151)

PBO+CE (N=138) vs Atezo+CE (N=133)
Median: 9.9 vs 12.5
Unstratified p: 0.0346
Unstratified HR: 0.714 (0.521, 0.978)

bTMB > = 16

PBO+CE (N=110) vs Atezo+CE (N=102)
Median: 11.2 vs 14.6
Unstratified p: 0.0341
Unstratified HR: 0.675 (0.468, 0.973)

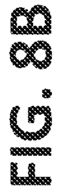
FIG. 8B
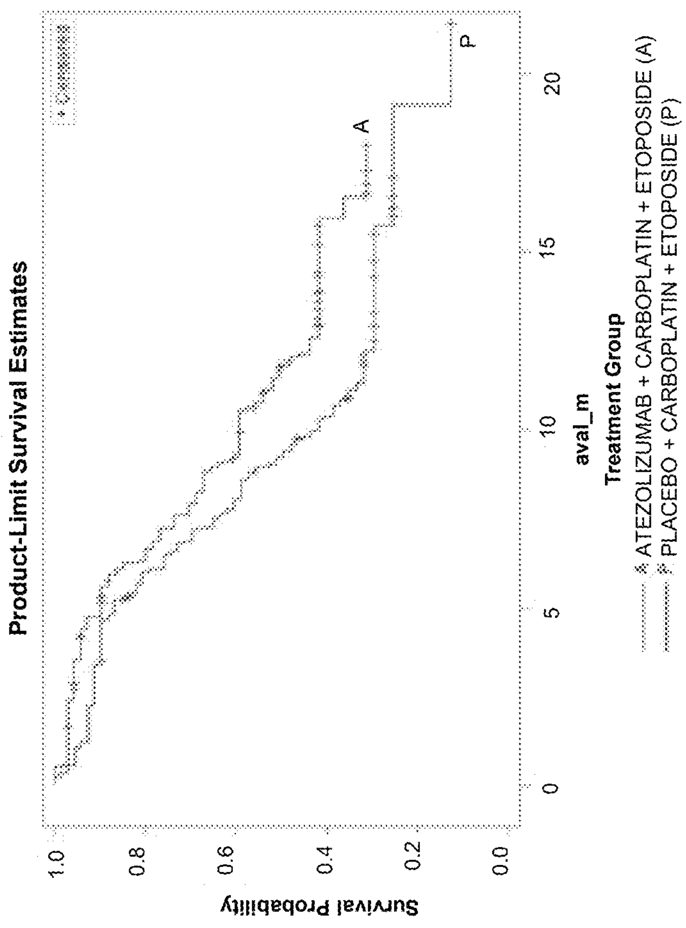
PBO+CE (N=68) vs Atezo+CE (N=71)
Median: 9.2 vs 11.8
Unstratified p: 0.0995
Unstratified HR: 0.696 (0.451, 1.074)
bTMB > = 10

PBO+CE (N=40) vs Atezo+CE (N=40)
Median: 4.3 vs 5.6
Unstratified p: 0.1145
Unstratified HR: 0.684 (0.426, 1.099)

bTMB > = 16

PBO+CE (N=138) vs Atezo+CE (N=133)
Median: 4.3 vs 5.2
Unstratified p: 0.0151
Unstratified HR: 0.728 (0.563, 0.941)

bTMB > = 16 bTMB > = 10

PBO+CE (N=110) vs Atezo+CE (N=102)
Median: 4.4 vs 5.5
Unstratified p: 0.0128
Unstratified HR: 0.693 (0.518, 0.926)

bTMB > = 10

PBO+CE (N=68) vs Atezo+CE (N=70)
Median: 4.2 vs 4.3
Unstratified p: 0.1710
Unstratified HR: 0.778 (0.543, 1.115)

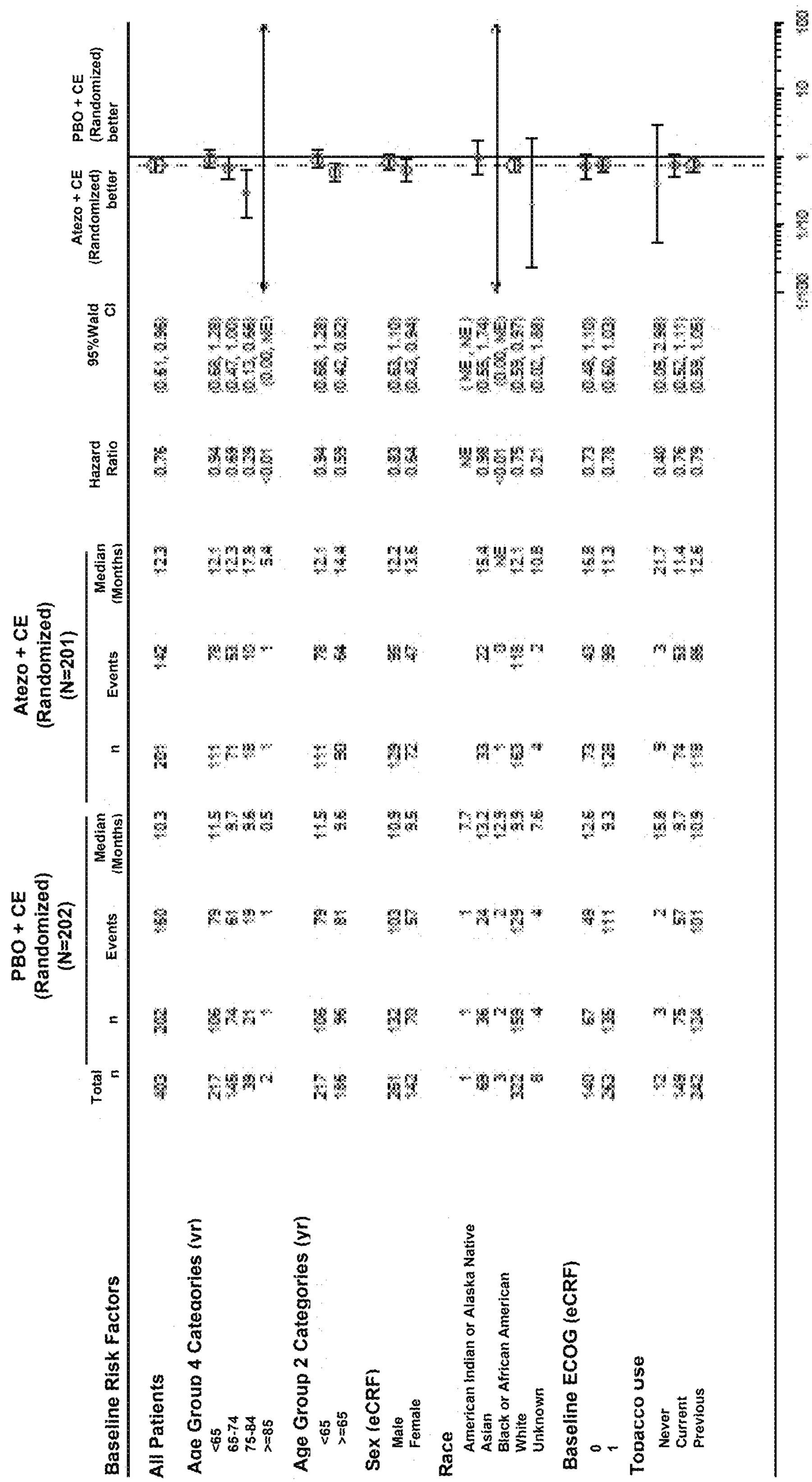
FIG. 11A
PBO + CE (Randomized) (N=202)
Atezo + CE (Randomized) (N=201)
Baseline Risk Factors
Total n
n
Events
Median (Months)
n
Events
Median (Months)
Hazard Ratio
95%Wald CI
Atezo + CE (Randomized) better
PBO + CE (Randomized) better
All Patients 403 202 160 10.3 201 142 12.3 0.76 (0.61, 0.96)
Age Group 4 Categories (yr)
<65 217 106 79 11.5 111 78 12.1 0.94 (0.68, 1.28)
65-74 145 74 61 9.7 71 53 12.3 0.69 (0.47, 1.00)
75-84 39 21 19 9.6 18 10 17.9 0.29 (0.13, 0.66)
>=85 2 1 1 0.5 1 1 5.4 <0.01 (0.00, NE)
Age Group 2 Categories (yr)
<65 217 106 79 11.5 111 78 12.1 0.94 (0.68, 1.28)
>=65 186 96 81 9.6 90 64 14.4 0.59 (0.42, 0.82)
Sex (eCRF)
Male 261 132 103 10.9 129 95 12.2 0.83 (0.63, 1.10)
Female 142 70 57 9.5 72 47 13.6 0.64 (0.43, 0.94)
Race
American Indian or Alaska Native 1 1 1 7.7 NE (NE, NE)
Asian 69 36 24 13.2 33 22 15.4 0.98 (0.55, 1.74)
Black or African American 3 2 2 12.9 1 0 NE <0.01 (0.00, NE)
White 322 159 129 9.9 163 118 12.1 0.75 (0.59, 0.97)
Unknown 8 4 4 7.6 4 2 10.8 0.21 (0.02, 1.88)
Baseline ECOG (eCRF)
0 140 67 49 12.6 73 43 16.9 0.73 (0.48, 1.10)
1 263 135 111 9.3 128 99 11.3 0.78 (0.60, 1.02)
Tobacco use
Never 12 3 2 15.8 9 3 21.7 0.40 (0.05, 2.99)
Current 149 75 57 9.7 74 53 11.4 0.76 (0.52, 1.11)
Previous 242 124 101 10.9 118 86 12.6 0.79 (0.59, 1.06)
1/100
1/10
1
10
100

METHODS OF TREATING LUNG CANCER WITH A PD-1 AXIS BINDING ANTAGONIST, A PLATINUM AGENT, AND A TOPOISOMERASE II INHIBITOR

CROSS-REFERENCE TO RELATED APPLICATIONS

This application is a continuation application of U.S. application Ser. No. 16/449,105, filed on Jun. 21, 2019, which claims the benefit of U.S. Provisional Application No. 62/689,105, filed on Jun. 23, 2018; 62/719,461, filed on Aug. 17, 2018; and 62/736,326, filed on Sep. 25, 2018, the contents of each of which are hereby incorporated by reference in their entirety.

SEQUENCE LISTING

The instant application contains a Sequence Listing which has been submitted electronically in XML format and is hereby incorporated by reference in its entirety. Said XML copy, created Apr. 12, 2024, is named "50474-358005_Sequence_Listing_4_12_24" and is 30,122 bytes in size.

FIELD

The present disclosure relates to methods of treating cancers by administering a PD-1 axis binding antagonist (e.g., atezolizumab) in combination with a platinum agent (e.g., carboplatin) and an inhibitor of topoisomerase II (e.g., etoposide).

BACKGROUND

Lung cancer remains the leading cause of cancer deaths worldwide; it is the most common cancer in men and accounted for approximately 13% of all new cancers in 2008 (Jemal et al. (2011) *CA Cancer J. Clin* 61:69-90). In 2012, it was estimated that there were 313,000 new cases of lung cancer and 268,000 lung cancer deaths in Europe (GLOBOCAN (2012). Estimated cancer incidence: mortality and prevalence Worldwide in 2012. Available at: globocan(dot) iarc(dot)fr/Pages/fact_sheets_cancer.aspx.). Similar data from the United States estimated that there would be 221,200 new cases of lung cancer and 158,040 lung cancer deaths in 2015 (Siegel et al. (2015) *CA Cancer J Clin.* 65:5-29).

Small cell lung cancer (SCLC) accounts for approximately 13% of all lung cancer cases, and is distinguished from non-small cell lung cancer (NSCLC) by its rapid growth time and early development of metastatic disease (Govindan et al. (2006) *J Clin Oncol.* 24:4539-44). Nearly all cases of SCLC are attributable to cigarette smoking (Pesch et al. (2012) *Int J Cancer.* 131:1210-9). Patients with SCLC frequently present with symptoms of widespread metastatic disease and may experience fast clinical deterioration; therefore, there is a need for rapid treatment initiation for these patients. Poor prognostic factors for survival in patients with SCLC include extensive-stage disease, poor performance status, weight loss, and markers associated with excessive bulk of disease (e.g., lactate dehydrogenase) (Yip et al. (2000) *Lung Cancer.* 28:173-85; Foster et al. (2009) Cancer. 115:2721-31.

Patients with limited-stage SCLC can be treated with chemotherapy and radiation with the potential for long-term survival (Stinchcombe et al. (2010) *Oncologist.* 15:187-95). However, the majority (approximately 70%) of patients with SCLC are diagnosed with extensive-stage disease (ES-SCLC), which has poor survival prospects (median overall survival [OS] approximately 10 months) (Socinski et al. (2009). *J Clin Oncol.* 27:4787-92.). Chest pain, dyspnea, and cough are among the most frequent disease-related symptoms experienced by patients with lung cancer. Chemotherapy alone can palliate symptoms and prolong survival for patients with ES-SCLC, however long-term survival is rare (Johnson et al. (2004) *Hematol Oncol Clin North Am.* 18:309-22; Demedts et al. (2010) *Eur Respir J.* 35:202-15).

The five-year relative survival rate for people with stage I SCLC is approximately 31%, however, at stage IV, the five-year relative survival rate declines to approximately 2% (American Cancer Society; Small Cell Lung Cancer Survival Rates, by Stage: www(dot)cancer(dot)org/cancer/small-cell-lung-cancer/detection-diagnosis-staging/survival-rates(dot)html. Accessed June 2018). Accordingly, there is a need in the art for methods of treating lung cancer, e.g., methods that extend survival rate.

All references cited herein, including patent applications, patent publications, and UniProtKB/Swiss-Prot Accession numbers are herein incorporated by reference in their entirety, as if each individual reference were specifically and individually indicated to be incorporated by reference.

SUMMARY

Provided herein are methods and uses of an anti-PD-L1 antibody for treating lung cancer patients. In particular, the methods and uses are based on data from a randomized Phase III clinical study of atezolizumab (TECETRIQ®) in combination with carboplatin and etoposide in individuals with previously-untreated extensive-stage small cell lung cancer (ES-SCLC). The study demonstrated that initial (first-line) treatment with the combination of TECENTRIQ® (atezolizumab) plus chemotherapy (carboplatin and etoposide) helped people with extensive-stage small cell lung cancer (ES-SCLC) live significantly longer compared to chemotherapy alone. The TECENTRIQ-based combination also reduced the risk of disease worsening or death (PFS) compared to chemotherapy alone. Safety for the TECENTRIQ and chemotherapy combination appeared consistent with the known safety profile of the individual medicines, and no new safety signals were identified with the combination.

In one aspect, provided herein are methods of treating an individual having lung cancer, comprising administering to the individual an effective amount of an anti-PD-L1 antibody, a platinum agent, and a topoisomerase II inhibitor, wherein the treatment extends progression free survival (PFS) of the individual. In some embodiments, the treatment extends overall survival (OS) of the individual.

In another aspect, provided herein are methods of treating an individual having lung cancer, comprising administering to the individual an effective amount of an anti-PD-L1 antibody, a platinum agent, and a topoisomerase II inhibitor, wherein the treatment extends overall survival (OS) of the individual (e.g., by at least about any one of 0.5, 1, 1.25, 1.5, 1.75, 2, 2.25, 2.5, 2.75, or 3 months) as compared to an individual having lung cancer who received treatment with a platinum agent and a topoisomerase II inhibitor. In some embodiments, the treatment extends OS, e.g., by at least about any one of 10.5, 10.75, 11, 11.25, 11.5, 11.75, 12, 12.25, 12.5, 12.75, 13, 13.25, 13.5, 13.75, or 14 months. In some embodiments, the treatment extends OS by greater than 14 months, e.g., by about any one of 14.25, 14.5, 14.75, 15, 15.25, 15.5, 15.75 or more than 15.75 months. In some embodiments, the treatment extends OS by about 15.9 months.

In some embodiments, the treatment extends the PFS of the individual by at least about 5 months. In some embodiments, the treatment extends the PFS of the individual by at least about 5.2 months. In some embodiments, the treatment extends the PFS of the individual by at least about 5.5 months. In some embodiments, the treatment extends the PFS of the individual by at least about 5.6 months. In some embodiments, the treatment extends the PFS of the individual by at least about 6 months. In some embodiment, the treatment extends the OS of the individual is extended by at least about 11 months. In some embodiment, the treatment extends the OS of the individual is extended by at least about 11.5 months. In some embodiment, the treatment extends the OS of the individual is extended by at least about 12 months. In some embodiment, the treatment extends the OS of the individual is extended by at least about 12.3 months.

In some embodiments, the anti-PD-L1 antibody comprises: (a) a heavy chain variable region ($V_H$) that comprises an HVR-H1 comprising an amino acid sequence of GFTFSDSWIH (SEQ ID NO:1), an HVR-2 comprising an amino acid sequence of AWISPYGGSTYYADSVKG (SEQ ID NO:2), and HVR-3 comprising an amino acid RHWPGGFDY (SEQ ID NO:3), and (b) a light chain variable region ($V_L$) that comprises an HVR-L1 comprising an amino acid sequence of RASQDVSTAVA (SEQ ID NO:4), an HVR-L2 comprising an amino acid sequence of SASFLYS (SEQ ID NO:5), and an HVR-L3 comprising an amino acid sequence of QQYLYHPAT (SEQ ID NO:6). In some embodiments, the anti-PD-L1 antibody comprises a heavy chain variable region ($V_H$) comprising an amino acid sequence of SEQ ID NO: 7 and a light chain variable region ($V_L$) comprising an amino acid sequence of SEQ ID NO: 8. In some embodiments, the anti-PD-L1 antibody is atezolizumab.

In some embodiments, the platinum agent is carboplatin or cisplatin. In some embodiments, the platinum agent is carboplatin. In some embodiments, the topoisomerase II inhibitor is etoposide, teniposide, doxorubicin, daunorubicin, mitoxantrone, amsacrine, an ellipticine, aurintricarboxylic acid, or HU-331. In some embodiments, the topoisomerase inhibitor is etoposide. In some embodiments, the platinum agent is carboplatin and the topoisomerase II inhibitor is etoposide.

In some embodiments, the anti-PD-L1 antibody is administered at a dose of 1200 mg, the platinum agent is administered at a dose sufficient to achieve AUC=5 mg/ml/min, and the topoisomerase II inhibitor is administered at a dose of 100 mg/m$^2$. In some embodiments, the anti-PD-L1 antibody, the platinum agent, and the topoisomerase II inhibitor are administered in four 21-day Cycles, and wherein the anti-PD-L1 antibody is administered at a dose of 1200 mg on Day 1, the platinum agent is administered at a dose sufficient to achieve AUC=5 mg/ml/min on Day 1, and the topoisomerase II inhibitor is administered at a dose of 100 mg/m$^2$ on each of Days 1, 2, and 3 of each 21-day cycle for Cycles 1-4. In some embodiments, the anti-PD-L1 antibody is further administered following Cycle 4, and wherein the anti-PD-L1 antibody is administered at a dose of 1200 mg on Day 1 of each 21-day cycle for every cycle after Cycle 4. In some embodiments, the anti-PD-L1 antibody, the platinum agent, and the topoisomerase II inhibitor are administered sequentially on Day 1 of Cycles 1-4. In some embodiments, the anti-PD-L1 antibody is administered prior to the platinum agent, and wherein the platinum agent is administered prior to the topoisomerase II inhibitor on Day 1 of Cycles 1-4.

In some embodiments, the lung cancer is small cell lung cancer (SCLC). In some embodiments, the SCLC is extensive stage SCLC (ES-SCLC). In some embodiments, the individual is treatment-naïve for ES-SCLC. In some embodiments, the individual has a blood tumor mutational burden (bTMB) of at least about 10. In some embodiments, the individual has a bTMB of at least about 16. In some embodiments, the lung cancer has metastasized to the brain. In some embodiments, the lung cancer has metastasized to the liver. In some embodiments, the lung cancer has metastasized to the adrenal gland. In some embodiments, the lung cancer has metastasized to the lymph nodes. In some embodiments, the lung cancer has metastasized within the lung (e.g., outside of the original site of disease) or to the other lung. In some embodiments, the individual is at least 65 years old (e.g., between about 65 to about 74 years of age, between about 75 to about 84 years of age, or greater than about 85 years of age). In some embodiments, the individual is PD-L1 negative. In some embodiments, the individual is PD-L1 negative if less than 1% of the tumor cells (TC) and/or tumor-infiltrating immune cells (IC) in a sample obtained from the individual express PD-L1, e.g., according to an assay described herein.

In some embodiments, the anti-PD-L1 antibody, the platinum agent, and the topoisomerase II inhibitor are each administered intravenously.

In another aspect, provided herein are methods of treating an individual having extensive-stage small cell lung cancer (ES-SCLC), comprising administering to the individual an effective amount of atezolizumab, carboplatin, and etoposide, wherein the atezolizumab is administered at a dose of 1200 mg, the carboplatin is administered at a dose sufficient to achieve AUC=5 mg/ml/min, and the etoposide is administered at a dose of 100 mg/m$^2$, and wherein the treatment extends progression free survival (PFS) and overall survival (OS) of the individual.

In some embodiments, atezolizumab, carboplatin, and etoposide are administered in four 21-day Cycles and atezolizumab is further administered following Cycle 4, wherein atezolizumab is administered at a dose of 1200 mg on Day 1 of each 21-day cycle of Cycles 1-4, carboplatin is administered at a dose sufficient to achieve AUC=5 mg/ml/min on Day 1 of each 21-day cycle of Cycles 1-4, and etoposide is administered at a dose of 100 mg/m$^2$ on each of Days 1, 2, and 3 of each 21-day cycle for Cycles 1-4; and wherein atezolizumab is further administered at a dose of 1200 mg on Day 1 of each 21-day cycle for every cycle after Cycle 4.

In some embodiments, the treatment extends the PFS of the individual by at least about 5 months. In some embodiments, the treatment extends the PFS of the individual by at least about 5.2 months. In some embodiments, the treatment extends the PFS of the individual by at least about 5.5 months. In some embodiments, the treatment extends the PFS of the individual by at least about 5.6 months. In some embodiments, the treatment extends the PFS of the individual by at least about 6 months. In some embodiment, the treatment extends the OS of the individual is extended by at least about 11 months. In some embodiment, the treatment extends the OS of the individual is extended by at least about 11.5 months. In some embodiment, the treatment extends the OS of the individual is extended by at least about 12 months. In some embodiment, the treatment extends the OS of the individual is extended by at least about 12.3 months.

In some embodiments, the individual is treatment-naïve for ES-SCLC. In some embodiments, the individual has a blood tumor mutational burden (bTMB) of at least about 10. In some embodiments, the individual has a bTMB of at least about 16. In some embodiments, the ES-SCLC has metastasized to the brain. In some embodiments, the ES-SCLC has metastasized to the liver. In some embodiments, the individual is at least 65 years old.

In some embodiments, the atezolizumab, the carboplatin, and the etoposide are administered sequentially on Day 1 of each 21-day cycle for Cycles 1-4. In some embodiments, the atezolizumab is administered prior to the carboplatin, and wherein the carboplatin is administered prior to the etoposide on Day 1 of each 21-day cycle for Cycles 1-4. In some embodiments, the atezolizumab, the carboplatin, and the etoposide are each administered intravenously.

In some embodiments, the individual is human.

In another aspect, provided herein are kits comprising an anti-PD-L1 antibody for use in combination with a platinum agent and an topoisomerase II inhibitor for treating an individual having lung cancer according to any of the methods above and described herein. Also provided herein are kits comprising atezolizumab for use in combination with carboplatin and etoposide for treating an individual having lung cancer according to any of the methods above and described herein.

In another aspect, provided herein is an anti-PD-L1 antibody for use in a method of treating lung cancer in an individual, the method comprising administering to the individual an effective amount of an anti-PD-L1 antibody, a platinum agent, and a topoisomerase II inhibitor, wherein the treatment extends progression free survival (PFS) and/or overall survival (OS) of the individual. In some embodiments, the anti-PD-L1 antibody is for use in a method according to any of the methods above or described herein.

In another aspect, provided herein is a composition comprising atezolizumab for use in a method of treating extensive-stage small cell lung cancer (ES-SCLC), comprising administering to the individual an effective amount of atezolizumab, carboplatin, and etoposide, wherein the atezolizumab is administered at a dose of 1200 mg, the carboplatin is administered at a dose sufficient to achieve AUC=5 mg/ml/min, and the etoposide is administered at a dose of 100 $mg/m^2$, and wherein the treatment extends progression free survival (PFS) and overall survival (OS) of the individual. In some embodiments, the composition is for use in a method according to any one of the methods above or described herein.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

FIG. 8B provides a Kaplan Meier plot of overall survival of patients with a bTMB<10 in Arm A (atezolizumab+carboplatin+etoposide) vs. Arm B (placebo+carboplatin+etoposide).

FIG. 11A provides a Forest Plot showing subgroup analyses of OS in patients with various baseline risk factors in Arm A Arm A (atezolizumab+carboplatin+etoposide) vs. Arm B (placebo+carboplatin+etoposide).

DETAILED DESCRIPTION

I. Definitions

Figure 1A:
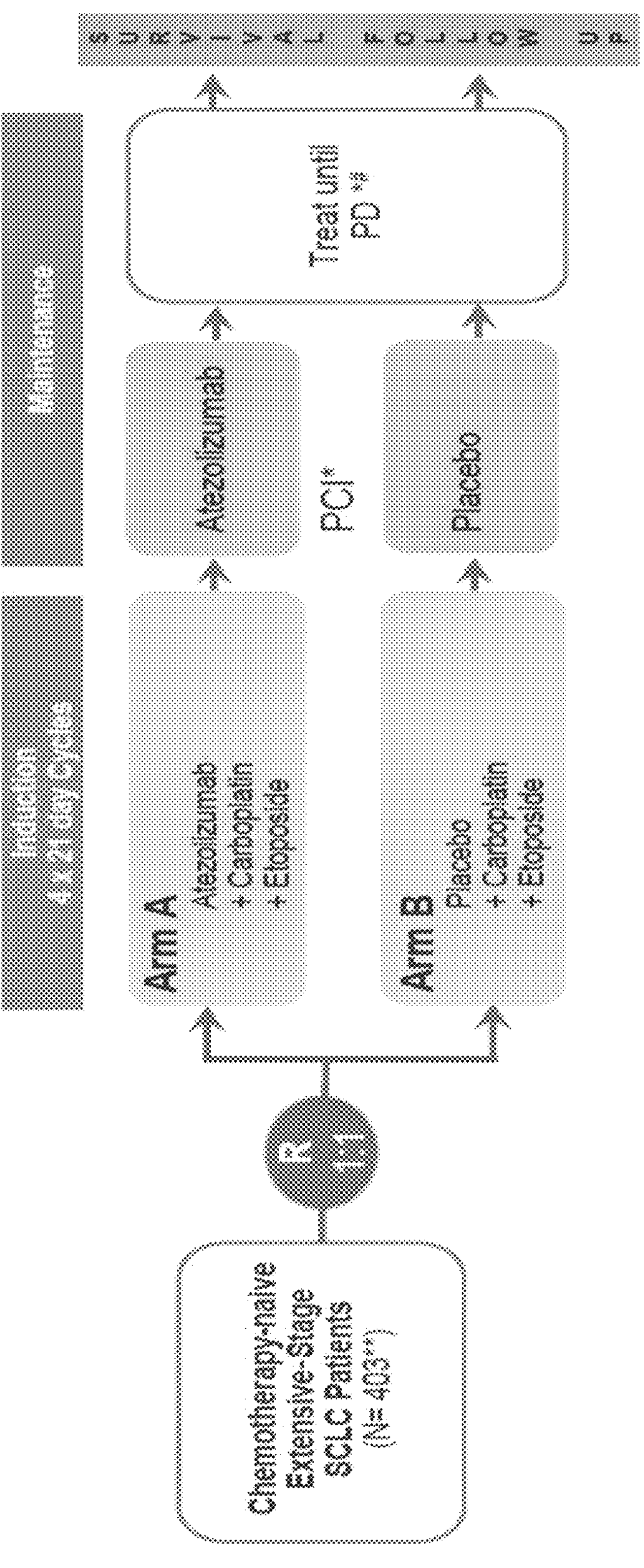
FIG. 1A provides a schematic of the study design of the clinical trial described in Example 1. Arm A included 201 patients. Arm B included 202 patients. PCI=prophylactic cranial irradiation. PD=disease progression.

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. Specific examples of PD-1 binding antagonists are provided infra.

The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. Specific examples of PD-L1 binding antagonists are provided infra.

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

"Sustained response" refers to the sustained effect on reducing tumor growth after cessation of a treatment. For example, the tumor size may remain to be the same or smaller as compared to the size at the beginning of the administration phase. In some embodiments, the sustained response has a duration at least the same as the treatment duration, at least 1.5×, 2.0×, 2.5×, or 3.0× length of the treatment duration.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile. "Pharmaceutically acceptable" excipients (vehicles, additives) are those which can reasonably be administered to a subject mammal to provide an effective dose of the active ingredient employed.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. For example, an individual is successfully "treated" if one or more symptoms associated with cancer are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, and/or prolonging survival of individuals.

As used herein, "delaying progression of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

An "effective amount" is at least the minimum amount required to effect a measurable improvement or prevention of a particular disorder. An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "in conjunction with" refers to administration of one treatment modality in addition to another treatment modality. As such, "in conjunction with" refers to administration of one treatment modality before, during, or after administration of the other treatment modality to the individual.

A "disorder" is any condition that would benefit from treatment including, but not limited to, chronic and acute disorders or diseases including those pathological conditions which predispose the mammal to the disorder in question.

The terms "cell proliferative disorder" and "proliferative disorder" refer to disorders that are associated with some degree of abnormal cell proliferation. In one embodiment, the cell proliferative disorder is cancer. In one embodiment, the cell proliferative disorder is a tumor.

"Tumor," as used herein, refers to all neoplastic cell growth and proliferation, whether malignant or benign, and all pre-cancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. More particular examples of such cancers include, but not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDSrelated lymphoma; and Waldenstrom's Macroglobulinemia); chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In certain embodiments, cancers that are amenable to treatment by the antibodies of the invention include breast cancer, colorectal cancer, rectal cancer, non-small cell lung cancer, glioblastoma, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, ovarian cancer, mesothelioma, and multiple myeloma. In some embodiments, the cancer is selected from: small cell lung cancer, glioblastoma, neuroblastomas, melanoma, breast carcinoma, gastric cancer, colorectal cancer (CRC), and hepatocellular carcinoma.

The term "cytotoxic agent" as used herein refers to any agent that is detrimental to cells (e.g., causes cell death, inhibits proliferation, or otherwise hinders a cellular function). Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof. Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signalling inhibitors, HDAC inhibitors, proteasome inhibitors, and inhibitors of cancer metabolism. In one embodiment the cytotoxic agent is a taxane. In one embodiment the taxane is paclitaxel or docetaxel. In one embodiment the cytotoxic agent is a platinum agent. In one embodiment the cytotoxic agent is an antagonist of EGFR. In one embodiment the antagonist of EGFR is N-(3-ethynylphenyl)-6,7-bis(2-methoxyethoxy) quinazolin-4-amine (e.g., erlotinib). In one embodiment the cytotoxic agent is a RAF inhibitor. In one embodiment, the RAF inhibitor is a BRAF and/or CRAF inhibitor. In one embodiment the RAF inhibitor is vemurafenib. In one embodiment the cytotoxic agent is a PI3K inhibitor.

"Chemotherapeutic agent" includes compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4 (5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length $IgG_1$ λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. *Eur. J. Cancer* 32A: 636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., *J. Biol. Chem.* 279 (29): 30375-30384 (2004)). The anti-EGFR antibody may be conjugated with a cytotoxic agent, thus generating an immunoconjugate (see, e.g., EP659439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy) quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl) methoxy]phenyl]-6[5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino) phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $p^{32}$, $Pb^{212}$ and radioactive isotopes of Lu); miscellaneous investigational agents such as thioplatin, PS-341, phenylbutyrate, ET-18- $OCH_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

A "growth inhibitory agent" when used herein refers to a compound or composition which inhibits growth of a cell either in vitro or in vivo. In one embodiment, growth inhibitory agent is growth inhibitory antibody that prevents or reduces proliferation of a cell expressing an antigen to which the antibody binds. In another embodiment, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

A "subject" or an "individual" for purposes of treatment refers to any animal classified as a mammal, including humans, domestic and farm animals, and zoo, sports, or pet animals, such as dogs, horses, cats, cows, etc. Preferably, the mammal is human.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The term "constant domain" refers to the portion of an immunoglobulin molecule having a more conserved amino acid sequence relative to the other portion of the immunoglobulin, the variable domain, which contains the antigen binding site. The constant domain contains the $C_H1$, $C_H2$ and $C_H3$ domains (collectively, CH) of the heavy chain and the CHL (or CL) domain of the light chain.

The "variable region" or "variable domain" of an antibody refers to the amino-terminal domains of the heavy or light chain of the antibody. The variable domain of the heavy chain may be referred to as "$V_H$." The variable domain of the light chain may be referred to as "$V_L$." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any mammalian species can be assigned to one of two clearly distinct types, called kappa ("K") and lambda ("λ"), based on the amino acid sequences of their constant domains.

The term IgG "isotype" or "subclass" as used herein is meant any of the subclasses of immunoglobulins defined by the chemical and antigenic characteristics of their constant regions.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, γ, ε, γ, and μ, respectively. The subunit structures and three-dimensional configurations of different classes of immunoglobulins are well known and described generally in, for example, Abbas et al. *Cellular and Mol. Immunology,* 4th ed. (W.B. Saunders, Co., 2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

A "naked antibody" for the purposes herein is an antibody that is not conjugated to a cytotoxic moiety or radiolabel.

"Antibody fragments" comprise a portion of an intact antibody, preferably comprising the antigen binding region thereof. In some embodiments, the antibody fragment described herein is an antigen-binding fragment. Examples of antibody fragments include Fab, Fab', $F(ab')_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90:6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by a variety of techniques, including, for example, the hybridoma method (e.g., Kohler and Milstein, *Nature,* 256:495-97 (1975); Hongo et al., *Hybridoma,* 14 (3): 253-260 (1995), Harlow et al., *Antibodies: A Laboratory Manual*, (Cold Spring Harbor Laboratory Press, 2nd ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., *Nature,* 352:624-628 (1991); Marks et al., *J. Mol. Biol.* 222:581-597 (1992); Sidhu et al., *J. Mol. Biol.* 338 (2): 299-310 (2004); Lee et al., *J. Mol. Biol.* 340 (5): 1073-1093 (2004); Fellouse, *Proc. Natl. Acad. Sci. USA* 101 (34): 12467-12472 (2004); and Lee et al., *J. Immunol. Methods* 284 (1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90:2551 (1993); Jakobovits et al., *Nature* 362:255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10:779-783 (1992); Lonberg et al., *Nature* 368:856-859 (1994); Morrison, *Nature* 368:812-813 (1994); Fishwild et al., *Nature Biotechnol.* 14:845-851 (1996); *Neuberger, Nature Biotechnol.* 14:826 (1996); and Lonberg and Huszar, *Intern. Rev. Immunol.* 13:65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., *Proc. Natl. Acad. Sci. USA* 81:6851-6855 (1984)). Chimeric antibodies include PRIMATTZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, e.g., Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227:381 (1991); Marks et al., *J. Mol. Biol.,* 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.,* 147 (1): 86-95 (1991). See also van Dijk and van de Winkel, *Curr. Opin. Pharmacol.,* 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA,* 103:3557-3562 (2006) regarding human antibodies generated via a human B-cell hybridoma technology.

A "species-dependent antibody" is one which has a stronger binding affinity for an antigen from a first mammalian species than it has for a homologue of that antigen from a second mammalian species. Normally, the species-dependent antibody "binds specifically" to a human antigen (e.g., has a binding affinity (Kd) value of no more than about $1\times10^{-7}$ M, preferably no more than about $1\times10^{-8}$ M and preferably no more than about $1\times10^{-9}$ M) but has a binding affinity for a homologue of the antigen from a second nonhuman mammalian species which is at least about 50 fold, or at least about 500 fold, or at least about 1000 fold, weaker than its binding affinity for the human antigen. The species-dependent antibody can be any of the various types of antibodies as defined above, but preferably is a humanized or human antibody.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., *Sequences of Immunological Interest.* 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

The expression "linear antibodies" refers to the antibodies described in Zapata et al. (1995 *Protein Eng,* 8 (10): 1057-1062). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

As use herein, the term "binds", "specifically binds to" or is "specific for" refers to measurable and reproducible interactions such as binding between a target and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 μM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

The term "sample," as used herein, refers to a composition that is obtained or derived from a subject and/or individual of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized. Samples include, but are not limited to, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebro-spinal fluid, saliva, sputum, tears, perspiration, mucus, tumor lysates, and tissue culture medium, tissue extracts such as homogenized tissue, tumor tissue, cellular extracts, and combinations thereof.

By "tissue sample" or "cell sample" is meant a collection of similar cells obtained from a tissue of a subject or individual. The source of the tissue or cell sample may be solid tissue as from a fresh, frozen and/or preserved organ, tissue sample, biopsy, and/or aspirate; blood or any blood constituents such as plasma; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

A "reference sample", "reference cell", "reference tissue", "control sample", "control cell", or "control tissue", as used herein, refers to a sample, cell, tissue, standard, or level that is used for comparison purposes. In one embodiment, a reference sample, reference cell, reference tissue, control sample, control cell, or control tissue is obtained from a healthy and/or non-diseased part of the body (e.g., tissue or cells) of the same subject or individual. For example, healthy and/or non-diseased cells or tissue adjacent to the diseased cells or tissue (e.g., cells or tissue adjacent to a tumor). In another embodiment, a reference sample is obtained from an untreated tissue and/or cell of the body of the same subject or individual. In yet another embodiment, a reference sample, reference cell, reference tissue, control sample, control cell, or control tissue is obtained from a healthy and/or non-diseased part of the body (e.g., tissues or cells) of an individual who is not the subject or individual.

In even another embodiment, a reference sample, reference cell, reference tissue, control sample, control cell, or control tissue is obtained from an untreated tissue and/or cell of the body of an individual who is not the subject or individual.

An "effective response" of a patient or a patient's "responsiveness" to treatment with a medicament and similar wording refers to the clinical or therapeutic benefit imparted to a patient at risk for, or suffering from, a disease or disorder, such as cancer. In one embodiment, such benefit includes any one or more of: extending survival (including overall survival and progression free survival); resulting in an objective response (including a complete response or a partial response); or improving signs or symptoms of cancer.

A patient who "does not have an effective response" to treatment refers to a patient who does not have any one of extending survival (including overall survival and progression free survival); resulting in an objective response (including a complete response or a partial response); or improving signs or symptoms of cancer.

A "functional Fc region" possesses an "effector function" of a native sequence Fc region. Exemplary "effector functions" include C1q binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed, for example, in definitions herein.

"Human effector cells" refer to leukocytes that express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, e.g., from blood.

A cancer or biological sample which "has human effector cells" is one which, in a diagnostic test, has human effector cells present in the sample (e.g., infiltrating human effector cells).

A cancer or biological sample which "has FcR-expressing cells" is one which, in a diagnostic test, has FcR-expressing present in the sample (e.g., infiltrating FcR-expressing cells). In some embodiments, FcR is FcγR. In some embodiments, FcR is an activating FcγR.

II. Overview

Provided herein is a method for treating or delaying progression of lung cancer (such as small cell lung cancer, e.g., extensive stage small cell lung cancer) in an individual comprising administering to the individual an effective amount of a PD-1 axis binding antagonist (e.g., an anti-PD-L1 antibody, such as atezolizumab), a platinum agent (e.g., carboplatin or cisplatin) and an inhibitor of topoisomerase II (e.g., etoposide). Also provided herein is a method of enhancing immune function in an individual having lung cancer (such as small cell lung cancer, e.g., extensive stage small cell lung cancer) comprising administering to the individual an effective amount of a PD-1 axis binding antagonist (e.g., an anti-PD-L1 antibody, such as atezolizumab), a platinum agent (e.g., carboplatin or cisplatin) and an inhibitor of topoisomerase II (e.g., etoposide). In some embodiments, the treatment extends the progression free survival (PFS) and/or the overall survival (OS) of the individual. In some embodiments, the treatment extends the progression free survival (PFS) and/or the overall survival (OS) of the individual, as compared to a treatment comprising administration of a platinum agent (e.g., carboplatin or cisplatin) and an inhibitor of topoisomerase II (e.g., etoposide).

In some embodiments, the method comprises treating an individual having extensive-stage small cell lung cancer (ES-SCLC), by administering to the individual atezolizumab in combination with carboplatin and etoposide, wherein the administering comprises and induction phase and a maintenance phase, wherein the induction phase comprises administering atezolizumab at a dose of 1200 mg on Day 1, the carboplatin at a dose sufficient to achieve AUC =5 mg/ml/min on Day 1, and the etoposide at a dose of 100 mg/$m^2$ on each of Days 1, 2, and 3 of each 21-day cycle for Cycles 1-4; and wherein the maintenance phase comprises administering the atezolizumab at a dose of 1200 mg on Day 1 of each 21-day cycle for every cycle after Cycle 4; wherein the individual is treatment-naïve for ES-SCLC; and wherein the administering extends the progression free survival (PFS) and the overall survival (OS) of the individual.

III. PD-1 Axis Binding Antagonists

For example, a PD-1 axis binding antagonist includes a PD-1 binding antagonist, a PDL1 binding antagonist and a PDL2 binding antagonist. Alternative names for "PD-1" include CD279 and SLEB2. Alternative names for "PDL1" include B7-H1, B7-4, CD274, and B7-H. Alternative names for "PDL2" include B7-DC, Btdc, and CD273. In some embodiments, PD-1, PDL1, and PDL2 are human PD-1, PDL1 and PDL2.

In some embodiments, the PD-1 binding antagonist is a molecule that inhibits the binding of PD-1 to its ligand binding partner(s). In a specific aspect the PD-1 ligand binding partners are PDL1 and/or PDL2. In another embodiment, a PDL1 binding antagonist is a molecule that inhibits the binding of PDL1 to its binding partner(s). In a specific aspect, PDL1 binding partner(s) are PD-1 and/or B7-1. In another embodiment, the PDL2 binding antagonist is a molecule that inhibits the binding of PDL2 to its binding partner(s). In a specific aspect, a PDL2 binding partner is PD-1. The antagonist may be an antibody, an antigen binding fragment thereof, an immunoadhesin, a fusion protein, or oligopeptide.

In some embodiments, the PD-1 binding antagonist is an anti-PD-1 antibody (e.g., a human antibody, a humanized antibody, or a chimeric antibody).

In some embodiments, the anti-PD-1 antibody is nivolumab (CAS Registry Number: 946414-94-4). Nivolumab (Bristol-Myers Squibb/Ono), also known as MDX-1106-04, MDX-1106, ONO-4538, BMS-936558, and OPDIVO®, is an anti-PD-1 antibody described in WO2006/121168. In some embodiments, the anti-PD-1 antibody comprises a heavy chain and a light chain sequence, wherein:

(a) the heavy chain comprises the amino acid sequence:

(SEQ ID NO: 11)

```
QVQLVESGGGVVQPGRSLRLDCKASGITFSNSGMHWVRQAPGKGLEWVAV
IWYDGSKRYYADSVKGRFTISRDNSKNTLFLQMNSLRAEDTAVYYCATND
DYWGQGTLVTVSSASTKGPSVFPLAPCSRSTSESTAALGCLVKDYFPEPV
TVSWNSGALTSGVHTFPAVLQSSGLYSLSSVVTVPSSSLGTKTYTCNVDH
KPSNTKVDKRVESKYGPPCPPCPAPEFLGGPSVFLFPPKPKDTLMISRTP
EVTCVVVDVSQEDPEVQFNWYVDGVEVHNAKTKPREEQFNSTYRVVSVLT
VLHQDWLNGKEYKCKVSNKGLPSSIEKTISKAKGQPREPQVYTLPPSQEE
MTKNQVSLTCLVKGFYPSDIAVEWESNGQPENNYKTTPPVLDSDGSFFLY
SRLTVDKSRWQEGNVFSCSVMHEALHNHYTQKSLSLSLGK,
```

and

-continued (b) the light chain comprises the amino acid sequence:

(SEQ ID NO: 12)

```
EIVLTQSPATLSLSPGERATLSCRASQSVSSYLAWYQQKPGQAPRLLIYD
ASNRATGIPARFSGSGSGTDFTLTISSLEPEDFAVYYCQQSSNWPRTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC.
```

In some embodiments, the anti-PD-1 antibody comprises the six HVR sequences from SEQ ID NO:11 and SEQ ID NO:12 (e.g., the three heavy chain HVRs from SEQ ID NO:11 and the three light chain HVRs from SEQ ID NO:12). In some embodiments, the anti-PD-1 antibody comprises the heavy chain variable domain from SEQ ID NO:11 and the light chain variable domain from SEQ ID NO:12.

In some embodiments, the anti-PD-1 antibody is pembrolizumab (CAS Registry Number: 1374853-91-4). Pembrolizumab (Merck), also known as MK-3475, Merck 3475, lambrolizumab, KEYTRUDA®, and SCH-900475, is an anti-PD-1 antibody described in WO2009/114335. In some embodiments, the anti-PD-1 antibody comprises a heavy chain and a light chain sequence, wherein:

(a)
the heavy chain comprises the amino acid sequence:

(SEQ ID NO: 13)

```
QVQLVQSGVEVKKPGASVKVSCKASGYTFTNYYMYWVRQAPGQGLEWMGG
INPSNGGTNFNEKFKNRVTLTTDSSTTTAYMELKSLQFDDTAVYYCARRD
YRFDMGFDYWGQGTTVTVSSASTKGPSVFPLAPCSRSTSESTAALGCLVK
DYFPEPVTVSWNSGALTSGVHTFPAVLQSSGLYSLSSVVTVPSSSLGTKT
YTCNVDHKPSNTKVDKRVESKYGPPCPPCPAPEFLGGPSVFLFPPKPKDT
LMISRTPEVTCVVVDVSQEDPEVQFNWYVDGVEVHNAKTKPREEQFNSTY
RVVSVLTVLHQDWLNGKEYKCKVSNKGLPSSIEKTISKAKGQPREPQVYT
LPPSQEEMTKNQVSLTCLVKGFYPSDIAVEWESNGQPENNYKTTPPVLDS
DGSFFLYSRLTVDKSRWQEGNVFSCSVMHEALHNHYTQKSLSLSLGK,
```

and (b)
the light chain comprises the amino acid sequence:

(SEQ ID NO: 14)

```
EIVLTQSPAT LSLSPGERATLSCRASKGVSTSGYSYLHWYQQKPGQAPR
LLIYLASYLESGVPARFSGSGSGTDFTLTISSLEPEDFAVYYCQHSRDLP
LTFGGGTKVEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC.
```

In some embodiments, the anti-PD-1 antibody comprises the six HVR sequences from SEQ ID NO:13 and SEQ ID NO:14 (e.g., the three heavy chain HVRs from SEQ ID NO:13 and the three light chain HVRs from SEQ ID NO:14). In some embodiments, the anti-PD-1 antibody comprises the heavy chain variable domain from SEQ ID NO:13 and the light chain variable domain from SEQ ID NO:14.

In some embodiments, the anti-PD-1 antibody is MEDI-0680 (AMP-514; AstraZeneca). MEDI-0680 is a humanized IgG4 anti-PD-1 antibody.

In some embodiments, the anti-PD-1 antibody is PDR001 (CAS Registry No. 1859072-53-9; Novartis). PDR001 is a humanized IgG4 anti-PD1 antibody that blocks the binding of PDL1 and PDL2 to PD-1.

In some embodiments, the anti-PD-1 antibody is REGN2810 (Regeneron). REGN2810 is a human anti-PD1 antibody.

In some embodiments, the anti-PD-1 antibody is BGB-108 (BeiGene). In some embodiments, the anti-PD-1 antibody is BGB-A317 (BeiGene).

In some embodiments, the anti-PD-1 antibody is JS-001 (Shanghai Junshi). JS-001 is a humanized anti-PD1 antibody.

In some embodiments, the anti-PD-1 antibody is STI-A1110 (Sorrento). STI-A1110 is a human anti-PD1 antibody.

In some embodiments, the anti-PD-1 antibody is INCSHR-1210 (Incyte). INCSHR-1210 is a human IgG4 anti-PD1 antibody.

In some embodiments, the anti-PD-1 antibody is PF-06801591 (Pfizer).

In some embodiments, the anti-PD-1 antibody is TSR-042 (also known as ANB011; Tesaro/AnaptysBio).

In some embodiments, the anti-PD-1 antibody is AM0001 (ARMO Biosciences).

In some embodiments, the anti-PD-1 antibody is ENUM 244C8 (Enumeral Biomedical Holdings). ENUM 244C8 is an anti-PD1 antibody that inhibits PD-1 function without blocking binding of PDL1 to PD-1.

In some embodiments, the anti-PD-1 antibody is ENUM 388D4 (Enumeral Biomedical Holdings). ENUM 388D4 is an anti-PD1 antibody that competitively inhibits binding of PDL1 to PD-1.

In some embodiments, the PD-1 antibody comprises the six HVR sequences (e.g., the three heavy chain HVRs and the three light chain HVRs) and/or the heavy chain variable domain and light chain variable domain from a PD-1 antibody described in WO2015/112800 (Applicant: Regeneron), WO2015/112805 (Applicant: Regeneron), WO2015/112900 (Applicant: Novartis), US20150210769 (Assigned to Novartis), WO2016/089873 (Applicant: Celgene), WO2015/035606 (Applicant: Beigene), WO2015/085847 (Applicants: Shanghai Hengrui Pharmaceutical/Jiangsu Hengrui Medicine), WO2014/206107 (Applicants: Shanghai Junshi Biosciences/Junmeng Biosciences), WO2012/145493 (Applicant: Amplimmune), U.S. Pat. No. 9,205,148 (Assigned to MedImmune), WO2015/119930 (Applicants: Pfizer/Merck), WO2015/119923 (Applicants: Pfizer/Merck), WO2016/032927 (Applicants: Pfizer/Merck), WO2014/179664 (Applicant: AnaptysBio), WO2016/106160 (Applicant: Enumeral), and WO2014/194302 (Applicant: Sorrento).

In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. AMP-224 (CAS Registry No. 1422184-00-6; GlaxoSmithKline/MedImmune), also known as B7-DCIg, is a PDL2-Fc fusion soluble receptor described in WO2010/027827 and WO2011/066342.

In some embodiments, the PD-1 binding antagonist is a peptide or small molecule compound. In some embodiments, the PD-1 binding antagonist is AUNP-12 (PierreFabre/Aurigene). See, e.g., WO2012/168944, WO2015/036927, WO2015/044900, WO2015/033303, WO2013/144704, WO2013/132317, and WO2011/161699.

In some embodiments, the PDL1 binding antagonist is a small molecule that inhibits PD-1. In some embodiments, the PDL1 binding antagonist is a small molecule that inhibits PDL1. In some embodiments, the PDL1 binding antagonist is a small molecule that inhibits PDL1 and VISTA. In some embodiments, the PDL1 binding antagonist is CA-170 (also known as AUPM-170). In some embodiments, the PDL1 binding antagonist is a small molecule that inhibits PDL1 and TIM3. In some embodiments, the small molecule is a compound described in WO2015/033301 and WO2015/033299.

In some embodiments, the PD-1 axis binding antagonist is an anti-PDL1 antibody. A variety of anti-PDL1 antibodies are contemplated and described herein. In any of the embodiments herein, the isolated anti-PDL1 antibody can bind to a human PDL1, for example a human PDL1 as shown in UniProtKB/Swiss-Prot Accession No.Q9NZQ7.1, or a variant thereof. In some embodiments, the anti-PDL1 antibody is capable of inhibiting binding between PDL1 and PD-1 and/or between PDL1 and B7-1. In some embodiments, the anti-PDL1 antibody is a monoclonal antibody. In some embodiments, the anti-PDL1 antibody is an antibody fragment selected from the group consisting of Fab, Fab'-SH, Fv, scFv, and (Fab') 2 fragments. In some embodiments, the anti-PDL1 antibody is a humanized antibody. In some embodiments, the anti-PDL1 antibody is a human antibody. Examples of anti-PDL1 antibodies useful for the methods of this invention, and methods for making thereof are described in PCT patent application WO 2010/077634 A1 and U.S. Pat. No. 8,217,149, which are incorporated herein by reference.

In some embodiments, the anti-PDL1 antibody comprises a heavy chain variable region and a light chain variable region, wherein:

```
(a) the heavy chain variable region comprises an
HVR-H1, HVR-H2, and HVR-H3 sequence of
                                    (SEQ ID NO: 1)
GFTFSDSWIH,

                                    (SEQ ID NO: 2)
AWISPYGGSTYYADSVKG
and

                                    (SEQ ID NO: 3)
RHWPGGFDY, respectively,
and

(b) the light chain variable region comprises an
HVR-L1, HVR-L2, and HVR-L3 sequence of
                                    (SEQ ID NO: 4)
RASQDVSTAVA,

                                    (SEQ ID NO: 5)
SASFLYS
and

                                    (SEQ ID NO: 6)
QQYLYHPAT, respectively.
```

In some embodiments, the anti-PDL1 antibody is MPDL3280A, also known as atezolizumab and TECENTRIQ® (CAS Registry Number: 1422185 Jun. 5). In some embodiments, the anti-PDL1 antibody comprises a heavy chain and a light chain sequence, wherein:

```
(a) the heavy chain variable region sequence
comprises the amino acid sequence:
                                    (SEQ ID NO: 7)
EVQLVESGGGLVQPGGSLRLSCAASGFTFSDSWIHWVRQAPGKGLEWVAW
ISPYGGSTYYADSVKGRFTISADTSKNTAYLQMNSLRAEDTAVYYCARRH
WPGGFDYWGQGTLVTVSS,
and
```

-continued

```
(b) the light chain variable region sequence
comprises the amino acid sequence:
                                    (SEQ ID NO: 8)
DIQMTQSPSSLSASVGDRVTITCRASQDVSTAVAWYQQKPGKAPKLLIYS
ASFLYSGVPSRFSGSGSGTDFTLTISSLQPEDFATYYCQQYLYHPATFGQ
GTKVEIKR.
```

In some embodiments, the anti-PDL1 antibody comprises a heavy chain and a light chain sequence, wherein:

```
(a) the heavy chain comprises the amino acid
sequence:
                                    (SEQ ID NO: 9)
EVQLVESGGGLVQPGGSLRLSCAASGFTFSDSWIHWVRQAPGKGLEWVAW
ISPYGGSTYYADSVKGRFTISADTSKNTAYLQMNSLRAEDTAVYYCARRH
WPGGFDYWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKD
TLMISRTPEVTCVVVDVSHEDPEVKFNWYVDGVEVHNAKTKPREEQYAST
YRVVSVLTVLHQDWLNGKEYKCKVSNKALPAPIEKTISKAKGQPREPQVY
TLPPSREEMTKNQVSLTCLVKGFYPSDIAVEWESNGQPENNYKTTPPVLD
SDGSFFLYSKLTVDKSRWQQGNVFSCSVMHEALHNHYTQKSLSLSPG,
and

(b) the light chain comprises the amino acid
sequence:
                                    (SEQ ID NO: 10)
DIQMTQSPSSLSASVGDRVTITCRASQDVSTAVAWYQQKPGKAPKLLIYS
ASFLYSGVPSRFSGSGSGTDFTLTISSLQPEDFATYYCQQYLYHPATFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC.
```

In some embodiments, the anti-PDL1 antibody is avelumab (CAS Registry Number: 1537032-82-8). Avelumab, also known as MSB0010718C, is a human monoclonal IgG1 anti-PDL1 antibody (Merck KGAA, Pfizer). In some embodiments, the anti-PDL1 antibody comprises a heavy chain and a light chain sequence, wherein:

```
(a) the heavy chain comprises the amino acid
sequence:
                                    (SEQ ID NO: 15)
EVQLLESGGGLVQPGGSLRLSCAASGFTFSSYIMMWVRQAPGKGLEWVSS
IYPSGGITFYADTVKGRFTISRDNSKNTLYLQMNSLRAEDTAVYYCARIK
LGTVTTVDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG,
and

(b) the light chain comprises the amino acid
sequence:
                                    (SEQ ID NO: 16)
QSALTQPASVSGSPGQSITISCTGTSSDVGGYNYVSWYQQHPGKAPKLMI
YDVSNRPSGVSNRFSGSKSGNTASLTISGLQAEDEADYYCSSYTSSSTRV
FGTGTKVTVLGQPKANPTVTLFPPSSEELQANKATLVCLISDFYPGAVTV
AWKADGSPVKAGVETTKPSKQSNNKYAASSYLSLTPEQWKSHRSYSCQVT
HEGSTVEKTVAPTECS.
```

In some embodiments, the anti-PDL1 antibody comprises the six HVR sequences from SEQ ID NO:15 and SEQ ID NO: 16 (e.g., the three heavy chain HVRs from SEQ ID NO:15 and the three light chain HVRs from SEQ ID NO:16). In some embodiments, the anti-PDL1 antibody comprises the heavy chain variable domain from SEQ ID NO:15 and the light chain variable domain from SEQ ID NO:16.

In some embodiments, the anti-PDL1 antibody is durvalumab (CAS Registry Number: 1428935-60-7). Durvalumab, also known as MEDI4736, is an Fc optimized human monoclonal IgG1 kappa anti-PDL1 antibody (MedImmune, AstraZeneca) described in WO2011/066389 and US2013/034559. In some embodiments, the anti-PDL1 antibody comprises a heavy chain and a light chain sequence, wherein:

```
(a) the heavy chain comprises the amino acid
sequence:
                                  (SEQ ID NO: 17)
EVQLVESGGGLVQPGGSLRLSCAASGFTFSRYWMSWVRQAPGKGLEWVAN
IKQDGSEKYYVDSVKGRFTISRDNAKNSLYLQMNSLRAEDTAVYYCAREG
GWFGELAFDYWGQGTLVTVSSASTKGPSVFPLAPSSKSTSGGTAALGCLV
KDYFPEPVTVSWNSGALTSGVHTFPAVLQSSGLYSLSSVVTVPSSSLGTQ
TYICNVNHKPSNTKVDKRVEPKSCDKTHTCPPCPAPEFEGGPSVFLFPPK
PKDTLMISRTPEVTCVVVDVSHEDPEVKFNWYVDGVEVHNAKTKPREEQY
NSTYRVVSVLTVLHQDWLNGKEYKCKVSNKALPASIEKTISKAKGQPREP
QVYTLPPSREEMTKNQVSLTCLVKGFYPSDIAVEWESNGQPENNYKTTPP
VLDSDGSFFLYSKLTVDKSRWQQGNVFSCSVMHEALHNHYTQKSLSLSP
G,
and

(b) the light chain comprises the amino acid
sequence:
                                  (SEQ ID NO: 18)
EIVLTQSPGTLSLSPGERATLSCRASQRVSSSYLAWYQQKPGQAPRLLIY
DASSRATGIPDRFSGSGSGTDFTLTISRLEPEDFAVYYCQQYGSLPWTFG
QGTKVEIKRTVAAPSVFIFPPSDEQLKSGTASVVCLLNNFYPREAKVQWK
VDNALQSGNSQESVTEQDSKDSTYSLSSTLTLSKADYEKHKVYAC
EVTHQGLSSPVTKSFNRGEC.
```

In some embodiments, the anti-PDL1 antibody comprises the six HVR sequences from SEQ ID NO:17 and SEQ ID NO:18 (e.g., the three heavy chain HVRs from SEQ ID NO:17 and the three light chain HVRs from SEQ ID NO:18). In some embodiments, the anti-PDL1 antibody comprises the heavy chain variable domain from SEQ ID NO:17 and the light chain variable domain from SEQ ID NO:18.

In some embodiments, the anti-PDL1 antibody is MDX-1105 (Bristol Myers Squibb). MDX-1105, also known as BMS-936559, is an anti-PDL1 antibody described in WO2007/005874.

In some embodiments, the anti-PDL1 antibody is LY3300054 (Eli Lilly).

In some embodiments, the anti-PDL1 antibody is STI-A1014 (Sorrento). STI-A1014 is a human anti-PDL1 antibody.

In some embodiments, the anti-PDL1 antibody is KN035 (Suzhou Alphamab). KN035 is single-domain antibody (dAB) generated from a camel phage display library.

In some embodiments, the anti-PDL1 antibody comprises a cleavable moiety or linker that, when cleaved (e.g., by a protease in the tumor microenvironment), activates an antibody antigen binding domain to allow it to bind its antigen, e.g., by removing a non-binding steric moiety. In some embodiments, the anti-PDL1 antibody is CX-072 (CytomX Therapeutics).

In some embodiments, the PDL1 antibody comprises the six HVR sequences (e.g., the three heavy chain HVRs and the three light chain HVRs) and/or the heavy chain variable domain and light chain variable domain from a PDL1 antibody described in US20160108123 (Assigned to Novartis), WO2016/000619 (Applicant: Beigene), WO2012/145493 (Applicant: Amplimmune), U.S. Pat. No. 9,205,148 (Assigned to MedImmune), WO2013/181634 (Applicant: Sorrento), and WO2016/061142 (Applicant: Novartis).

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A.

In a still further specific aspect, the antibody has reduced or minimal effector function. In a still further specific aspect the minimal effector function results from an "effector-less Fc mutation" or aglycosylation mutation. In still a further embodiment, the effector-less Fc mutation is an N297A or D265A/N297A substitution in the constant region. In some embodiments, the isolated anti-PDL1 antibody is aglycosylated. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Removal of glycosylation sites form an antibody is conveniently accomplished by altering the amino acid sequence such that one of the above-described tripeptide sequences (for N-linked glycosylation sites) is removed. The alteration may be made by substitution of an asparagine, serine or threonine residue within the glycosylation site another amino acid residue (e.g., glycine, alanine or a conservative substitution).

In a still further embodiment, the present disclosure provides for compositions comprising any of the above described anti-PDL1 antibodies in combination with at least one pharmaceutically-acceptable carrier.

In a still further embodiment, the present disclosure provides for a composition comprising an anti-PDL1, an anti-PD-1, or an anti-PDL2 antibody or antigen binding fragment thereof as provided herein and at least one pharmaceutically acceptable carrier. In some embodiments, the anti-PDL1, anti-PD-1, or anti-PDL2 antibody or antigen binding fragment thereof administered to the individual is a composition comprising one or more pharmaceutically acceptable carrier. Any of the pharmaceutically acceptable carriers described herein or known in the art may be used.

IV. Platinum Agents and Topoisomerase II Inhibitors

Platinum Agents

Platinum agents (such as cisplatin, carboplatin, oxaliplatin, and staraplatin) are widely used antitumor drugs that cause crosslinking of DNA as monoadduct, interstrand crosslinks, intrastrand crosslinks or DNA protein crosslinks. Platinum agents typically act on the adjacent N-7 position of guanine, forming a 1, 2 intrastrand crosslink (Poklar et al. (1996). *Proc. Natl. Acad. Sci. U.S.A.* 93 (15): 7606-11; Rudd et al. (1995). *Cancer Chemother. Pharmacol.* 35 (4): 323-6). The resultant crosslinking inhibits DNA repair and/or DNA synthesis in cancer cells.

Carboplatin is an exemplary platinum coordination compound used in the methods described herein. The chemical name for carboplatin is platinum, diammine [1,1-cyclobutanedicarboxylato (2-)-O,O']—, (SP-4-2), and carboplatin has the following structural formula:

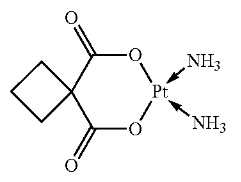

Carboplatin is a crystalline powder with the molecular formula of C6H12N204Pt and a molecular weight of 371.25. It is soluble in water at a rate of approximately 14 mg/mL, and the pH of a 1% solution is 5 to 7. It is virtually insoluble in ethanol, acetone, and dimethylacetamide. Carboplatin produces predominantly interstrand DNA cross-links, and this effect is cell-cycle nonspecific. Carboplatin is commercially available as PARAPLATIN®, BIOCARN, BLASTOCARB, BLASTOPLATIN, CARBOKEM, CARBOMAX, CARBOPA, CARBOPLAN, CARBOTEEN, CARBOTINAL, CYTOCARB, DUCARB, KARPLAT, KEMOCARB, NAPROPLAT, NEOPLATIN, NISCARBO, ONCOCARBIN, TEVACARB, WOMASTIN, and others.

Topoisomerase II Inhibitors

Inhibitors of topoisomerase II (e.g., etoposide (VP-16), teniposide, doxorubicin, daunorubicin, mitoxantrone, amsacrine, ellipticines, aurintricarboxylic acid, and HU-331) are also widely used antitumor drugs that stabilize topoisomerase II: DNA covalent complexes (i.e., "cleavage complexes") following the formation of enzyme-mediated DNA breaks. The accumulation of such cleavage complexes induces cell death pathways.

Etoposide is an exemplary topoisomerase II inhibitor used in the methods described herein. Etoposide is typically administered as the prodrug etoposide phosphate, the chemical name for which is: 4'-Demethylepipodophyllotoxin 9-[4, 6-O—(R)-ethylidene-β-Dglucopyranoside], 4' (dihydrogen phosphate).

Etoposide phosphate has the following structure:

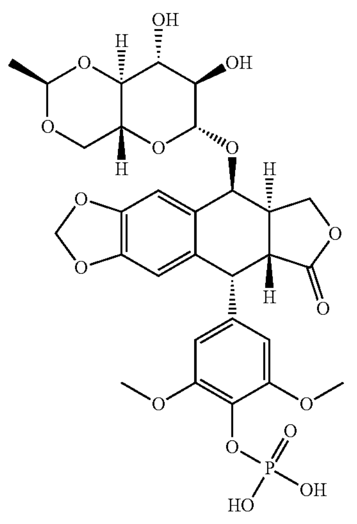

Etoposide phosphate, a phosphate ester of etoposide, is a semi-synthetic derivative of podophyllotoxin and is converted to etoposide by dephosphorylation. Etoposide causes the induction of DNA strand breaks by an interaction with DNA-topoisomerase II or the formation of free radicals, leading to cell cycle arrest (primarily at the G2 stage of the cell cycle) and cell death. Etoposide is commercially available as ETOPOPHOS®, TOPOSAR™, VP-16, VEPESID®, ACTITOP, ASIDE, BIOPOSIDE, CTOP, CYTOP, EPOSED, ESIDE, ETHOPUL, ETOLON, ETONIS, ETOPLAST, ETOSID, ETOVEL, FYTOP, FYTOSID, LASTET, NZYTOP, ONCOSIDE, PLACID, POSID, RETOPSON, TEVASIDE, TOPOK, TOPOSIDE, and others.

V. Antibody Preparation

The antibody described herein is prepared using techniques available in the art for generating antibodies, exemplary methods of which are described in more detail in the following sections.

The antibody is directed against an antigen of interest (e.g., PD-L1, such as a human PD-L1). Preferably, the antigen is a biologically important polypeptide and administration of the antibody to a mammal suffering from a disorder can result in a therapeutic benefit in that mammal.

In certain embodiments, an antibody provided herein has a dissociation constant (Kd) of ≤1 μM, ≤150 nM, ≤100 nM, ≤50 nM, ≤10 nM, ≤1 nM, ≤0.1 nM, ≤0.01 nM, or ≤0.001 nM (e.g. 10−8 M or less, e.g. from 10−8 M to 10−13 M, e.g., from 10−9 M to 10−13 M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of (1251)-labeled antigen in the presence of a titration series of unlabeled antigen, then capturing bound antigen with an anti-Fab antibody-coated plate (see, e.g., Chen et al., J. Mol. Biol. 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [125I]-antigen are mixed with serial dilutions of a Fab of interest. The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20 ™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, NJ) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one *Langmuir* binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds 106 M−1 s−1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25oC of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

(i) Antigen Preparation

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

(ii) Certain Antibody-Based Methods

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl2, or R1N═C═NR, where R and R1 are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to 1/10 the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies of the present disclosure can be made using the hybridoma method first described by Kohler et al., *Nature,* 256:495 (1975), and further described, e.g., in Hongo et al., *Hybridoma,* 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981), and Ni, *Xiandai Mianyixue,* 26 (4): 265-268 (2006) regarding human-human hybridomas. Additional methods include those described, for example, in U.S. Pat. No. 7,189,826 regarding production of monoclonal human natural IgM antibodies from hybridoma cell lines. Human hybridoma technology (Trioma technology) is described in Vollmers and Brandlein, *Histology and Histopathology,* 20 (3): 927-937 (2005) and Vollmers and Brandlein, *Methods and Findings in Experimental and Clinical Pharmacology,* 27 (3): 185-91 (2005).

For various other hybridoma techniques, see, e.g., US 2006/258841; US 2006/183887 (fully human antibodies), US 2006/059575; US 2005/287149; US 2005/100546; US 2005/026229; and U.S. Pat. Nos. 7,078,492 and 7,153,507. An exemplary protocol for producing monoclonal antibodies using the hybridoma method is described as follows. In one embodiment, a mouse or other appropriate host animal, such as a hamster, is immunized to elicit lymphocytes that produce or are capable of producing antibodies that will specifically bind to the protein used for immunization. Antibodies are raised in animals by multiple subcutaneous (sc) or intraperitoneal (ip) injections of a polypeptide of the present disclosure or a fragment thereof, and an adjuvant, such as monophosphoryl lipid A (MPL)/trehalose dicrynomycolate (TDM) (Ribi Immunochem. Research, Inc., Hamilton, Mont.). A polypeptide of the present disclosure (e.g., antigen) or a fragment thereof may be prepared using methods well known in the art, such as recombinant methods, some of which are further described herein. Serum from immunized animals is assayed for anti-antigen antibodies, and booster immunizations are optionally administered. Lymphocytes from animals producing anti-antigen antibodies are isolated. Alternatively, lymphocytes may be immunized in vitro.

Lymphocytes are then fused with myeloma cells using a suitable fusing agent, such as polyethylene glycol, to form a hybridoma cell. See, e.g., *Goding, Monoclonal Antibodies: Principles and Practice*, pp. 59-103 (Academic Press, 1986). Myeloma cells may be used that fuse efficiently, support stable high-level production of antibody by the selected antibody-producing cells, and are sensitive to a medium such as HAT medium. Exemplary myeloma cells include, but are not limited to, murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

The hybridoma cells thus prepared are seeded and grown in a suitable culture medium, e.g., a medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Preferably, serum-free hybridoma cell culture methods are used to reduce use of animal-derived serum such as fetal bovine serum, as described, for example, in Even et al., *Trends in Biotechnology,* 24 (3), 105-108 (2006).

Oligopeptides as tools for improving productivity of hybridoma cell cultures are described in Franek, Trends in Monoclonal Antibody Research, 111-122 (2005). Specifically, standard culture media are enriched with certain amino acids (alanine, serine, asparagine, proline), or with protein hydrolyzate fractions, and apoptosis may be significantly suppressed by synthetic oligopeptides, constituted of three to six amino acid residues. The peptides are present at millimolar or higher concentrations.

Culture medium in which hybridoma cells are growing may be assayed for production of monoclonal antibodies that bind to an antibody of the present disclosure. The binding specificity of monoclonal antibodies produced by hybridoma cells may be determined by immunoprecipitation or by an in vitro binding assay, such as radioimmunoassay (RIA) or enzyme-linked immunoadsorbent assay (ELISA). The binding affinity of the monoclonal antibody can be determined, for example, by Scatchard analysis. See, e.g., Munson et al., Anal. Biochem., 107:220 (1980).

After hybridoma cells are identified that produce antibodies of the desired specificity, affinity, and/or activity, the clones may be subcloned by limiting dilution procedures and grown by standard methods. See, e.g., Goding, supra. Suitable culture media for this purpose include, for example, D-MEM or RPMI-1640 medium. In addition, hybridoma cells may be grown in vivo as ascites tumors in an animal. Monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography. One procedure for isolation of proteins from hybridoma cells is described in US 2005/176122 and U.S. Pat. No. 6,919,436. The method includes using minimal salts, such as lyotropic salts, in the binding process and preferably also using small amounts of organic solvents in the elution process.

(iii) Library-Derived Antibodies

Antibodies of the present disclosure may be isolated by screening combinatorial libraries for antibodies with the desired activity or activities. For example, a variety of methods are known in the art for generating phage display libraries and screening such libraries for antibodies possessing the desired binding characteristics such as the methods described in Example 3. Additional methods are reviewed, e.g., in Hoogenboom et al. in *Methods in Molecular Biology* 178:1-37 (O'Brien et al., ed., Human Press, Totowa, NJ, 2001) and further described, e.g., in the McCafferty et al., *Nature* 348:552-554; Clackson et al., *Nature* 352:624-628 (1991); Marks et al., *J. Mol. Biol.* 222:581-597 (1992); Marks and Bradbury, in *Methods in Molecular Biology* 248:161-175 (Lo, ed., Human Press, Totowa, NJ, 2003); Sidhu et al., *J. Mol. Biol.* 338 (2): 299-310 (2004); Lee et al., *J. Mol. Biol.* 340 (5): 1073-1093 (2004); Fellouse, *Proc. Natl. Acad. Sci. USA* 101 (34): 12467-12472 (2004); and Lee et al., *J. Immunol. Methods* 284 (1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12:433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J,* 12:725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227:381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

(iv) Chimeric, Humanized and Human Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); US Patent Nos. 5, 821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285

(1992); and Presta et al. *J. Immunol.,* 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

In certain embodiments, an antibody provided herein is a human antibody. Human antibodies can be produced using various techniques known in the art. Human antibodies are described generally in van Dijk and van de Winkel, Curr. Opin. Pharmacol. 5:368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENOMOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133:3001 (1984); Brodeur et al., *Monoclonal Antibody Production Techniques and Applications*, pp. 51-63 (Marcel Dekker, Inc., New York, 1987); and Boerner et al., *J. Immunol.,* 147:86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26 (4): 265-268 (2006) (describing human-human hybridomas). Human hybridoma technology (Trioma technology) is also described in Vollmers and Brandlein, *Histology and Histopathology,* 20 (3): 927-937 (2005) and Vollmers and Brandlein, *Methods and Findings in Experimental and Clinical Pharmacology,* 27 (3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

(v) Antibody Fragments

Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. (2003) Nat. Med. 9:129-134.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')2 fragments (Carter et al., Bio/Technology 10:163-167 (1992)). According to another approach, F(ab')2 fragments can be isolated directly from recombinant host cell culture. Fab and $F(ab')_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See Antibody Engineering, ed. Borrebaeck, supra. The antibody fragment may also be a "linear antibody", e.g., as described in U.S. Pat. No. 5,641,870, for example. Such linear antibodies may be monospecific or bispecific.

(vi) Multispecific Antibodies

Multispecific antibodies have binding specificities for at least two different epitopes, where the epitopes are usually from different antigens. While such molecules normally will only bind two different epitopes (i.e. bispecific antibodies, BsAbs), antibodies with additional specificities such as trispecific antibodies are encompassed by this expression when used herein. Bispecific antibodies can be prepared as full length antibodies or antibody fragments (e.g. F(ab')2 bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

One approach known in the art for making bispecific antibodies is the "knobs-into-holes" or "protuberance-into-cavity" approach (see, e.g., U.S. Pat. No. 5,731,168). In this approach, two immunoglobulin polypeptides (e.g., heavy chain polypeptides) each comprise an interface. An interface of one immunoglobulin polypeptide interacts with a corresponding interface on the other immunoglobulin polypeptide, thereby allowing the two immunoglobulin polypeptides to associate. These interfaces may be engineered such that a "knob" or "protuberance" (these terms may be used interchangeably herein) located in the interface of one immunoglobulin polypeptide corresponds with a "hole" or "cavity"

(these terms may be used interchangeably herein) located in the interface of the other immunoglobulin polypeptide. In some embodiments, the hole is of identical or similar size to the knob and suitably positioned such that when the two interfaces interact, the knob of one interface is positionable in the corresponding hole of the other interface. Without wishing to be bound to theory, this is thought to stabilize the heteromultimer and favor formation of the heteromultimer over other species, for example homomultimers. In some embodiments, this approach may be used to promote the heteromultimerization of two different immunoglobulin polypeptides, creating a bispecific antibody comprising two immunoglobulin polypeptides with binding specificities for different epitopes.

In some embodiments, a knob may be constructed by replacing a small amino acid side chain with a larger side chain. In some embodiments, a hole may be constructed by replacing a large amino acid side chain with a smaller side chain. Knobs or holes may exist in the original interface, or they may be introduced synthetically. For example, knobs or holes may be introduced synthetically by altering the nucleic acid sequence encoding the interface to replace at least one "original" amino acid residue with at least one "import" amino acid residue. Methods for altering nucleic acid sequences may include standard molecular biology techniques well known in the art. The side chain volumes of various amino acid residues are shown in Table 1 below. In some embodiments, original residues have a small side chain volume (e.g., alanine, asparagine, aspartic acid, glycine, serine, threonine, or valine), and import residues for forming a knob are naturally occurring amino acids and may include arginine, phenylalanine, tyrosine, and tryptophan. In some embodiments, original residues have a large side chain volume (e.g., arginine, phenylalanine, tyrosine, and tryptophan), and import residues for forming a hole are naturally occurring amino acids and may include alanine, serine, threonine, and valine.

TABLE 1

Properties of Amino Acid Residues

| Amino acid | One-letter abbreviation | Mass[a] (daltons) | Volume[b] (Å$^3$) | Accessible surface area[c] (Å$^2$) |
|---|---|---|---|---|
| Alanine (Ala) | A | 71.08 | 88.6 | 115 |
| Arginine (Arg) | R | 156.20 | 173.4 | 225 |
| Asparagine (Asn) | N | 114.11 | 117.7 | 160 |
| Aspartic Acid (Asp) | D | 115.09 | 111.1 | 150 |
| Cysteine (Cys) | C | 103.14 | 108.5 | 135 |
| Glutamine (Gln) | Q | 128.14 | 143.9 | 180 |
| Glutamic Acid (Glu) | E | 129.12 | 138.4 | 190 |
| Glycine (Gly) | G | 57.06 | 60.1 | 75 |
| Histidine (His) | H | 137.15 | 153.2 | 195 |
| Isoleucine (Ile) | I | 113.17 | 166.7 | 175 |
| Leucine (Leu) | L | 113.17 | 166.7 | 170 |
| Lysine (Lys) | K | 128.18 | 168.6 | 200 |
| Methionine (Met) | M | 131.21 | 162.9 | 185 |
| Phenylalanine (Phe) | F | 147.18 | 189.9 | 210 |
| Proline (Pro) | P | 97.12 | 122.7 | 145 |
| Serine (Ser) | S | 87.08 | 89.0 | 115 |
| Threonine (Thr) | T | 101.11 | 116.1 | 140 |
| Tryptophan (Trp) | W | 186.21 | 227.8 | 255 |
| Tyrosine (Tyr) | Y | 163.18 | 193.6 | 230 |
| Valine (Val) | V | 99.14 | 140.0 | 155 |

[a]Molecular weight of amino acid minus that of water. Values from Handbook of Chemistry and Physics, 43rd ed. Cleveland, Chemical Rubber Publishing Co., 1961.
[b]Values from A.A. Zamyatnin, Prog. Biophys. Mol. Biol. 24:107-123, 1972.
[c]Values from C. Chothia, J. Mol. Biol. 105:1-14, 1975. The accessible surface area is defined in FIGS. 6-20 of this reference.

In some embodiments, original residues for forming a knob or hole are identified based on the three-dimensional structure of the heteromultimer. Techniques known in the art for obtaining a three-dimensional structure may include X-ray crystallography and NMR. In some embodiments, the interface is the CH3 domain of an immunoglobulin constant domain. In these embodiments, the CH3/CH3 interface of human $IgG_1$ involves sixteen residues on each domain located on four anti-parallel β-strands. Without wishing to be bound to theory, mutated residues are preferably located on the two central anti-parallel β-strands to minimize the risk that knobs can be accommodated by the surrounding solvent, rather than the compensatory holes in the partner CH3 domain. In some embodiments, the mutations forming corresponding knobs and holes in two immunoglobulin polypeptides correspond to one or more pairs provided in Table 2.

TABLE 2

Exemplary sets of corresponding knob-and hole-forming mutations*

| CH3 of first immunoglobulin | CH3 of second immunoglobulin |
|---|---|
| T336Y | Y407T |
| T366W | Y407A |
| F405A | T394W |
| Y407T | T366Y |
| T366Y:F405A | T394W:Y407T |
| T366W:F405W | T394S:Y407A |
| F405W:Y407A | T366W:T394S |
| F405W | T394S |

*Mutations are denoted by the original residue, followed by the position using the Kabat numbering system, and then the import residue (all residues are given in single-letter amino acid code). Multiple mutations are separated by a colon.

In some embodiments, an immunoglobulin polypeptide comprises a CH3 domain comprising one or more amino acid substitutions listed in Table 2 above. In some embodiments, a bispecific antibody comprises a first immunoglobulin polypeptide comprising a CH3 domain comprising one or more amino acid substitutions listed in the left column of Table 2, and a second immunoglobulin polypeptide comprising a CH3 domain comprising one or more corresponding amino acid substitutions listed in the right column of Table 2.

Following mutation of the DNA as discussed above, polynucleotides encoding modified immunoglobulin polypeptides with one or more corresponding knob- or hole-forming mutations may be expressed and purified using standard recombinant techniques and cell systems known in the art. See, e.g., U.S. Pat. Nos. 5,731,168; 5,807,706; 5,821,333; 7,642,228; 7,695,936; 8,216,805; U.S. Pub. No. 2013/0089553; and Spiess et al., Nature Biotechnology 31:753-758, 2013. Modified immunoglobulin polypeptides may be produced using prokaryotic host cells, such as *E. coli*, or eukaryotic host cells, such as CHO cells. Corresponding knob- and hole-bearing immunoglobulin polypeptides may be expressed in host cells in co-culture and purified together as a heteromultimer, or they may be expressed in single cultures, separately purified, and assembled in vitro. In some embodiments, two strains of bacterial host cells (one expressing an immunoglobulin polypeptide with a knob, and the other expressing an immunoglobulin polypeptide with a hole) are co-cultured using standard bacterial culturing techniques known in the art. In some embodiments, the two strains may be mixed in a specific ratio, e.g., so as to achieve equal expression levels in culture. In some embodiments, the two strains may be mixed in a 50:50, 60:40, or 70:30 ratio. After polypeptide expression, the cells may be lysed together, and protein may be extracted. Standard techniques known in the art that allow for measuring the abundance of homo-multimeric vs. hetero-multimeric species may include size exclusion chromatography. In some embodiments, each modified immunoglobulin polypeptide is expressed separately using standard recombinant techniques, and they may be assembled together in vitro. Assembly may be achieved, for example, by purifying each modified immunoglobulin polypeptide, mixing and incubating them together in equal mass, reducing disulfides (e.g., by treating with dithiothreitol), concentrating, and reoxidizing the polypeptides. Formed bispecific antibodies may be purified using standard techniques including cation-exchange chromatography and measured using standard techniques including size exclusion chromatography. For a more detailed description of these methods, see Speiss et al., *Nat Biotechnol* 31:753-8, 2013. In some embodiments, modified immunoglobulin polypeptides may be expressed separately in CHO cells and assembled in vitro using the methods described above.

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is typical to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in WO96/27011, the interface between a pair of antibody molecules can be engineered to maximize the percentage of heterodimers which are recovered from recombinant cell culture. One interface comprises at least a part of the CH 3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229:81 (1985) describe a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., J. Exp. Med., 175:217-225 (1992) describe the production of a fully humanized bispecific antibody F(ab')2 molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., *J. Immunol.,* 148 (5): 1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA,* 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al, *J. Immunol,* 152:5368 (1994).

Antibodies with more than two valencies are contemplated. For example, trispecific antibodies can be prepared. Tuft et al. *J. Immunol.* 147:60 (1991).

(vii) Single-Domain Antibodies

In some embodiments, an antibody of the present disclosure is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

(vii) Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

(ix) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 3. More substantial changes are provided in Table 3 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 3

Conservative Substitutions.

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tye; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

a. hydrophobic: Norleucine, Met, Ala, Val, Leu, Ile;

b. neutral hydrophilic: Cys, Ser, Thr, Asn, Gln;

c. acidic: Asp, Glu;

d. basic: His, Lys, Arg;

e. residues that influence chain orientation: Gly, Pro;

f. aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

(x) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the present disclosure may be made in order to create antibody variants with certain improved properties.

In one embodiment, antibody variants are provided comprising an Fc region wherein a carbohydrate structure attached to the Fc region has reduced fucose or lacks fucose, which may improve ADCC function. Specifically, antibodies are contemplated herein that have reduced fucose relative to the amount of fucose on the same antibody produced in a wild-type CHO cell. That is, they are characterized by having a lower amount of fucose than they would otherwise have if produced by native CHO cells (e.g., a CHO cell that produce a native glycosylation pattern, such as, a CHO cell containing a native FUT8 gene). In certain embodiments, the antibody is one wherein less than about 50%, 40%, 30%, 20%, 10%, or 5% of the N-linked glycans thereon comprise fucose. For example, the amount of fucose in such an antibody may be from 1% to 80%, from 1% to 65%, from 5% to 65% or from 20% to 40%. In certain embodiments, the antibody is one wherein none of the N-linked glycans thereon comprise fucose, i.e., wherein the antibody is completely without fucose, or has no fucose or is afucosylated. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87:614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87:614 (2004); Kanda, Y. et al., *Biotechnol. Bioeng.,* 94 (4): 680-688 (2006); and WO2003/085107).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); US 2005/0123546 (Umana et al.), and Ferrara et al., Biotechnology and Bioengineering, 93 (5): 851-861 (2006). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In certain embodiments, the antibody variants comprising an Fc region described herein are capable of binding to an FcγRIII. In certain embodiments, the antibody variants comprising an Fc region described herein have ADCC activity in the presence of human effector cells or have increased ADCC activity in the presence of human effector cells compared to the otherwise same antibody comprising a human wild-type IgG1Fc region.

(xi) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the present disclosure contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc (RIII only, whereas monocytes express Fc(RI, Fc (RII and Fc (RIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362

(see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); 5,821,337 (see Bruggemann, M. et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M.S. et al., Blood 101:1045-1052 (2003); and Cragg, M. S. and M. J. Glennie, Blood 103:2738-2743 (2004)). FcRn binding and in vivo clearance/half-life determinations can also be performed using methods known in the art (see, e.g., Petkova, S. B. et al., Int'l. Immunol. 18 (12): 1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., J. Biol. Chem. 9 (2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues). In an exemplary embodiment, the antibody comprising the following amino acid substitutions in its Fc region: S298A, E333A, and K334A.

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. J. Immunol. 164:4178-4184 (2000).

Antibodies with increased half-lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.)). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, *Nature* 322:738-40 (1988); U.S. Pat. Nos. 5,648,260; 5,624,821; and WO 94/29351 concerning other examples of Fc region variants.

(xii) Antibody Derivatives

The antibodies of the present disclosure can be further modified to contain additional nonproteinaceous moieties that are known in the art and readily available. In certain embodiments, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

(xiii) Vectors, Host Cells, and Recombinant Methods

Antibodies may also be produced using recombinant methods. For recombinant production of an anti-antigen antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

In a still further aspect, provided herein are nucleic acids encoding any of the antibodies described herein. In some embodiments, the nucleic acid further comprises a vector suitable for expression of the nucleic acid encoding any of the previously described anti-PDL1, anti-PD-1, or anti-PDL2 antibodies. In a still further specific aspect, the vector further comprises a host cell suitable for expression of the nucleic acid. In a still further specific aspect, the host cell is a eukaryotic cell or a prokaryotic cell. In a still further specific aspect, the eukaryotic cell is a mammalian cell, such as Chinese Hamster Ovary (CHO).

In a still further embodiment, provided is an isolated nucleic acid encoding a light chain or a heavy chain variable region sequence of an anti-PDL1 antibody, wherein:

(a) the heavy chain further comprises and HVR-H1, HVR-H2 and an HVR-H3 sequence having at least 85% sequence identity to GFTFSDSWIH (SEQ ID NO:1), AWISPYGGSTYYADSVKG (SEQ ID NO:2) and RHWPGGFDY (SEQ ID NO:3), respectively, and/or (b) the light chain further comprises an HVR-L1, HVR-L2 and an HVR-L3 sequence having at least 85% sequence identity to RASQDVSTAVA (SEQ ID NO:4), SASFLYS (SEQ ID NO:5) and QQYLYHPAT (SEQ ID NO:6), respectively.

In a specific aspect, the sequence identity is 86%, 87%, 88%, 89%, 90%, 91%, 92%, 93%, 94%, 95%, 96%, 97%, 98%, 99% or 100%.

The antibody or antigen binding fragment thereof, may be made using methods known in the art, for example, by a process comprising culturing a host cell containing nucleic acid encoding any of the previously described anti-PDL1, anti-PD-1, or anti-PDL2 antibodies or antigen-binding fragment in a form suitable for expression, under conditions suitable to produce such antibody or fragment, and recovering the antibody or fragment. Further exemplary techniques and methods are described herein.

(a) Signal Sequence Component

An antibody of the present disclosure may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (e.g., cleaved by a signal peptidase) by the host cell. For prokaryotic host cells that do not recognize and process a native antibody signal sequence, the signal sequence is substituted by a prokaryotic signal sequence selected, for example, from the group of the alkaline phosphatase, penicillinase, 1 pp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

(b) Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ, plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter.

(c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up antibody-encoding nucleic acid, such as DHFR, glutamine synthetase (GS), thymidine kinase, metallothionein-I and -II, preferably primate metallothionein genes, adenosine deaminase, ornithine decarboxylase, etc.

For example, cells transformed with the DHFR gene are identified by culturing the transformants in a culture medium containing methotrexate (Mtx), a competitive antagonist of DHFR. Under these conditions, the DHFR gene is amplified along with any other co-transformed nucleic acid. A Chinese hamster ovary (CHO) cell line deficient in endogenous DHFR activity (e.g., ATCC CRL-9096) may be used.

Alternatively, cells transformed with the GS gene are identified by culturing the transformants in a culture medium containing L-methionine sulfoximine (Msx), an inhibitor of GS. Under these conditions, the GS gene is amplified along with any other co-transformed nucleic acid. The GS selection/amplification system may be used in combination with the DHFR selection/amplification system described above.

Alternatively, host cells (particularly wild-type hosts that contain endogenous DHFR) transformed or co-transformed with DNA sequences encoding an antibody of interest, wild-type DHFR gene, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4-1. Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, Bio/Technology, 8:135 (1990). Stable multi-copy expression vectors for secretion of mature recombinant human serum albumin by industrial strains of *Kluyveromyces* have also been disclosed. Fleer et al., *Bio/Technology,* 9:968-975 (1991).

(d) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

Full length antibody, antibody fusion proteins, and antibody fragments can be produced in bacteria, in particular when glycosylation and Fc effector function are not needed, such as when the therapeutic antibody is conjugated to a cytotoxic agent (e.g., a toxin) that by itself shows effectiveness in tumor cell destruction. Full length antibodies have greater half-life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), U.S. Pat. No. 5,840,523 (Simmons et al.), which describes translation initiation region (TIR) and signal sequences for optimizing expression and secretion. See also Charlton, Methods in Molecular Biology, Vol. 248 (B. K. C. Lo, ed., Humana Press, Totowa, N.J., 2003), pp. 245-254, describing expression of antibody fragments in *E. coli*. After expression, the antibody may be isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as Schizosaccharomyces pombe; Kluyveromyces hosts such as, e.g., *K. lactis, K. fragilis* (ATCC 12,424), *K. bulgaricus* (ATCC 16,045), K. wickeramii (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma* reesia (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*. For a review discussing the use of yeasts and filamentous fungi for the production of therapeutic proteins, see, e.g., Gerngross, Nat. Biotech. 22:1409-1414 (2004).

Certain fungi and yeast strains may be selected in which glycosylation pathways have been "humanized," resulting in the production of an antibody with a partially or fully human glycosylation pattern. See, e.g., Li et al., Nat. Biotech. 24:210-215 (2006) (describing humanization of the glycosylation pathway in *Pichia pastoris*); and Gerngross et al., supra.

Suitable host cells for the expression of glycosylated antibody are also derived from multicellular organisms (invertebrates and vertebrates). Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present disclosure, particularly for transfection of *Spodoptera frugiperda* cells.

Plant cell cultures of cotton, corn, potato, soybean, *petunia*, tomato, duckweed (Leninaceae), alfalfa (*M. truncatula*), and tobacco can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may be used as hosts, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as NSO and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J., 2003), pp. 255-268.

Host cells are transformed with the above-described expression or cloning vectors for antibody production and cultured in conventional nutrient media modified as appropriate for inducing promoters, selecting transformants, or amplifying the genes encoding the desired sequences.

(e) Culturing the Host Cells

The host cells used to produce an antibody of the present disclosure may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(xiv) Purification of Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, gel electrophoresis, dialysis, and affinity chromatography, with affinity chromatography being among one of the typically preferred purification steps. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

In general, various methodologies for preparing antibodies for use in research, testing, and clinical are well-established in the art, consistent with the above-described methodologies and/or as deemed appropriate by one skilled in the art for a particular antibody of interest.

VI. Selecting Biologically Active Antibodies

Antibodies produced as described above may be subjected to one or more "biological activity" assays to select an antibody with beneficial properties from a therapeutic perspective or selecting formulations and conditions that retain biological activity of the antibody. The antibody may be tested for its ability to bind the antigen against which it was raised. For example, methods known in the art (such as ELISA, Western Blot, etc.) may be used.

For example, for an anti-PDL1 antibody, the antigen binding properties of the antibody can be evaluated in an assay that detects the ability to bind to PDL1. In some embodiments, the binding of the antibody may be determined by saturation binding; ELISA; and/or competition assays (e.g. RIA's), for example. Also, the antibody may be subjected to other biological activity assays, e.g., in order to evaluate its effectiveness as a therapeutic. Such assays are known in the art and depend on the target antigen and intended use for the antibody. For example, the biological effects of PD-L1 blockade by the antibody can be assessed in CD8+T cells, a lymphocytic choriomeningitis virus (LCMV) mouse model and/or a syngeneic tumor model e.g., as described in U.S. Pat. No. 8,217,149.

To screen for antibodies which bind to a particular epitope on the antigen of interest (e.g., those which block binding of the anti-PDL1 antibody of the example to PD-L1), a routine cross-blocking assay such as that described in Antibodies, *A Laboratory Manual*, Cold Spring Harbor Laboratory, Ed Harlow and David Lane (1988), can be performed. Alternatively, epitope mapping, e.g. as described in Champe et al., *J. Biol. Chem.* 270:1388-1394 (1995), can be performed to determine whether the antibody binds an epitope of interest.

VII. Pharmaceutical Compositions and Formulations

Also provided herein are pharmaceutical compositions and formulations, e.g., for the treatment of lung cancer (such as small cell lung cancer, e.g., extensive stage small cell lung cancer) comprising a PD-1 axis binding antagonist (such as atezolizumab), a platinum agent (such as carboplatin), and a topoisomerase II inhibitor (such as etoposide). In some embodiments, the pharmaceutical compositions and formulations further comprise a pharmaceutically acceptable carrier.

In some embodiments, an anti-PDL1 antibody described herein (such as atezolizumab) is in a formulation comprising the antibody at an amount of about 60 mg/mL, histidine acetate in a concentration of about 20 mM, sucrose in a concentration of about 120 mM, and polysorbate (e.g., polysorbate 20) in a concentration of 0.04% (w/v), and the formulation has a pH of about 5.8. In some embodiments, the anti-PDL1 antibody described herein (such as atezolizumab) is in a formulation comprising the antibody in an amount of about 125 mg/mL, histidine acetate in a concentration of about 20 mM, sucrose is in a concentration of about 240 mM, and polysorbate (e.g., polysorbate 20) in a concentration of 0.02% (w/v), and the formulation has a pH of about 5.5.

After preparation of the antibody of interest (e.g., techniques for producing antibodies which can be formulated as disclosed herein are elaborated herein and are known in the art), the pharmaceutical formulation comprising it is prepared. In certain embodiments, the antibody to be formulated has not been subjected to prior lyophilization and the formulation of interest herein is an aqueous formulation. In certain embodiments, the antibody is a full length antibody. In one embodiment, the antibody in the formulation is an antibody fragment, such as an F(ab')2, in which case problems that may not occur for the full length antibody (such as clipping of the antibody to Fab) may need to be addressed. The therapeutically effective amount of antibody present in the formulation is determined by taking into account the desired dose volumes and mode(s) of administration, for example. From about 25 mg/mL to about 150 mg/mL, or from about 30 mg/mL to about 140 mg/mL, or from about 35 mg/mL to about 130 mg/mL, or from about 40 mg/mL to about 120 mg/mL, or from about 50 mg/mL to about 130 mg/mL, or from about 50 mg/mL to about 125 mg/mL, or from about 50 mg/mL to about 120 mg/mL, or from about 50 mg/mL to about 110 mg/mL, or from about 50 mg/mL to about 100 mg/mL, or from about 50 mg/mL to about 90 mg/mL, or from about 50 mg/mL to about 80 mg/mL, or from about 54 mg/mL to about 66 mg/mL is an exemplary antibody concentration in the formulation.

An aqueous formulation is prepared comprising the antibody in a pH-buffered solution. In some embodiments, the buffer of the present disclosure has a pH in the range from about 5.0 to about 7.0. In certain embodiments the pH is in the range from about 5.0 to about 6.5, the pH is in the range from about 5.0 to about 6.4, in the range from about 5.0 to about 6.3, the pH is in the range from about 5.0 to about 6.2, the pH is in the range from about 5.0 to about 6.1, the pH is in the range from about 5.5 to about 6.1, the pH is in the range from about 5.0 to about 6.0, the pH is in the range from about 5.0 to about 5.9, the pH is in the range from about 5.0 to about 5.8, the pH is in the range from about 5.1 to about 6.0, the pH is in the range from about 5.2 to about 6.0, the pH is in the range from about 5.3 to about 6.0, the pH is in the range from about 5.4 to about 6.0, the pH is in the range from about 5.5 to about 6.0, the pH is in the range from about 5.6 to about 6.0, the pH is in the range from about 5.7 to about 6.0, or the pH is in the range from about 5.8 to about 6.0. In some embodiments, the formulation has a pH of 6.0 or about 6.0. In some embodiments, the formulation has a pH of 5.9 or about 5.9. In some embodiments, the formulation has a pH of 5.8 or about 5.8. In some embodiments, the formulation has a pH of 5.7 or about 5.7. In some embodiments, the formulation has a pH of 5.6 or about 5.6. In some embodiments, the formulation has a pH of 5.5 or about 5.5. In some embodiments, the formulation has a pH of 5.4 or about 5.4. In some embodiments, the formulation has a pH of 5.3 or about 5.3. In some embodiments, the formulation has a pH of 5.2 or about 5.2. Examples of buffers that will control the pH within this range include histidine (such as L-histidine) or sodium acetate. In certain embodiments, the buffer contains histidine acetate or sodium acetate in the concentration of about 15 mM to about 25 mM. In some embodiments, the buffer contains histidine acetate or sodium acetate in the concentration of about 15 mM to about 25 mM, about 16 mM to about 25 mM, about 17 mM to about 25 mM, about 18 mM to about 25 mM, about 19 mM to about 25 mM, about 20 mM to about 25 mM, about 21 mM to about 25 mM, about 22 mM to about 25 mM, about 15 mM, about 16 mM, about 17 mM, about 18 mM, about 19 mM, about 20 mM, about 21 mM, about 22 mM, about 23 mM, about 24 mM, or about 25 mM. In one embodiment, the buffer is histidine acetate or sodium acetate in an amount of about 20 mM, pH 5.0. In one embodiment, the buffer is histidine acetate or sodium acetate in an amount of about 20 mM, pH 5.1. In one embodiment, the buffer is histidine acetate or sodium acetate in an amount of about 20 mM, pH 5.2. In one embodiment, the buffer is histidine acetate or sodium acetate in an amount of about 20 mM, pH 5.3. In one embodiment, the buffer is histidine acetate or sodium acetate in an amount of about 20 mM, pH 5.4. In one embodiment, the buffer is histidine acetate or sodium acetate in an amount of about 20 mM, pH 5.5. In one embodiment, the buffer is histidine acetate or sodium acetate in an amount of about 20 mM, pH 5.6. In one embodiment, the buffer is histidine acetate or sodium acetate in an amount of about 20 mM, pH 5.7. In one embodiment, the buffer is histidine acetate or sodium acetate in an amount of about 20 mM, pH 5.8. In one embodiment, the buffer is histidine acetate or sodium acetate in an amount of about 20 mM, pH 5.9. In one embodiment, the buffer is histidine acetate or sodium acetate in an amount of about 20 mM, pH 6.0. In one embodiment, the buffer is histidine acetate or sodium acetate in an amount of about 20 mM, pH 6.1. In one embodiment, the buffer is histidine acetate or sodium acetate in an amount of about 20 mM, pH 6.2. In one embodiment, the buffer is histidine acetate or sodium acetate in an amount of about 20 mM, pH 6.3. In one embodiment, the buffer is histidine acetate or sodium acetate in an amount of about 25 mM, pH 5.2. In one embodiment, the buffer is histidine acetate or sodium acetate in an amount of about 25 mM, pH 5.3. In one embodiment, the buffer is histidine acetate or sodium acetate in an amount of about 25 mM, pH 5.4. In one embodiment, the buffer is histidine acetate or sodium acetate in an amount of about 25 mM, pH 5.5. In one embodiment, the buffer is histidine acetate or sodium acetate in an amount of about 25 mM, pH 5.6. In one embodiment, the buffer is histidine acetate or sodium acetate in an amount of about 25 mM, pH 5.7. In one embodiment, the buffer is histidine acetate or sodium acetate in an amount of about 25 mM, pH 5.8. In one embodiment, the buffer is histidine acetate or sodium acetate in an amount of about 25 mM, pH 5.9. In one embodiment, the buffer is histidine acetate or sodium acetate in an amount of about 25 mM, pH 6.0. In one embodiment, the buffer is histidine acetate or sodium acetate in an amount of about 25 mM, pH 6.1. In one embodiment, the buffer is histidine acetate or sodium acetate in an amount of about 25 mM, pH 6.2. In one embodiment, the buffer is histidine acetate or sodium acetate in an amount of about 25 mM, pH 6.3.

In some embodiments, the formulation further comprises sucrose in an amount of about 60 mM to about 240 mM. In some embodiments, sucrose in the formulation is about 60 mM to about 230 mM, about 60 mM to about 220 mM, about 60 mM to about 210 mM, about 60 mM to about 200 mM, about 60 mM to about 190 mM, about 60 mM to about 180 mM, about 60 mM to about 170 mM, about 60 mM to about 160 mM, about 60 mM to about 150 mM, about 60 mM to about 140 mM, about 80 mM to about 240 mM, about 90 mM to about 240 mM, about 100 mM to about 240 mM, about 110 mM to about 240 mM, about 120 mM to about 240 mM, about 130 mM to about 240 mM, about 140 mM to about 240 mM, about 150 mM to about 240 mM, about 160 mM to about 240 mM, about 170 mM to about 240 mM, about 180 mM to about 240 mM, about 190 mM to about 240 mM, about 200 mM to about 240 mM, about 80 mM to about 160 mM, about 100 mM to about 140 mM, or about 110 mM to about 130 mM. In some embodiments, sucrose in the formulation is about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 200 mM, about 210 mM, about 220 mM, about 230 mM, or about 240 mM.

In some embodiments, the antibody concentration in the formulation is about 40 mg/ml to about 125 mg/ml. In some embodiments, the antibody concentration in the formulation is about 40 mg/ml to about 120 mg/ml, about 40 mg/ml to about 110 mg/ml, about 40 mg/ml to about 100 mg/ml, about 40 mg/ml to about 90 mg/ml, about 40 mg/ml to about 80 mg/ml, about 40 mg/ml to about 70 mg/ml, about 50 mg/ml to about 120 mg/ml, about 60 mg/ml to about 120 mg/ml, about 70 mg/ml to about 120 mg/ml, about 80 mg/ml to about 120 mg/ml, about 90 mg/ml to about 120 mg/ml, or about 100 mg/ml to about 120 mg/ml. In some embodiments, the antibody concentration in the formulation is about 60 mg/ml. In some embodiments, the antibody concentration in the formulation is about 65 mg/ml. In some embodiments, the antibody concentration in the formulation is about 70 mg/ml. In some embodiments, the antibody concentration in the formulation is about 75 mg/ml. In some embodiments, the antibody concentration in the formulation is about 80 mg/ml. In some embodiments, the antibody concentration in the formulation is about 85 mg/ml. In some embodiments, the antibody concentration in the formulation is about 90 mg/ml. In some embodiments, the antibody concentration in the formulation is about 95 mg/ml. In some embodiments, the antibody concentration in the formulation is about 100 mg/ml. In some embodiments, the antibody concentration in the formulation is about 110 mg/ml. In some embodiments, the antibody concentration in the formulation is about 125 mg/ml.

In some embodiments, a surfactant is added to the antibody formulation. Exemplary surfactants include nonionic surfactants such as polysorbates (e.g. polysorbates 20, 80 etc.) or poloxamers (e.g. poloxamer 188, etc.). The amount of surfactant added is such that it reduces aggregation of the formulated antibody and/or minimizes the formation of particulates in the formulation and/or reduces adsorption. For example, the surfactant may be present in the formulation in an amount from about 0.001% to about 0.5% (w/v). In some embodiments, the surfactant (e.g., polysorbate 20) is from about 0.005% to about 0.2%, from about 0.005% to about 0.1%, from about 0.005% to about 0.09%, from about 0.005% to about 0.08%, from about 0.005% to about 0.07%, from about 0.005% to about 0.06%, from about 0.005% to about 0.05%, from about 0.005% to about 0.04%, from about 0.008% to about 0.06%, from about 0.01% to about 0.06%, from about 0.02% to about 0.06%, from about 0.01% to about 0.05%, or from about 0.02% to about 0.04%. In certain embodiments, the surfactant (e.g., polysorbate 20) is present in the formulation in an amount of 0.005% or about 0.005%. In certain embodiments, the surfactant (e.g., polysorbate 20) is present in the formulation in an amount of 0.006% or about 0.006%. In certain embodiments, the surfactant (e.g., polysorbate 20) is present in the formulation in an amount of 0.007% or about 0.007%. In certain embodiments, the surfactant (e.g., polysorbate 20) is present in the formulation in an amount of 0.008% or about 0.008%. In certain embodiments, the surfactant (e.g., polysorbate 20) is present in the formulation in an amount of 0.009% or about 0.009%. In certain embodiments, the surfactant (e.g., polysorbate 20) is present in the formulation in an amount of 0.01% or about 0.01%. In certain embodiments, the surfactant (e.g., polysorbate 20) is present in the formulation in an amount of 0.02% or about 0.02%. In certain embodiments, the surfactant (e.g., polysorbate 20) is present in the formulation in an amount of 0.03% or about 0.03%. In certain embodiments, the surfactant (e.g., polysorbate 20) is present in the formulation in an amount of 0.04% or about 0.04%. In certain embodiments, the surfactant (e.g., polysorbate 20) is present in the formulation in an amount of 0.05% or about 0.05%. In certain embodiments, the surfactant (e.g., polysorbate 20) is present in the formulation in an amount of 0.06% or about 0.06%. In certain embodiments, the surfactant (e.g., polysorbate 20) is present in the formulation in an amount of 0.07% or about 0.07%. In certain embodiments, the surfactant (e.g., polysorbate 20) is present in the formulation in an amount of 0.08% or about 0.08%. In certain embodiments, the surfactant (e.g., polysorbate 20) is present in the formulation in an amount of 0.1% or about 0.1%. In certain embodiments, the surfactant (e.g., polysorbate 20) is present in the formulation in an amount of 0.2% or about 0.2%. In certain embodiments, the surfactant (e.g., polysorbate 20) is present in the formulation in an amount of 0.3% or about 0.3%. In certain embodiments, the surfactant (e.g., polysorbate 20) is present in the formulation in an amount of 0.4% or about 0.4%. In certain embodiments, the surfactant (e.g., polysorbate 20) is present in the formulation in an amount of 0.5% or about 0.5%.

In one embodiment, the formulation contains the above-identified agents (e.g., antibody, buffer, sucrose, and/or surfactant) and is essentially free of one or more preservatives, such as benzyl alcohol, phenol, m-cresol, chlorobutanol and benzethonium Cl. In another embodiment, a preservative may be included in the formulation, particularly where the formulation is a multidose formulation. The concentration of preservative may be in the range from about 0.1% to about 2%, preferably from about 0.5% to about 1%. One or more other pharmaceutically acceptable carriers, excipients or stabilizers such as those described in Remington's Pharmaceutical Sciences 16th edition, Osol, A. Ed. (1980) may be included in the formulation provided that they do not adversely affect the desired characteristics of the formulation. Acceptable carriers, excipients or stabilizers are nontoxic to recipients at the dosages and concentrations employed and include; additional buffering agents; co-solvents; anti-oxidants including ascorbic acid and methionine; chelating agents such as EDTA; metal complexes (e.g. Zn-protein complexes); biodegradable polymers such as polyesters; and/or salt-forming counterions. Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

The formulation herein may also contain more than one protein as necessary for the particular indication being treated, preferably those with complementary activities that do not adversely affect the other protein. For example, where the antibody is anti-PDL1 (such as atezolizumab), it may be combined with another agent (e.g., a chemotherapeutic agent, and anti-neoplastic agent).

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The composition and formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. The formulations to be used for in vivo administration are generally sterile. Sterility may be readily accomplished, e.g., by filtration through sterile filtration membranes.

Pharmaceutical formulations of carboplatin and/or etoposide are commercially available. For example, carboplatin is known under a variety of trade names (as described elsewhere herein) including PARAPLATIN®. Etoposide is known under a variety of trade names (as described elsewhere herein), including VP-16, ETOPOPHOS®, TOPOSAR™, and VEPESID®. In some embodiments, the carboplatin and/or the etoposide are provided in separate containers. In some embodiments, the carboplatin and/or the etoposide are each used and/or prepared for administration to an individual as described in the prescribing information available with the commercially available product.

VIII. Methods of Treatment

Provided herein are methods for treating or delaying progression of cancer (such as lung cancer, e.g., small cell lung cancer, e.g. extensive-stage small cell lung cancer) in an individual comprising administering to the individual an effective amount of a PD-1 axis binding antagonist (e.g., an anti-PD-L1 antibody), a platinum agent (e.g., carboplatin), and a topoisomerase inhibitor (e.g., etoposide). In some embodiments, the treatment results in a sustained response in the individual after cessation of the treatment. In some embodiments, the treatment extends the progression free survival (PFS) and/or the overall survival (OS) of the individual. The methods described herein may find use in treating conditions where enhanced immunogenicity is desired such as increasing tumor immunogenicity for the treatment of cancer. Also provided herein are methods of enhancing immune function in an individual having (such as lung cancer, e.g., small cell lung cancer, e.g. extensive-stage small cell lung cancer) in an individual comprising administering to the individual an effective amount of a PD-1 axis binding antagonist (e.g., an anti-PD-L1 antibody), a platinum agent (e.g., carboplatin), and a topoisomerase inhibitor (e.g., etoposide).

In some embodiments, the lung cancer is small cell lung cancer (SCLC). In some embodiments, the SCLC is extensive-stage small cell lung cancer (ES-SCLC), also referred to as stage 4 (IV) SCLC. In some embodiments, the SCLC is histologically or cytologically confirmed ES-SCLC, according to or as defined by the Veterans Administration Lung Study Group (VALG) staging system (see, e.g., Micke et al. (2002) "Staging small cell lung cancer: Veterans Administration Lung Study Group versus International Association for the Study of Lung Cancer-what limits limited disease?" Lung Cancer 37:271-6). In some embodiments, SCLC is classified as ES-SCLC if the individual is inoperable and cannot be classified as having limited or limited stage SCLC (L-SCLC or LS-SCLC). In some embodiments, the ES-SCLC is detectable and/or has spread outside the originally affected lung. In some embodiments, the ES-SCLC is detectable and/or has spread further into other (e.g., distant) organs, such as (but not limited to) the liver, adrenal glands, lymph nodes and/or brain. In some embodiments, the ES-SCLC is difficult to treat.

In some embodiments, the individual has a poor prognosis. In some embodiments, the individual is a treatment-naïve individual. In some embodiments, a treatment-naïve individual is an individual who has not received prior treatment, e.g., for cancer, for SCLC, or for ES-SCLC. In some embodiments, the treatment naïve individual is an individual who has not received prior treatment for ES-SCLC. In some embodiments, the treatment-naïve individual is chemotherapy naïve, e.g., an individual who has not received prior chemotherapy for the treatment of, e.g., cancer, SCLC, and/or ES-SCLC. In some embodiments, the individual has not received treatment for ES-SCLC. In some embodiments, the individual has not received prior systemic treatment for ES-SCLC. In some embodiments the individual has received prior chemoradiotherapy for limited stage SCLC (LS-SCLC) with curative intent, and has experienced a treatment-free cycle of at least 6 months since the last chemotherapy, radiotherapy, or chemoradiotherapy cycle from the diagnosis of ES-SCLC. In some embodiments, the individual has asymptomatic supratentorial or cerebellar central nervous system (CNS) metastases. In some embodiments, the individual does not have metastases to the midbrain, pons, medulla, or spinal cord. In some embodiments, the individual has CNS disease and does not require corticosteroid treatment for CNS disease. In some embodiments, the individual has new asymptomatic metastases and has received radiation therapy and/or surgery for CNS metastases. In some embodiments, the individual has measurable disease, according to/as defined by RECIST v1.1 criteria (see, e.g., Eisenhauer et al. (2009) "New response evaluation criteria in solid tumors: Revised RECIST guideline (version 1.1)." Eur. J. Cancer. 45:228-247). In some embodiments, the individual has not received prior treatment with a CD137 agonist or an immune checkpoint blockade therapy, e.g., including, without limitation, an anti-PD-1 antibody or an anti-PD-L1 antibody.

Any of the PD-1 axis binding antagonists, platinum agents, and topoisomerase II inhibitors known in the art or described herein may be used in the methods. In some embodiments, the PD-1 axis binding antagonist is atezolizumab, the platinum agent is carboplatin or cisplatin, and/or the topoisomerase II inhibitor is etoposide.

In some embodiments, treatment comprises an induction phase and a maintenance phase (or "maintenance therapy").

In some embodiments, the induction phase comprises administering the PD-1 axis binding antagonist (e.g., an anti-PD-L1 antibody such as atezolizumab) at a dose of 1200 mg on Day 1, the platinum agent (e.g., carboplatin or cisplatin) at a dose sufficient to achieve an initial target Area Under the Curve (AUC) of 5 mg/mL/min on Day 1, and the topoisomerase II inhibitor (e.g., etoposide) at a dose of 100 mg/$m^2$ on each of Days 1, 2, and 3 of each 21-day cycle for Cycles 1-4. In some embodiments, the maintenance phase comprises administering the PD-1 axis binding antagonist (e.g., an anti-PD-L1 antibody such as atezolizumab) at a dose of 1200 mg on Day 1 of each 21-day cycle following Cycle 4. An exemplary dosing and administration schedule that comprises an induction cycle and a maintenance cycle is provided in Table 4 below:

TABLE 4

Exemplary Dosing and Administration Schedule

| Drugs (listed in order of administration) | Induction Phase Cycles 1-4* | | | Maintenance Phase >Cycle 4* |
|---|---|---|---|---|
| | Day 1 | Day 2 | Day 3 | Day 1 |
| 1) anti-PD-L1 Ab (atezolizumab) | 1200 mg | | | 1200 mg |
| 2) platinum agent (carboplatin or cisplatin) | AUC = 5‡ | | | |
| 3) topoisomerase II inhibitor (etoposide) | 100 mg/$m^2$ | 100 mg/$m^2$ | 100 mg/$m^2$ | |

*21-day cycles
‡mg/ml/min

In some embodiments, the 1200 mg dose of atezolizumab is equivalent to an average body weight-based dose of 15 m/kg. In some embodiments the dose of carboplatin needed to achieve an AUC of 5 mg/mL/min is calculated according to the Calvert formula (see, e.g., Calvert et al. (1989) "Carboplatin dosage: prospective evaluation of a simple formula based on renal function." J. Clin. Oncol. 7:1748-56; van Warmerdam et al. (1995) J. Cancer Res. Clin. Oncol. 121 (8): 478-486). For further details, see Example 1 below.

In some embodiments, the progression free survival (PFS) of the individual is measured according to RECIST v1.1 criteria, as described in Eisenhauer et al. (2009) "New response evaluation criteria in solid tumors: Revised RECIST guideline (Version 1.1)." Eur J Cancer. 45:228□47). In some embodiments, PFS is measured as the period of time from the start of treatment to the first occurrence of disease progression as determined by RECIST v1.1 criteria. In some embodiments, PFS is measured as the time from the start of treatment to the time of death. In some embodiments, the treatment increases the progression free survival (PFS) of the individual by at least about any one of 4.5, 4.75, 5, 5.25, 5.5, 5.75 or 6 months (including any range in between these values). In some embodiments, the treatment increases the progression free survival (PFS) of the individual by at least about 5.6 months. In some embodiments, the treatment increases the PFS of the individual by at least about any one of 0.5, 1, 1.25, 1.5, 1.75, 2, 2.25, 2.5, 2.75, or 3 months (including any range in between these values), as compared to an individual having lung cancer (such as small cell lung cancer, e.g., extensive stage small cell lung cancer) who received treatment with a platinum agent (e.g., carboplatin or cisplatin) and a topoisomerase II inhibitor (e.g., etoposide). In some embodiments, the treatment increases the PFS of the individual by at least about 1.1 months, as compared to an individual having lung cancer (such as small cell lung cancer, e.g., extensive stage small cell lung cancer) who received treatment with a platinum agent (e.g., carboplatin or cisplatin) and a topoisomerase II inhibitor (e.g., etoposide).

In some embodiments, overall survival (OS) is measured as the period of time from the start of treatment to death. In some embodiments, the treatment increases the OS of the individual by at least about any one of 10.5, 10.75, 11, 11.25, 11.5, 11.75, 12, 12.25, 12.5, 12.75, 13, 13.25, 13.5, 13.75, or 14 months (including any range in between these values). In some embodiments, the treatment extends OS by greater than 14 months, e.g., by about any one of 14.25, 14.5, 14.75, 15, 15.25, 15.5, 15.75 or more than 15.75 months (including any range in between these values). In some embodiments, the treatment extends OS by about 15.9 months. In some embodiments, the treatment increases the OS of the individual by at least about any one of 0.5, 1, 1.25, 1.5, 1.75, 2, 2.25, 2.5, 2.75, or 3 months (including any range in between these values), as compared to an individual having lung cancer (such as small cell lung cancer, e.g., extensive stage small cell lung cancer) who received treatment with a platinum agent (e.g., carboplatin or cisplatin) and a topoisomerase II inhibitor (e.g., etoposide). In some embodiments, the treatment increases the OS of the individual by more than about 3 months, e.g., by at least about any one of 4, 4.25, 4.5, 4.75, 5, 5.25, 5.5, 5.75, 6, 6.25, 6.5, or 6.75 months (including any range in between these values) as compared to an individual having lung cancer (such as small cell lung cancer, e.g., extensive stage small cell lung cancer) who received treatment with a platinum agent (e.g., carboplatin or cisplatin) and a topoisomerase II inhibitor (e.g., etoposide). In some embodiments, the treatment increases the OS of the individual by about 6.6 months, as compared to an individual having lung cancer (such as small cell lung cancer, e.g., extensive stage small cell lung cancer) who received treatment with a platinum agent (e.g., carboplatin or cisplatin) and a topoisomerase II inhibitor (e.g., etoposide).

In some embodiments, the individual is 65 years of age or older (e.g., between about 65 to about 74 years of age, between about 75 to about 84 years of age, or ≥85 years of age. In some embodiments, the individual has a blood tumor mutation burden (bTMB) of at least about 10, 11, 12, 13, 14, 15, or 16. In some embodiments, the individual has a blood tumor mutation burden (bTMB) greater than 16. bTMB represents the total number of mutations per coding area of a tumor genome calculated through the genomic sequencing of circulating tumor DNA (ctDNA) using well known methods.

In some embodiments, the individual reports relief from one or more lung cancer-related symptoms, e.g., at 12 weeks following the start of treatment. In some embodiments, lung-cancer related symptoms are one or more of arm pain, shoulder pain, chest pain, cough, and dyspnea (i.e., difficult or labored breathing).

In some embodiments, the individual is human.

In some embodiments, the individual has cancer that is resistant (has been demonstrated to be resistant) to one or more PD-1 axis antagonists. In some embodiments, resistance to PD-1 axis antagonist includes recurrence of cancer or refractory cancer. Recurrence may refer to the reappearance of cancer, in the original site or a new site, after treatment. In some embodiments, resistance to PD-1 axis antagonist includes progression of the cancer during treatment with the PD-1 axis antagonist. In some embodiments, resistance to PD-1 axis antagonist includes cancer that does not response to treatment. The cancer may be resistant at the beginning of treatment or it may become resistant during treatment. In some embodiments, the cancer is at early stage or at late stage.

In another aspect, the individual has cancer that expresses (has been shown to express e.g., in a diagnostic test) PD-L1 biomarker. In some embodiments, such individual is "PD-L1 positive" or has cancer that is a "PD-L1 positive cancer." In some embodiments, the individual is "PD-L1 positive" or has a "PD-L1 positive cancer" if PD-L1 expression (e.g., protein expression) is detected on (or in) tumor cells (TC) in a sample from the individual, or if PD-L1 expression (e.g., protein expression) is detected on (or in) tumor-infiltrating immune cells (IC) in a sample from the individual. In some embodiments, the individual's TC and/or IC express low levels of PD-L1 biomarker. In some embodiments, the individual's TC and/or IC express high levels PD-L1 biomarker. In some embodiments of any of the methods, assays and/or kits, the individual is "PD-L1 positive" or has cancer that is a "PD-L1 positive cancer" if the PD-L1 biomarker is present (e.g., detected, e.g., via IHC) in more than 0% of a sample, in at least 1% of a sample, in at least 5% of a sample, or in at least 10% of a sample from the individual (e.g., a sample from the individual that contains the individual's TC and/or IC). In some embodiments of any of the methods, assays and/or kits, the presence of the PD-L1 biomarker in a sample (e.g., in a sample from the individual that contains the individual's TC and/or IC) is detected as any level of staining in the sample.

In some embodiments of any of the methods, assays and/or kits, the PD-L1 biomarker is detected in the sample using a method selected from the group consisting of FACS, Western blot, ELISA, immunoprecipitation, immunohistochemistry, immunofluorescence, radioimmunoassay, dot blotting, immunodetection methods, HPLC, surface plasmon resonance, optical spectroscopy, mass spectrometery, HPLC, qPCR, RT-qPCR, multiplex qPCR or RT-qPCR, RNA-seq, microarray analysis, SAGE, MassARRAY technique, and FISH, and combinations thereof.

In some embodiments of any of the methods, assays and/or kits, the PD-L1 biomarker is detected in the sample by protein expression. In some embodiments, protein expression is determined by immunohistochemistry (IHC). In some embodiments, the PD-L1 biomarker is detected using an anti-PD-L1 antibody. In some embodiments, the PD-L1 biomarker is detected as a weak staining intensity by IHC. In some embodiments, the PD-L1 biomarker is detected as a moderate staining intensity by IHC. In some embodiments, the PD-L1 biomarker is detected as a strong staining intensity by IHC. In some embodiments, the PD-L1 biomarker is detected on tumor cells, tumor infiltrating immune cells, stromal cells and any combinations thereof. In some embodiments, the staining is membrane staining, cytoplasmic staining or combinations thereof.

In some embodiments, the PD-L1 biomarker is detected using an anti-PD-L1 rabbit monoclonal primary antibody. In some embodiments, the PD-L1 is detected in a formalin-fixed paraffin-embedded sample. In some embodiments, the anti-PD-L1 rabbit monoclonal primary antibody is detected with a secondary antibody comprising a detectable label. In some embodiments, the assay used to detect the PD-L1 is the VENTANA PD-L1 (SP142) assay (commercially available from VENTANTA®).

In another aspect, the individual has cancer that does not express PD-L1 biomarker or expresses very low levels of PD-L1 biomarker. In some embodiments, such individual is referred to as "PD-L1 negative" or is referred to as having "PD-L1 negative cancer." In some embodiments, the individual is "PD-L1 negative" or has a "PD-L1 negative cancer" if PD-L1 expression (e.g., protein expression) is not detected on (or in) tumor cells (TC) in a sample from the individual, if PD-L1 expression (e.g., protein expression) is not detected on (or in) tumor-infiltrating immune cells (IC) in a sample from the individual, or if PD-L1 expression (e.g., protein expression) is detected at very low levels on (or in) TC and/or IC in a sample from the individual. In some embodiments of any of the methods, assays and/or kits, the individual is "PD-L1 negative" or has a "PD-L1 negative cancer" if PD-L1 (e.g., PD-L1 expression) is detected (e.g., via IHC or other assay) in 0% of the TC and/or IC in a sample from the individual. In some embodiments of any of the methods, assays, and/or kits, the individual is "PD-L1 negative" or has a "PD-L1 negative cancer" if PD-L1 (e.g., PD-L1 expression) is detected (e.g., via IHC or other assay) in $<1\%$ of the TC and/or IC in a sample from the individual. In some embodiments of any of the methods, assays and/or kits, "PD-L1 negative" means that there is no staining in the sample e.g., in a sample from the individual that contains the individual's TC and/or IC.

The PD-1 axis binding antagonist (such as atezolizumab), the platinum agent (such as carboplatin) and the topoisomerase II inhibitor (such as etoposide) may be administered in any order. For example, PD-1 axis binding antagonist (such as atezolizumab), the platinum agent (such as carboplatin) and the topoisomerase II inhibitor (such as etoposide) may be administered sequentially (at different times) or concurrently (at the same time). In some embodiments, PD-1 axis binding antagonist (such as atezolizumab), the platinum agent (such as carboplatin) and the topoisomerase II inhibitor (such as etoposide) are in separate compositions. In some embodiments, one or more (or all three) of the PD-1 axis binding antagonist (such as atezolizumab), the platinum agent (such as carboplatin) and the topoisomerase II inhibitor (such as etoposide) are in the same composition.

The PD-1 axis binding antagonist (such as atezolizumab), the platinum agent (such as carboplatin) and the topoisomerase II inhibitor (such as etoposide) may be administered by the same route of administration or by different routes of administration. In some embodiments, the PD-1 axis binding antagonist is administered intravenously, intramuscularly, subcutaneously, topically, orally, transdermally, intraperitoneally, intraorbitally, by implantation, by inhalation, intrathecally, intraventricularly, or intranasally. In some embodiments, the platinum agent (such as carboplatin) is administered intravenously, intramuscularly, subcutaneously, topically, orally, transdermally, intraperitoneally, intraorbitally, by implantation, by inhalation, intrathecally, intraventricularly, or intranasally. In some embodiments, the topoisomerase II inhibitor (such as etoposide) is administered intravenously, intramuscularly, subcutaneously, topically, orally, transdermally, intraperitoneally, intraorbitally, by implantation, by inhalation, intrathecally, intraventricularly, or intranasally. In some embodiments, PD-1 axis binding antagonist (such as atezolizumab), the platinum agent (such as carboplatin) and the topoisomerase II inhibitor (such as etoposide) are administered via intravenous infusion. An effective amount of the PD-1 axis binding antagonist (such as atezolizumab), the platinum agent (such as carboplatin) and the topoisomerase II inhibitor (such as etoposide) may be administered for prevention or treatment of disease.

In some embodiments, provided is a method of treating extensive-stage small cell lung cancer (ES-SCLC) in an individual (e.g., an individual who is treatment-naïve for ES-SCLC) that comprises administering to the individual an effective amount of atezolizumab, carboplatin, and etoposide, wherein the administering comprises an induction phase and a maintenance phase, wherein the induction phase comprises administering the atezolizumab at a dose of 1200 mg on Day 1, the carboplatin at a dose sufficient to achieve an initial target Area Under the Curve (AUC) of 5 mg/mL/min on Day 1, and the etoposide at a dose of 100 mg/m$^2$ on each of Days 1, 2, and 3 of each 21-day cycle for Cycles 1-4; wherein the maintenance phase comprises. In some embodiments, the maintenance phase comprises administering the atezolizumab at a dose of 1200 mg on Day 1 of each 21-day cycle following Cycle 4. In some embodiments, the method extends the PFS of the individual (e.g., by at least about any one of 4.5, 4.75, 5, 5.25, 5.5, 5.75 or 6 months, including any range in between these values) and/or the OS of the individual (e.g., by at least about any one of 10.5, 10.75, 11, 11.25, 11.5, 11.75, 12, 12.25, 12.5, 12.75, 13, 13.25, 13.5, 13.75, or 14 months, including any range in between these values). In some embodiments, the method extends the PFS of the individual (e.g., by at least about any one of 0.5, 1, 1.25, 1.5, 1.75, 2, 2.25, 2.5, 2.75, or 3 months, including any range in between these values) and/or the OS of the individual (e.g., by at least about any one of 0.5, 1, 1.25, 1.5, 1.75, 2, 2.25, 2.5, 2.75, or 3 months, including any range in between these values), as compared to an individual having lung cancer (such as small cell lung cancer, e.g., extensive stage small cell lung cancer) who received treatment with a platinum agent (e.g., carboplatin or cisplatin) and a topoisomerase II inhibitor (e.g., etoposide).

In some embodiments, the administration of atezolizumab is followed by the administration of carboplatin, and the administration of carboplatin is followed by the administration of etoposide on Day 1 of each 21-day cycle for Cycles 1-4, e.g., as shown in Table 4 above.

In some embodiments, the atezolizumab is administered intravenously over 60 (+15 minutes) on Day 1, the carboplatin is administered intravenously over a period of 30-60 minutes on Day 1, and the etoposide is administered intravenously over a period of 60 minutes on Days 1, 2, and 3 for the first 21-day cycle (i.e., for Cycle 1). In some embodiments, the atezolizumab is administered intravenously over 30 (+10 minutes) on Day 1, the carboplatin is administered intravenously over a period of 30-60 minutes on Day 1, and the etoposide is administered intravenously over a period of 60 minutes on Days 1, 2, and 3 for each 21-day cycle for Cycles 2-4. In some embodiments, the atezolizumab is administered intravenously over 30 (+10 minutes) on Day 1 of each 21-day cycle following Cycle 4.

As a general proposition, the therapeutically effective amount of the antibody administered to human will be in the range of about 0.01 to about 50 mg/kg of patient body weight whether by one or more administrations. In some embodiments, the antibody used is about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.01 to about 5 mg/kg, or about 0.01 to about 1 mg/kg administered daily, for example. In some embodiments, the antibody is administered at 15 mg/kg. However, other dosage regimens may be useful. In one embodiment, an anti-PDL1 antibody described herein is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg or about 1400 mg on day 1 of 21-day cycles. The dose may be administered as a single dose or as multiple doses (e.g., 2 or 3 doses), such as infusions. The dose of the antibody administered in a combination treatment may be reduced as compared to a single treatment. The progress of this therapy is easily monitored by conventional techniques.

In some embodiments, the methods may further comprise an additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation.

In some embodiments, the additional therapy comprises CT-011 (also known as Pidilizumab or MDV9300; CAS Registry No. 1036730-42-3; CureTech/Medivation). CT-011, also known as hBAT or hBAT-1, is an antibody described in WO2009/101611. In some embodiments, the additional therapeutic comprises an antibody that comprises a heavy chain and a light chain sequence, wherein:

```
(a) the heavy chain comprises the amino acid
sequence:
                                     (SEQ ID NO: 19)
QVQLVQSGSELKKPGASVKISCKASGYTFTNYGMNWVRQAPGQGLQWMGW
INTDSGESTYAEEFKGRFVFSLDTSVNTAYLQITSLTAEDTGMYFCVRVG
YDALDYWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYIC
NVNHKPSNTKVDKRVEPKSCDKTHTCPPCPAPELLGGPSVFLFPPKPKDT
LMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK,
and

(b) the light chain comprises the amino acid
sequence:
                                     (SEQ ID NO: 20)
EIVLTQSPSLSASVGDRVTITCSARSSVSYMHWFQQKPGKAPKLWIYRTS
NLASGVPSRFSGSGSGTSYCLTINSLQPEDFATYYCQQRSSFPLTFGGGT
KLEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLS
SPVTKSFNRGEC.
```

In some embodiments, the additional therapeutic antibody comprises the six HVR sequences from SEQ ID NO:19 and SEQ ID NO:20 (e.g., the three heavy chain HVRs from SEQ ID NO: 19 and the three light chain HVRs from SEQ ID NO:20). In some embodiments, the additional therapeutic antibody comprises the heavy chain variable domain from SEQ ID NO:19 and the light chain variable domain from SEQ ID NO:20. Other additional therapeutic antibodies contemplated for use herein include, without limitation, alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), the antibody drug conjugate gemtuzumab ozogamicin (MYLOTARG®, Wyeth), apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories).

In some embodiments, the additional therapy is therapy targeting PI3K/AKT/mTOR pathway, HSP90 inhibitor, tubulin inhibitor, apoptosis inhibitor, and/or chemopreventative agent. In some embodiments, the additional therapy is CTLA-4 (also known as CD152), e.g., a blocking antibody, ipilimumab (also known as MDX-010, MDX-101, or Yervoy®), tremelimumab (also known as ticilimumab or CP-675,206), an antagonist directed against B7-H3 (also known as CD276), e.g., a blocking antibody, MGA271, an antagonist directed against a TGF beta, e.g., metelimumab (also known as CAT-192), fresolimumab (also known as GC1008), or LY2157299, a treatment comprising adoptive transfer of a T cell (e.g., a cytotoxic T cell or CTL) expressing a chimeric antigen receptor (CAR), a treatment comprising adoptive transfer of a T cell comprising a dominant-negative TGF beta receptor, e.g, a dominant-negative TGF beta type II receptor, a treatment comprising a HERCREEM protocol (see, e.g., ClinicalTrials.gov Identifier NCT00889954), an agonist directed against CD137 (also known as TNFRSF9, 4-1BB, or ILA), e.g., an activating antibody, urelumab (also known as BMS-663513), an agonist directed against CD40, e.g., an activating antibody, CP-870893, an agonist directed against OX40 (also known as CD134), e.g., an activating antibody, administered in conjunction with a different anti-OX40 antibody (e.g., AgonOX)., an agonist directed against CD27, e.g., an activating antibody, CDX-1127, indoleamine-2,3-dioxygenase (IDO), 1-methyl-D-tryptophan (also known as 1-D-MT), an antibody-drug conjugate (in some embodiments, comprising mertansine or monomethyl auristatin E (MMAE)), an anti-*NaPi*2b antibody-MMAE conjugate (also known as DNIB0600A or RG7599), trastuzumab emtansine (also known as T-DM1, ado-trastuzumab emtansine, or KADCYLA®, Genentech), DMUC5754A, an antibody-drug conjugate targeting the endothelin B receptor (EDNBR), e.g., an antibody directed against EDNBR conjugated with MMAE, an angiogenesis inhibitor, an antibody directed against a VEGF, e.g., VEGF-A, bevacizumab (also known as AVASTIN®, Genentech), an antibody directed against angiopoietin 2 (also known as Ang2), MEDI3617, an antineoplastic agent, an agent targeting CSF-1R (also known as M-CSFR or CD115), anti-CSF-1R (also known as IMC-CS4), an interferon, for example interferon alpha or interferon gamma, Roferon-A, GM-CSF (also known as recombinant human granulocyte macrophage colony stimulating factor, rhu GM-CSF, sargramostim, or Leukine®), IL-2 (also known as aldesleukin or Proleukin®), IL-12, an antibody targeting CD20 (in some embodiments, the antibody targeting CD20 is obinutuzumab (also known as GA101 or Gazyva®) or rituximab), an antibody targeting GITR (in some embodiments, the antibody targeting GITR is TRX518), in conjunction with a cancer vaccine (in some embodiments, the cancer vaccine is a peptide cancer vaccine, which in some embodiments is a personalized peptide vaccine; in some embodiments the peptide cancer vaccine is a multivalent long peptide, a multi-peptide, a peptide cocktail, a hybrid peptide, or a peptide-pulsed dendritic cell vaccine (see, e.g., Yamada et al., *Cancer Sci,* 104:14-21, 2013)), in conjunction with an adjuvant, a TLR agonist, e.g., Poly-ICLC (also known as Hiltonol®), LPS, MPL, or CpG ODN, tumor necrosis factor (TNF) alpha, IL-1, HMGB1, an IL-10 antagonist, an IL-4 antagonist, an IL-13 antagonist, an HVEM antagonist, an ICOS agonist, e.g., by administration of ICOS-L, or an agonistic antibody directed against ICOS, a treatment targeting CX3CL1, a treatment targeting CXCL10, a treatment targeting CCL5, an LFA-1 or ICAM1 agonist, a Selectin agonist, a targeted therapy, an inhibitor of B-Raf, vemurafenib (also known as Zelboraf®, dabrafenib (also known as Tafinlar®), erlotinib (also known as Tarceva®), an inhibitor of a MEK, such as MEK1 (also known as MAP2K1) or MEK2 (also known as MAP2K2). cobimetinib (also known as GDC-0973 or XL-518), trametinib (also known as Mekinist®), an inhibitor of K-Ras, an inhibitor of c-Met, onartuzumab (also known as MetMAb), an inhibitor of Alk, AF802 (also known as CH5424802 or alectinib), an inhibitor of a phosphatidylinositol 3-kinase (PI3K), BKM120, idelalisib (also known as GS-1101 or CAL-101), perifosine (also known as KRX-0401), an Akt, MK2206, GSK690693, GDC-0941, an inhibitor of mTOR, sirolimus (also known as rapamycin), temsirolimus (also known as CCI-779 or Torisel®), everolimus (also known as RAD001), ridaforolimus (also known as AP-23573, MK-8669, or deforolimus), OSI-027, AZD8055, INK128, a dual PI3K/mTOR inhibitor, XL765, GDC-0980, BEZ235 (also known as NVP-BEZ235), BGT226, GSK2126458, PF-04691502, PF-05212384 (also known as PKI-587). The additional therapy may be one or more of the chemotherapeutic agents described herein.

IX. Methods of Detection and Diagnosis

In some embodiments, the sample is obtained prior to treatment with a PD-1 axis binding antagonist (e.g., atezolizumab), a platinum agent (e.g., carboplatin), and a topoisomerase II inhibitor (e.g., etoposide). In some embodiments, the tissue sample is formalin fixed and paraffin embedded, archival, fresh or frozen In some embodiments, the sample is whole blood. In some embodiments, the whole blood comprises immune cells, circulating tumor cells and any combinations thereof.

Presence and/or expression levels/amount of a biomarker (e.g., PD-L1) can be determined qualitatively and/or quantitatively based on any suitable criterion known in the art, including but not limited to DNA, mRNA, cDNA, proteins, protein fragments and/or gene copy number. In certain embodiments, presence and/or expression levels/amount of a biomarker in a first sample is increased or elevated as compared to presence/absence and/or expression levels/amount in a second sample. In certain embodiments, presence/absence and/or expression levels/amount of a biomarker in a first sample is decreased or reduced as compared to presence and/or expression levels/amount in a second sample. In certain embodiments, the second sample is a reference sample, reference cell, reference tissue, control sample, control cell, or control tissue. Additional disclosures for determining presence/absence and/or expression levels/amount of a gene are described herein.

In some embodiments of any of the methods, elevated expression refers to an overall increase of about any of 10%, 20%, 30%, 40%, 50%, 60%, 70%, 80%, 90%, 95%, 96%, 97%, 98%, 99% or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue. In certain embodiments, the elevated expression refers to the increase in expression level/amount of a biomarker in the sample wherein the increase is at least about any of 1.5×, 1.75×, 2×, 3×, 4×, 5×, 6×, 7×, 8×, 9×, 10×, 25×, 50×, 75×, or 100× the expression level/amount of the respective biomarker in a reference sample, reference cell, reference tissue, control sample, control cell, or control tissue. In some embodiments, elevated expression refers to an overall increase of greater than about 1.5 fold, about 1.75 fold, about 2 fold, about 2.25 fold, about 2.5 fold, about 2.75 fold, about 3.0 fold, or about 3.25 fold as compared to a reference sample, reference cell, reference tissue, control sample, control cell, control tissue, or internal control (e.g., housekeeping gene).

In some embodiments of any of the methods, reduced expression refers to an overall reduction of about any of 10%, 20%, 30%, 40%, 50%, 60%, 70%, 80%, 90%, 95%, 96%, 97%, 98%, 99% or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue. In certain embodiments, reduced expression refers to the decrease in expression level/amount of a biomarker in the sample wherein the decrease is at least about any of 0.9×, 0.8×, 0.7×, 0.6×, 0.5×, 0.4×, 0.3×, 0.2×, 0.1×, 0.05×, or 0.01× the expression level/amount of the respective biomarker in a reference sample, reference cell, reference tissue, control sample, control cell, or control tissue.

Presence and/or expression level/amount of various biomarkers in a sample can be analyzed by a number of methodologies, many of which are known in the art and understood by the skilled artisan, including, but not limited to, immunohistochemistry ("IHC"), Western blot analysis, immunoprecipitation, molecular binding assays, ELISA, ELIFA, fluorescence activated cell sorting ("FACS"), MassARRAY, proteomics, quantitative blood based assays (as for example Serum ELISA), biochemical enzymatic activity assays, in situ hybridization, Southern analysis, Northern analysis, whole genome sequencing, polymerase chain reaction ("PCR") including quantitative real time PCR ("qRT-PCR") and other amplification type detection methods, such as, for example, branched DNA, SISBA, TMA and the like), RNA-Seq, FISH, microarray analysis, gene expression profiling, and/or serial analysis of gene expression ("SAGE"), as well as any one of the wide variety of assays that can be performed by protein, gene, and/or tissue array analysis. Typical protocols for evaluating the status of genes and gene products are found, for example in Ausubel et al., eds., 1995, *Current Protocols In Molecular Biology*, Units 2 (Northern Blotting), 4 (Southern Blotting), 15 (Immunoblotting) and 18 (PCR Analysis). Multiplexed immunoassays such as those available from Rules Based Medicine or Meso Scale Discovery ("MSD") may also be used.

In some embodiments, presence and/or expression level/amount of a biomarker is determined using a method comprising: (a) performing gene expression profiling, PCR (such as rtPCR or qRT-PCR), RNA-seq, microarray analysis, SAGE, MassARRAY technique, or FISH on a sample (such as a subject cancer sample); and b) determining presence and/or expression level/amount of a biomarker in the sample. In some embodiments, the microarray method comprises the use of a microarray chip having one or more nucleic acid molecules that can hybridize under stringent conditions to a nucleic acid molecule encoding a gene mentioned above or having one or more polypeptides (such as peptides or antibodies) that can bind to one or more of the proteins encoded by the genes mentioned above. In one embodiment, the PCR method is qRT-PCR. In one embodiment, the PCR method is multiplex-PCR. In some embodiments, gene expression is measured by microarray. In some embodiments, gene expression is measured by qRT-PCR. In some embodiments, expression is measured by multiplex-PCR.

Methods for the evaluation of mRNAs in cells are well known and include, for example, hybridization assays using complementary DNA probes (such as in situ hybridization using labeled riboprobes specific for the one or more genes, Northern blot and related techniques) and various nucleic acid amplification assays (such as RT-PCR using complementary primers specific for one or more of the genes, and other amplification type detection methods, such as, for example, branched DNA, SISBA, TMA and the like).

Samples from mammals can be conveniently assayed for mRNAs using Northern, dot blot or PCR analysis. In addition, such methods can include one or more steps that allow one to determine the levels of target mRNA in a biological sample (e.g., by simultaneously examining the levels a comparative control mRNA sequence of a "housekeeping" gene such as an actin family member). Optionally, the sequence of the amplified target cDNA can be determined.

Optional methods include protocols which examine or detect mRNAs, such as target mRNAs, in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes whose expression correlates with increased or reduced clinical benefit of anti-angiogenic therapy may be arrayed on a solid support. Hybridization of a labeled probe with a particular array member indicates that the sample from which the probe was derived expresses that gene.

According to some embodiments, presence and/or expression level/amount is measured by observing protein expression levels of an aforementioned gene. In certain embodiments, the method comprises contacting the biological sample with antibodies to a biomarker (e.g., anti-PD-L1 antibodies) described herein under conditions permissive for binding of the biomarker, and detecting whether a complex is formed between the antibodies and biomarker. Such method may be an in vitro or in vivo method. In one embodiment, an antibody is used to select subjects eligible for therapy with PD-L1 axis binding antagonist e.g., a biomarker for selection of individuals.

In certain embodiments, the presence and/or expression level/amount of biomarker proteins in a sample is examined using IHC and staining protocols. IHC staining of tissue sections has been shown to be a reliable method of determining or detecting presence of proteins in a sample. In some embodiments of any of the methods, assays and/or kits, the PD-L1 biomarker is PD-L1. In some embodiments, PD-L1 is detected by immunohistochemistry. In some embodiments, elevated expression of a PD-L1 biomarker in a sample from an individual is elevated protein expression and, in further embodiments, is determined using IHC. In one embodiment, expression level of biomarker is determined using a method comprising: (a) performing IHC analysis of a sample (such as a subject cancer sample) with an antibody; and b) determining expression level of a biomarker in the sample. In some embodiments, IHC staining intensity is determined relative to a reference. In some embodiments, the reference is a reference value. In some embodiments, the reference is a reference sample (e.g., control cell line staining sample or tissue sample from non-cancerous patient).

IHC may be performed in combination with additional techniques such as morphological staining and/or fluorescence in-situ hybridization. Two general methods of IHC are available; direct and indirect assays. According to the first assay, binding of antibody to the target antigen is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for IHC typically will be labeled with a detectable moiety. Numerous labels are available which can be generally grouped into the following categories: (a) Radioisotopes, such as 35S, 14C, 1251, 3H, and 131I; (b) colloidal gold particles; (c) fluorescent labels including, but are not limited to, rare earth chelates (europium chelates), Texas Red, rhodamine, fluorescein, dansyl, Lissamine, umbelliferone, phycocrytherin, phycocyanin, or commercially available fluorophores such SPECTRUM ORANGE7 and SPECTRUM GREEN7 and/or derivatives of any one or more of the above; (d) various enzyme-substrate labels are available and U.S. Pat. No. 4,275,149 provides a review of some of these. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

Examples of enzyme-substrate combinations include, for example, horseradish peroxidase (HRPO) with hydrogen peroxidase as a substrate; alkaline phosphatase (AP) with para-Nitrophenyl phosphate as chromogenic substrate; and β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase). For a general review of these, see U.S. Pat. Nos. 4,275,149 and 4,318,980.

In some embodiments of any of the methods, PD-L1 is detected by immunohistochemistry using an anti-PD-L1 diagnostic antibody (i.e., primary antibody). In some embodiments, the PD-L1 diagnostic antibody specifically binds human PD-L1. In some embodiments, the PD-L1 diagnostic antibody is a nonhuman antibody. In some embodiments, the PD-L1 diagnostic antibody is a rat, mouse, or rabbit antibody. In some embodiments, the PD-L1 diagnostic antibody is a monoclonal antibody. In some embodiments, the PD-L1 diagnostic antibody is directly labeled.

Specimens thus prepared may be mounted and coverslipped. Slide evaluation is then determined, e.g., using a microscope, and staining intensity criteria, routinely used in the art, may be employed. In one embodiment, it is understood that when cells and/or tissue from a tumor is examined using IHC, staining is generally determined or assessed in tumor cell and/or tissue (as opposed to stromal or surrounding tissue that may be present in the sample). In some embodiments, it is understood that when cells and/or tissue from a tumor is examined using IHC, staining includes determining or assessing in tumor infiltrating immune cells, including intratumoral or peritumoral immune cells.

In some embodiments, PDL1 expression is evaluated on a tumor or tumor sample. As used herein, a tumor or tumor sample may encompass part or all of the tumor area occupied by tumor cells. In some embodiments, a tumor or tumor sample may further encompass tumor area occupied by tumor associated intratumoral cells and/or tumor associated stroma (e.g., contiguous peri-tumoral desmoplastic stroma). Tumor associated intratumoral cells and/or tumor associated stroma may include areas of immune infiltrates (e.g., tumor infiltrating immune cells as described herein) immediately adjacent to and/or contiguous with the main tumor mass. In some embodiments, PDL1 expression is evaluated on tumor cells. In some embodiments, PDL1 expression is evaluated on immune cells within the tumor area as described above, such as tumor infiltrating immune cells.

In alternative methods, the sample may be contacted with an antibody specific for said biomarker under conditions sufficient for an antibody-biomarker complex to form, and then detecting said complex. The presence of the biomarker may be detected in a number of ways, such as by Western blotting and ELISA procedures for assaying a wide variety of tissues and samples, including plasma or serum. A wide range of immunoassay techniques using such an assay format are available, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labeled antibody to a target biomarker.

Presence and/or expression level/amount of a selected biomarker in a tissue or cell sample may also be examined by way of functional or activity-based assays. For instance, if the biomarker is an enzyme, one may conduct assays known in the art to determine or detect the presence of the given enzymatic activity in the tissue or cell sample.

In certain embodiments, the samples are normalized for both differences in the amount of the biomarker assayed and variability in the quality of the samples used, and variability between assay runs. Such normalization may be accomplished by detecting and incorporating the expression of certain normalizing biomarkers, including well known housekeeping genes. Alternatively, normalization can be based on the mean or median signal of all of the assayed genes or a large subset thereof (global normalization approach). On a gene-by-gene basis, measured normalized amount of a subject tumor mRNA or protein is compared to the amount found in a reference set. Normalized expression levels for each mRNA or protein per tested tumor per subject can be expressed as a percentage of the expression level measured in the reference set. The presence and/or expression level/amount measured in a particular subject sample to be analyzed will fall at some percentile within this range, which can be determined by methods well known in the art.

In one embodiment, the sample is a clinical sample. In another embodiment, the sample is used in a diagnostic assay. In some embodiments, the sample is obtained from a primary or metastatic tumor. Tissue biopsy is often used to obtain a representative piece of tumor tissue. Alternatively, tumor cells can be obtained indirectly in the form of tissues or fluids that are known or thought to contain the tumor cells of interest. For instance, samples of lung cancer lesions may be obtained by resection, bronchoscopy, fine needle aspiration, bronchial brushings, or from sputum, pleural fluid or blood. Genes or gene products can be detected from cancer or tumor tissue or from other body samples such as urine, sputum, serum or plasma. The same techniques discussed above for detection of target genes or gene products in cancerous samples can be applied to other body samples. Cancer cells may be sloughed off from cancer lesions and appear in such body samples. By screening such body samples, a simple early diagnosis can be achieved for these cancers. In addition, the progress of therapy can be monitored more easily by testing such body samples for target genes or gene products.

In certain embodiments, a reference sample, reference cell, reference tissue, control sample, control cell, or control tissue is a single sample or combined multiple samples from the same subject or individual that are obtained at one or more different time points than when the test sample is obtained. For example, a reference sample, reference cell, reference tissue, control sample, control cell, or control tissue is obtained at an earlier time point from the same subject or individual than when the test sample is obtained. Such reference sample, reference cell, reference tissue, control sample, control cell, or control tissue may be useful if the reference sample is obtained during initial diagnosis of cancer and the test sample is later obtained when the cancer becomes metastatic.

In certain embodiments, a reference sample, reference cell, reference tissue, control sample, control cell, or control tissue is a combined multiple samples from one or more healthy individuals who are not the subject or individual. In certain embodiments, a reference sample, reference cell, reference tissue, control sample, control cell, or control tissue is a combined multiple samples from one or more individuals with a disease or disorder (e.g., cancer) who are not the subject or individual. In certain embodiments, a reference sample, reference cell, reference tissue, control sample, control cell, or control tissue is pooled RNA samples from normal tissues or pooled plasma or serum samples from one or more individuals who are not the subject or individual. In certain embodiments, a reference sample, reference cell, reference tissue, control sample, control cell, or control tissue is pooled RNA samples from tumor tissues or pooled plasma or serum samples from one or more individuals with a disease or disorder (e.g., cancer) who are not the subject or individual.

In some embodiments, the sample is a tissue sample from the individual. In some embodiments, the tissue sample is a tumor tissue sample (e.g., biopsy tissue). In some embodiments, the tissue sample is lung tissue. In some embodiments, the tissue sample is renal tissue. In some embodiments, the tissue sample is skin tissue. In some embodiments, the tissue sample is pancreatic tissue. In some embodiments, the tissue sample is gastric tissue. In some embodiments, the tissue sample is bladder tissue. In some embodiments, the tissue sample is esophageal tissue. In some embodiments, the tissue sample is mesothelial tissue. In some embodiments, the tissue sample is breast tissue. In some embodiments, the tissue sample is thyroid tissue. In some embodiments, the tissue sample is colorectal tissue. In some embodiments, the tissue sample is head and neck tissue. In some embodiments, the tissue sample is osteosarcoma tissue. In some embodiments, the tissue sample is prostate tissue. In some embodiments, the tissue sample is ovarian tissue, HCC (liver), blood cells, lymph nodes, and/or bone/bone marrow tissue. In some embodiments, the tissue sample is colon tissue. In some embodiments, the tissue sample is endometrial tissue. In some embodiments, the tissue sample is brain tissue (e.g., glioblastoma, neuroblastoma, and so forth).

In some embodiments, a tumor tissue sample (the term "tumor sample" is used interchangeably herein) may encompass part or all of the tumor area occupied by tumor cells. In some embodiments, a tumor or tumor sample may further encompass tumor area occupied by tumor associated intratumoral cells and/or tumor associated stroma (e.g., contiguous peri-tumoral desmoplastic stroma). Tumor associated intratumoral cells and/or tumor associated stroma may include areas of immune infiltrates (e.g., tumor infiltrating immune cells as described herein) immediately adjacent to and/or contiguous with the main tumor mass.

In some embodiments of any of the methods, the disease or disorder is a tumor. In some embodiments, the tumor is a malignant cancerous tumor (i.e., cancer). In some embodiments, the tumor and/or cancer is a solid tumor or a non-solid or soft tissue tumor. Examples of soft tissue tumors include leukemia (e.g., chronic myelogenous leukemia, acute myelogenous leukemia, adult acute lymphoblastic leukemia, acute myelogenous leukemia, mature B-cell acute lymphoblastic leukemia, chronic lymphocytic leukemia, polymphocytic leukemia, or hairy cell leukemia) or lymphoma (e.g., non-Hodgkin's lymphoma, cutaneous T-cell lymphoma, or Hodgkin's disease). A solid tumor includes any cancer of body tissues other than blood, bone marrow, or the lymphatic system. Solid tumors can be further divided into those of epithelial cell origin and those of non-epithelial cell origin. Examples of epithelial cell solid tumors include tumors of the gastrointestinal tract, colon, colorectal (e.g., basaloid colorectal carcinoma), breast, prostate, lung, kidney, liver, pancreas, ovary (e.g., endometrioid ovarian carcinoma), head and neck, oral cavity, stomach, duodenum, small intestine, large intestine, anus, gall bladder, labium, nasopharynx, skin, uterus, male genital organ, urinary organs (e.g., urothelium carcinoma, dysplastic urothelium carcinoma, transitional cell carcinoma), bladder, and skin. Solid tumors of non-epithelial origin include sarcomas, brain tumors, and bone tumors. In some embodiments, the cancer isnon-small cell lung cancer (NSCLC). In some embodiments, the cancer is second-line or third-line locally advanced or metastatic non-small cell lung cancer. In some embodiments, the cancer is adenocarcinoma. In some embodiments, the cancer is squamous cell carcinoma. In some embodiments, the cancer is non-small cell lung cancer (NSCLC), glioblastoma, neuroblastoma, melanoma, breast carcinoma (e.g. triple-negative breast cancer), gastric cancer, colorectal cancer (CRC), or hepatocellular carcinoma. In some embodiments, the cancer is a primary tumor. In some embodiments, the cancer is a metastatic tumor at a second site derived from any of the above types of cancer.

In some embodiments of any of the methods, the cancer displays human effector cells (e.g., is infiltrated by human effector cells). Methods for detecting human effector cells are well known in the art, including, e.g., by IHC. In some embodiments, the cancer display high levels of human effector cells. In some embodiments, human effector cells are one or more of NK cells, macrophages, monocytes. In some embodiments, the cancer is any cancer described herein. In some embodiments, the cancer is non-small cell lung cancer (NSCLC), glioblastoma, neuroblastoma, melanoma, breast carcinoma (e.g. triple-negative breast cancer), gastric cancer, colorectal cancer (CRC), or hepatocellular carcinoma.

In some embodiments of any of the methods, the cancer displays cells expressing FcR (e.g., is infiltrated by cells expressing FcR). Methods for detecting FcR are well known in the art, including, e.g., by IHC. In some embodiments, the cancer display high levels of cells expressing FcR. In some embodiments, FcR is FcγR. In some embodiments, FcR is activating FcγR. In some embodiments, the cancer is non-small cell lung cancer (NSCLC), glioblastoma, neuroblastoma, melanoma, breast carcinoma (e.g. triple-negative breast cancer), gastric cancer, colorectal cancer (CRC), or hepatocellular carcinoma.

In some embodiments, the PD-L1 biomarker is detected in the sample using a method selected from the group consisting of FACS, Western blot, ELISA, immunoprecipitation, immunohistochemistry, immunofluorescence, radioimmunoassay, dot blotting, immunodetection methods, HPLC, surface plasmon resonance, optical spectroscopy, mass spectrometery, HPLC, qPCR, RT-qPCR, multiplex qPCR or RT-qPCR, RNA-seq, microarray analysis, SAGE, MassARRAY technique, and FISH, and combinations thereof. In some embodiments, the PD-L1 biomarker is detected using FACS analysis. In some embodiments, the PD-L1 biomarker is PD-L1. In some embodiments, the PD-L1 expression is detected in blood samples. In some embodiments, the PD-L1 expression is detected on circulating immune cells in blood samples. In some embodiments, the circulating immune cell is a CD3+/CD8+ T cell. In some embodiments, prior to analysis, the immune cells are isolated from the blood samples. Any suitable method to isolate/enrich such population of cells may be used including, but not limited to, cell sorting. In some embodiments, the PD-L1 expression is elevated in samples from individuals that respond to treatment with an inhibitor of the PD-L1/PD-1 axis pathway, such as an anti-PD-L1 antibody. In some embodiments, the PD-L1 expression is elevated on the circulating immune cells, such as the CD3+/CD8+ T cells, in blood samples.

Certain aspects of the present disclosure relate to measurement of the expression level of one or more genes or one or more proteins in a sample. In some embodiments, a sample may include leukocytes. In some embodiments, the sample may be a peripheral blood sample (e.g., from a patient having a tumor). In some embodiments, the sample is a tumor sample. A tumor sample may include cancer cells, lymphocytes, leukocytes, stroma, blood vessels, connective tissue, basal lamina, and any other cell type in association with the tumor. In some embodiments, the sample is a tumor tissue sample containing tumor-infiltrating leukocytes. In some embodiments, the sample may be processed to separate or isolate one or more cell types (e.g., leukocytes). In some embodiments, the sample may be used without separating or isolating cell types.

A tumor sample may be obtained from a subject by any method known in the art, including without limitation a biopsy, endoscopy, or surgical procedure. In some embodiments, a tumor sample may be prepared by methods such as freezing, fixation (e.g., by using formalin or a similar fixative), and/or embedding in paraffin wax. In some embodiments, a tumor sample may be sectioned. In some embodiments, a fresh tumor sample (i.e., one that has not been prepared by the methods described above) may be used. In some embodiments, a tumor sample may be prepared by incubation in a solution to preserve mRNA and/or protein integrity.

In some embodiments, the sample may be a peripheral blood sample. A peripheral blood sample may include white blood cells, PBMCs, and the like. Any technique known in the art for isolating leukocytes from a peripheral blood sample may be used. For example, a blood sample may be drawn, red blood cells may be lysed, and a white blood cell pellet may be isolated and used for the sample. In another example, density gradient separation may be used to separate leukocytes (e.g., PBMCs) from red blood cells. In some embodiments, a fresh peripheral blood sample (i.e., one that has not been prepared by the methods described above) may be used. In some embodiments, a peripheral blood sample may be prepared by incubation in a solution to preserve mRNA and/or protein integrity.

In some embodiments, responsiveness to treatment may refer to any one or more of: extending survival (including overall survival and progression free survival); resulting in an objective response (including a complete response or a partial response); or improving signs or symptoms of cancer. In some embodiments, responsiveness may refer to improvement of one or more factors according to the published set of RECIST guidelines for determining the status of a tumor in a cancer patient, i.e., responding, stabilizing, or progressing. For a more detailed discussion of these guidelines, see Eisenhauer et al., Eur J Cancer 2009; 45:228-47; Topalian et al., N Engl J Med 2012; 366:2443-54; Wolchok et al., Clin Can Res 2009; 15:7412-20; and Therasse, P., et al. J. Natl. Cancer Inst. 92:205-16 (2000). A responsive subject may refer to a subject whose cancer(s) show improvement, e.g., according to one or more factors based on RECIST criteria. A non-responsive subject may refer to a subject whose cancer(s) do not show improvement, e.g., according to one or more factors based on RECIST criteria.

Conventional response criteria may not be adequate to characterize the anti-tumor activity of immunotherapeutic agents, which can produce delayed responses that may be preceded by initial apparent radiological progression, including the appearance of new lesions. Therefore, modified response criteria have been developed that account for the possible appearance of new lesions and allow radiological progression to be confirmed at a subsequent assessment. Accordingly, in some embodiments, responsiveness may refer to improvement of one of more factors according to immune-related response criteria2 (irRC). See, e.g., Wolchok et al., Clin Can Res 2009; 15:7412-20. In some embodiments, new lesions are added into the defined tumor burden and followed, e.g., for radiological progression at a subsequent assessment. In some embodiments, presence of non-target lesions are included in assessment of complete response and not included in assessment of radiological progression. In some embodiments, radiological progression may be determined only on the basis of measurable disease and/or may be confirmed by a consecutive assessment ≥4 weeks from the date first documented.

In some embodiments, responsiveness may include immune activation. In some embodiments, responsiveness may include treatment efficacy. In some embodiments, responsiveness may include immune activation and treatment efficacy.

X. Articles of Manufacture or Kits

In another embodiment of the invention, an article of manufacture or a kit is provided comprising a PD-1 axis binding antagonist (such as atezolizumab), a platinum agent (such as carboplatin) and/or a topoisomerase II inhibitor (such as etoposide). In some embodiments, the article of manufacture or kit further comprises package insert comprising instructions for using the PD-1 axis binding antagonist in conjunction with the platinum agent (such as carboplatin) and the topoisomerase II inhibitor (such as etoposide) to treat or delay progression of cancer (e.g., lung cancer, such as small cell lung cancer (SCLC), including extensive stage small cell lung cancer (ES-SCLC)) in an individual or to enhance immune function of an individual having cancer (e.g., lung cancer, such as small cell lung cancer (SCLC), including extensive stage small cell lung cancer (ES-SCLC)). Any of the PD-1 axis binding antagonist, platinum agent, and topoisomerase II inhibitor known in the art may be included in the article of manufacture or kits. In some embodiments, the kit comprises atezolizumab, carboplatin, and etoposide.

In some embodiments, the PD-1 axis binding antagonist (such as atezolizumab), the platinum agent (such as carboplatin) and the topoisomerase II inhibitor (such as etoposide) are in the same container or separate containers. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agent include, for example, bottles, vials, bags and syringes.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

EXAMPLES

The present disclosure will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: A Phase I/III, Randomized, Double-Blind, Placebo-Controlled Study of Carboplatin Plus Etoposide with or without Atezolizumab (Anti-PD-L1 Antibody) in Patients with Untreated Extensive-Stage Small Cell Lung Cancer (ES-SCLC)

This study was designed to evaluate whether the anti-tumor effect seen in atezolizumab-treated patients would translate into statistically significant and clinically relevant improvement in PFS and OS when used in combination with carboplatin and etoposide, compared with placebo, carboplatin, and etoposide in patients with chemotherapy-naive ES-SCLC. This study allowed for the evaluation of efficacy of atezolizumab in the ITT population and for the evaluation of exploratory immune endpoints such as, but not limited to a retrospective evaluation by PD-L1 expression and their association with patient outcomes.

Study Objectives

The primary efficacy objectives of this study were the following:

- To evaluate the efficacy of atezolizumab+carboplatin+etoposide compared with placebo+carboplatin+etoposide in the intent-to-treat (ITT) population as measured by investigator-assessed progression-free survival (PFS) according to RECIST v1.1 (see, e.g., Eisenhauer et al. (2009) "New response evaluation criteria in solid tumors: Revised RECIST guideline (Version 1.1)." *Eur J Cancer.* 45:228-47).
- To evaluate the efficacy of atezolizumab+carboplatin+etoposide compared with placebo+carboplatin+etoposide in the ITT population as measured by overall survival (OS).

The secondary efficacy objectives of this study were the following:

- To evaluate the efficacy of atezolizumab+carboplatin+etoposide compared with placebo+carboplatin+etoposide in the ITT population as measured by investigator-assessed overall response rate (ORR) according to RECIST v1.1.
- To evaluate the efficacy of atezolizumab+carboplatin+etoposide compared with placebo+carboplatin+etoposide in the ITT population as measured by investigator-assessed duration of response (DOR) according to RECIST v1.1.
- To evaluate the PFS rate at 6 months and at 1 year in each treatment arm for the ITT population. To evaluate the OS rate at 1 and 2 years in each treatment arm for the ITT population.
- To determine the impact of atezolizumab as measured by time to deterioration (TTD) in patient-reported lung cancer symptoms of cough, dyspnea (single-item and multi-item subscales), chest pain, arm/shoulder pain, or fatigue using the European Organization for the Research and Treatment of Cancer (EORTC) Quality of Life Questionnaire-Core 30 (QLQ-C30) and the supplemental lung cancer module (QLQ-LC13) in patients treated with atezolizumab+carboplatin+etoposide compared with placebo+carboplatin+etoposide in the ITT population.

The safety objectives for this study were the following:

- To evaluate the safety and tolerability of atezolizumab in combination with carboplatin+etoposide compared with carboplatin+etoposide.
- To evaluate the incidence and titers of anti-therapeutic antibodies (ATAs) against atezolizumab and to explore the potential relationship of the immunogenicity response with pharmacokinetics, safety, and efficacy.

The pharmacokinetic objective for this study is to characterize the pharmacokinetics of atezolizumab, carboplatin, and etoposide in chemotherapy-naive patients with ES-SCLC.

The exploratory objectives for this study were the following:

To evaluate investigator-assessed PFS, ORR, and DOR modified RECIST for the atezolizumab-containing treatment arm in the ITT population.

To evaluate the relationship between tumor biomarkers (including but not limited to PD-L1, PD-1, somatic mutations, and others), as defined by immunohistochemistry (IHC) or quantitative reverse transcriptase-polymerase chain reaction (qRT-PCR), next generation sequencing (NGS), and/or other methods and measures of efficacy.

To assess predictive, prognostic, and pharmacodynamic exploratory biomarkers in archival and/or fresh tumor tissue, blood, plasma and serum and their association with disease status, mechanisms of resistance, and/or response to study treatment.

To evaluate and compare patient's health status as assessed by the EuroQOL 5 Dimensions 5-Level (EQ-5D-5L) questionnaire to generate utility scores for use in economic models for reimbursement.

To determine the impact of atezolizumab+carboplatin+etoposide compared with placebo+carboplatin+etoposide as measured by change from baseline in patient-reported outcomes (PRO) of health-related quality of life, lung cancer related symptoms, physical functioning, and health status as assessed by the European Organization for Research and Treatment of Cancer Quality of Life Questionnaires EORTC QLQ-C30 and LC13.

To evaluate the impact of chemotherapy (both carboplatin and etoposide) on peripheral and tumor-specific T-cell populations during and after induction therapy and its relationship to efficacy and safety outcomes.

Study Design

Figure 1B:
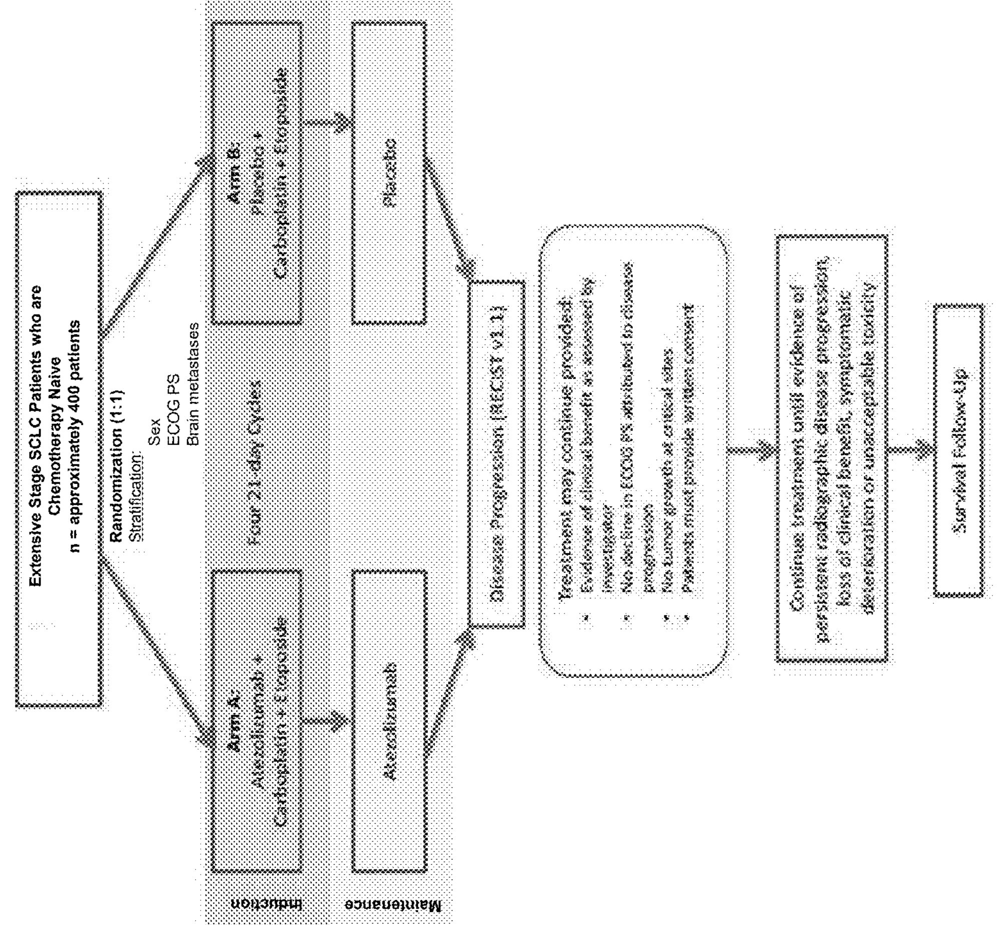
FIG. 1B provides a schematic of additional details regarding the study design.

Described below are the details of a randomized, Phase I/III, multicenter, double-blinded, placebo-controlled study designed to evaluate the safety and efficacy of atezolizumab in combination with carboplatin+etoposide compared with treatment with placebo+carboplatin+etoposide in patients who have ES-SCLC and were chemotherapy-naive for their extensive-stage disease. FIG. 1A illustrates the study design. Additional details regarding the study design are provided in FIG. 1B.

Eligible patients were stratified by sex (male vs. female), ECOG (i.e., Eastern Cooperative Oncology Group) performance status (0 vs. 1), and presence of brain metastases (yes vs. no) and randomized 1:1 to receive one of the following treatment regimens as shown in Table 5. Further details regarding ECOG performance status are provided in Oken et al. (1982) *Am J Clin Oncol.* 5:649-655).

TABLE 5

Study Treatment Arms

| TREATMENT ARM | INDUCTION PHASE (Four 21-Day Cycles) | MAINTENANCE PHASE (All 21-Day Cycles after Cycle 4) |
|---|---|---|
| A (201 patients) | atezolizumab + carboplatin + etoposide | atezolizumab |
| B (202 patients) | placebo + carboplatin + etoposide | placebo |

Induction treatment was administered on a 21-day cycle for four cycles. Following the induction phase, patients continued maintenance therapy with either atezolizumab (Arm A) or placebo (Arm B). During the maintenance phase, prophylactic cranial irradiation was permitted as per local standard-of-care and was reported on the Prophylactic Cranial Irradiation electronic Case Report Form (eCRF). Thoracic radiation with curative intent or the intent to eliminate residual disease was not permitted. Palliative thoracic radiation was allowed. The dosing and administration schedule for the treatment regimens in Table 5 are provided in Table 6 below:

TABLE 6

Dosing and Administration Schedule for Treatment Regimens

| Drugs (listed in order of administration) | Induction Phase Cycles 1-4* Day 1 | Day 2 | Day 3 | Maintenance Phase >Cycle 4* Day 1 |
|---|---|---|---|---|
| 1) atezolizumab (Arm A) or placebo (Arm B) | 1200 mg | | | 1200 mg |
| 2) carboplatin | AUC = 5‡ | | | |
| 3) etoposide | 100 mg/$m^2$ | 100 mg/$m^2$ | 100 mg/$m^2$ | |

*21-day cycles
‡mg/ml/min

If clinically feasible, it was recommended that patients undergo a tumor biopsy sample collection at the time of radiographic disease progression. These data were used to explore whether radiographic findings were consistent with the presence of a tumor. Additionally, these data were analyzed to evaluate the association between changes in tumor tissue and clinical outcome and to further understand the potential mechanisms of progression and resistance to atezolizumab as compared with such mechanisms after treatment with chemotherapy alone. This exploratory biomarker evaluation was not used for any treatment-related decisions.

All patients underwent tumor assessments at baseline and every 6 weeks (±7 days) for 48 weeks following Cycle 1, Day 1, regardless of treatment dose delays. After completion of the Week 48 tumor assessment, tumor assessments were required every 9 weeks (±7 days) thereafter, regardless of treatment dose delays. Patients underwent tumor assessments until radiographic disease progression per RECIST v1.1, withdrawal of consent, study termination by the Sponsor, or death, whichever occurred first.

Patients who continued treatment beyond radiographic disease progression per RECIST v1.1 continued to undergo tumor assessments every 6 weeks (±7 days), or sooner if symptomatic deterioration occurred. For these patients, tumor assessments continued every 6 weeks (±7 days), regardless of time in the study, until study treatment was discontinued.

Patients who discontinued treatment for reasons other than radiographic disease progression per RECIST v1.1 (e.g., toxicity, symptomatic deterioration) continued scheduled tumor assessments at the same frequency as would have been followed if the patient had remained on study treatment (i.e., every 6 weeks [±7 days] for 48 weeks following Cycle 1, Day 1 and then every 9 weeks [±7 days] thereafter, regardless of treatment dose delays) until radiographic disease progression per RECIST v1.1, withdrawal of consent, study termination by the Sponsor, or death, whichever occurred first, regardless of whether patients started a new anti-cancer therapy.

In case of an early termination of the study, patients who were deriving clinical benefit from treatment with atezolizumab were permitted to continue treatment with atezolizumab at the discretion of the investigator.

Outcome Measures

The primary efficacy outcome measures for this study were:

- PFS, defined as the time from randomization to the first occurrence of disease progression as determined by the investigator using RECIST v1.1 or death from any cause, whichever occurs first.
- OS, defined as the time from randomization to death from any cause.

The secondary efficacy outcome measures for this study were:

- Objective response, defined as PR or CR as determined by the investigator according to RECIST v1.1.
- Duration of response (DOR), defined as the time interval from first occurrence of a documented objective response to the time of disease progression as determined by the investigator using RECIST v1.1 or death from any cause, whichever came first.
- PFS rates at 6 months and at 1 year.
- OS rates at 1 and 2 years.
- Time to deterioration (TTD) in patient-reported lung cancer symptoms, defined as time from randomization to deterioration (10-point change) on each of the EORTC QLQ-C30 (European Organization for Research and Treatment of Cancer Quality of Life Questionnaire C30) and EORTC QLQ-LC13 symptom subscales (see Berman et al. (1994) *Eur J Cancer.* 30A (5): 635-42) maintained for two assessments or one assessment followed by death from any cause within 3 weeks.

The safety outcome measures for this study were:

- Incidence, nature, and severity of adverse events graded according to the National Cancer Institute Common Terminology Criteria for Adverse Events (NCI CTCAE) v4.0.
- Changes in vital signs, physical findings, and clinical laboratory results during and following study treatment administration.
- Incidence of anti-therapeutic antibody (ATA) response to atezolizumab and potential correlation with PK, pharmacodynamic, safety, and efficacy parameters.

The pharmacokinetic outcome measures for this study were:

- Maximum observed serum atezolizumab concentration ($C_{max}$) after infusion.
- Minimum observed serum atezolizumab concentration ($C_{min}$) prior to infusion at selected cycles, at treatment discontinuation, and at 120 days (±30 days) after the last dose of atezolizumab.
- Plasma concentrations for carboplatin.
- Plasma concentrations for etoposide.

The exploratory outcome measures for this study were:

- Objective response, PFS, and DOR as determined by the investigator according to modified RECIST.
- Status of PD-L1-, immune-, and SCLC-related and other exploratory biomarkers in archival and/or freshly obtained tumor tissues, and blood (or blood derivatives) collected before, during, or after treatment with atezolizumab or at progression and association with disease status and/or response to atezolizumab.
- Utility scores of the EQ-5D-5L (i.e., a standardized instrument for measuring generic health status; see The EuroQol Group (1990) Health Policy 16 (3): 199-208).
- Change from baseline in PROs of health-related quality of life, lung cancer-related symptoms, physical functioning, and health status as assessed by the EORTC QLQ-C30 and QLQ-LC13.
- Changes in levels and type of peripheral and tumor-specific T-cell populations during and after induction therapy and its relationship to efficacy and safety outcomes.

Patients

Patients were eligible for participation in this study if they were chemotherapy-naive and had ES-SCLC.

Inclusion Criteria

The key inclusion criteria were an age 18 years or older; ECOG performance status of 0 or 1; histologically or cytologically confirmed ES-SCLC (per the Veterans Administration Lung Study Group (VALG) staging system; (Micke et al. (2002) "Staging small cell lung cancer: Veterans Administration Lung Study Group versus International Association for the Study of Lung Cancer—what limits limited disease?" *Lung Cancer* 37:271-6); no prior systemic treatment for ES-SCLC; patients who had received prior chemoradiotherapy for limited-stage SCLC must have been treated with curative intent and must have experienced a treatment-free interval of at least 6 months since last chemotherapy, radiotherapy, or chemoradiotherapy cycle from diagnosis of extensive-stage SCLC; patients with a history of treated asymptomatic CNS metastases were eligible only if (a) the metastases were supratentorial and/or cerebellar (i.e., no metastases to midbrain, pons, medulla or spinal cord); (b) the patients had no ongoing requirement for corticosteroids as therapy for CNS disease, (c) patients had no evidence of interim progression between the completion of CNS-directed therapy and randomization, and (d) patients with new asymptomatic CNS metastases detected at the screening scan must receive radiation therapy and/or surgery for CNS metastases; measurable disease, as defined by RECIST v1.1 (previously irradiated lesions were only considered as measurable disease if disease progression had been unequivocally documented at that site since radiation and the previously irradiated lesion was not the only site of disease); adequate hematologic and end organ function, defined by the following laboratory test results obtained within 14 days prior to randomization:

- ANC ≥1500 cells/μL without granulocyte colony-stimulating factor support.
- Lymphocyte count ≥500/μL.
- count ≥100,000/μL without transfusion.
- Hemoglobin ≥9.0 g/dL. (Patients were permitted to be transfused to meet this criterion.)
- INR or aPTT ≤1.5×upper limit of normal (ULN). (This applied only to patients who were not receiving therapeutic anticoagulation; patients receiving therapeutic anticoagulation were required to be on a stable dose.)
- AST, ALT, and alkaline phosphatase ≤2.5×ULN, with the following exceptions:
    - Patients with documented liver metastases: AST and/or ALT ≤5×ULN.
    - Patients with documented liver or bone metastases: alkaline phosphatase ≤5×ULN.
- Serum bilirubin ≤1.25×ULN. (Patients with known Gilbert disease who had serum bilirubin level ≤3×ULN were enrolled.)
- Serum creatinine ≤1.5×ULN.

Patients were required to submit a pre-treatment tumor tissue sample before or within 4 weeks after randomization. (Any available tumor tissue sample could be submitted.)

Exclusion Criteria

Key exclusion criteria included: active or untreated CNS metastases as determined by computed tomography (CT) or magnetic resonance imaging (MRI) evaluation during screening and prior radiographic assessments; spinal cord compression not definitively treated with surgery and/or radiation or previously diagnosed and treated spinal cord compression without evidence that disease has been clinically stable for ≥1 week prior to randomization; leptomeningeal disease; uncontrolled pleural effusion, pericardial effusion, or ascites requiring recurrent drainage procedures (once monthly or more frequently, but patients with indwelling catheters (e.g., PleurX®) were allowed regardless of drainage frequency); uncontrolled or symptomatic hypercalcemia (patients who were receiving denosumab prior to randomization were, if eligible, required to discontinue its use and replace it with a bisphosphonate while in the study); malignancies other than SCLC within 5 years prior to randomization, with the exception of those with a negligible risk of metastasis or death (e.g., expected 5-year OS >90%) treated with expected curative outcome (such as adequately treated carcinoma in situ of the cervix, basal or squamous-cell skin cancer, localized prostate cancer treated surgically with curative intent, ductal carcinoma in situ treated surgically with curative intent); women who were pregnant, lactating, or intending to become pregnant during the study; history of autoimmune disease, including but not limited to myasthenia gravis, myositis, autoimmune hepatitis, systemic lupus erythematosus, rheumatoid arthritis, inflammatory bowel disease, vascular thrombosis associated with antiphospholipid syndrome, Wegener's granulomatosis, Sjögren's syndrome, Guillain-Barré syndrome, multiple sclerosis, vasculitis, or glomerulonephritis (patients with a history of autoimmune-related hypothyroidism on thyroid replacement hormone therapy were eligible; patients with controlled Type I diabetes mellitus on an insulin regimen were eligible); history of idiopathic pulmonary fibrosis, organizing pneumonia (e.g., bronchiolitis obliterans), drug-induced pneumonitis, idiopathic pneumonitis, or evidence of active pneumonitis on screening chest CT scan. (History of radiation pneumonitis in the radiation field (fibrosis) was permitted); positive test result for HIV; patients with active hepatitis B (chronic or acute; defined as having a positive hepatitis B surface antigen [HBsAg] test result at screening) or hepatitis C virus (HCV); active tuberculosis; severe infections at the time of randomization, including but not limited to hospitalization for complications of infection, bacteremia, or severe pneumonia; significant cardiovascular disease, such as New York Heart Association cardiac disease (Class II or greater), myocardial infarction, or cerebrovascular accident within 3 months prior to randomization, unstable arrhythmias, or unstable angina. (Patients with known coronary artery disease, congestive heart failure not meeting the above criteria, or left ventricular ejection fraction <50% were required to be on a stable medical regimen that is optimized in the opinion of the treating physician, in consultation with a cardiologist if appropriate); major surgical procedure other than for diagnosis within 28 days prior to randomization or anticipation of need for a major surgical procedure during the course of the study; prior allogeneic bone marrow transplantation or solid organ transplant; any other diseases, metabolic dysfunction, physical examination finding, or clinical laboratory finding giving reasonable suspicion of a disease or condition that contraindicated the use of an investigational drug or that may have affected the interpretation of the results or rendered the patient at high risk for treatment complications; patients with illnesses or conditions that interfere with their capacity to understand, follow, and/or comply with study procedures; treatment with any other investigational agent with therapeutic intent within 28 days prior to randomization; administration of a live, attenuated vaccine within 4 weeks before randomization or anticipation that such a live attenuated vaccine would be required during the study; prior treatment with CD137 agonists or immune checkpoint blockade therapies, anti-PD-1, and anti-PD-L1 therapeutic antibodies; treatment with systemic immunosuppressive medications (including, but not limited to corticosteroids, cyclophosphamide, azathioprine, methotrexate, thalidomide, and antitumor necrosis factor [anti-TNF] agents) within 1 week prior to randomization; history of severe allergic, anaphylactic, or other hypersensitivity reactions to chimeric or humanized antibodies or fusion proteins; known hypersensitivity or allergy to biopharmaceuticals produced in Chinese hamster ovary cells or any component of the atezolizumab formulation; and history of allergic reactions to carboplatin or etoposide.

Method of Treatment 403 patients were randomized (1:1) to receive treatment with atezolizumab+carboplatin+etoposide (Arm A) or placebo+carboplatin+etoposide (Arm B). (The details of Treatment Arms A and B are shown above in Table 5). Patient disposition is shown in Table 7 below, and patient demographics and baseline characteristics are shown in Table 8 below. (In Tables 7 and 8, PBO+CE="placebo+carboplatin+etoposide." Atezo+CE="atezolizumab +carboplatin+etoposide."

TABLE 7

Patient Disposition

| ITT (N = 403) | PBO + CE (N = 202) | Atezo + CE (N = 201) |
|---|---|---|
| Received Treatment | 197 (97.5%) | 197 (98.0%) |
| On Study | 60 (29.7%) | 77 (38.3%) |
| Alive: in treatment | 11 (5.4%) | 23 (11.4%) |
| Alive: in follow-up | 49 (24.3%) | 54 (26.9%) |
| Discontinued Study | 142 (70.3%) | 124 (61.7%) |
| Death | 132 (65.3%) | 101 (50.2%) |
| Lost to Follow-Up | 1 (0.5%) | 3 (1.5%) |
| Physician Decision | 0 | 2 (1.0%) |
| Withdrawal by Subject | 9 (4.5%) | 18 (9.0%) |

TABLE 8

Patient Demographics and Baseline Characteristics

| Demographics/Baseline characteristics | | PBO = CE (N = 202) | Atezo + CE (N = 201) |
|---|---|---|---|
| Age (yrs) | <65 | 106 (52.5%) | 111 (55.2%) |
| Sex (IxRS) | Male | 132 (65.3%) | 130 (64.7%) |
| Race | White | 159 (78.7%) | 163 (81.1%) |
| | Asian | 36 (17.8%) | 33 (16.4%) |
| | Other | 7 (3.5%) | 5 (2.5%) |
| Tobacco Use History | Never | 3 (1.5%) | 9 (4.5%) |
| Brain mets (IxRS) | Yes | 16 (7.9%) | 16 (8.0%) |
| Baseline ECOG (IxRS) | 1 | 130 (64.4%) | 128 (63.7%) |
| bTMB | >=16 | 40 (22.5%) | 40 (23.1%) |
| | >=10 | 110 (61.8%) | 102 (59.0%) |
| SLD at baseline | Mean (SD) | 116.58 (58.28) | 120.90 (58.88) |
| | Median | 105.5 | 113.0 |

Patients received their first dose of study drug on the day of randomization, if possible. If this was not possible, the first dose occurred within 5 days after randomization. Atezolizumab and placebo were supplied by the Sponsor.

Carboplatin and etoposide were background treatment and were considered non-investigational medicinal products (NIMPs). Carboplatin and etoposide were used in the commercially available formulations.

The induction phase of the study consisted of four cycles of atezolizumab/placebo plus chemotherapy, with each cycle being 21 days in duration. See FIG. 1. On Day 1 of each cycle, all eligible patients were administered study drug infusions in the following order:

Arm A: atezolizumab→carboplatin→etoposide

Arm B: placebo→carboplatin→etoposide

During the induction phase, study treatment was administered in the following manner on Day 1:

1. Atezolizumab/placebo (1200 mg, equivalent to an average body weight-based dose of 15 mg/kg), administered intravenously over 60 (±15) minutes (for the first infusion and shortening to 30 [±10] minutes for subsequent infusions), followed by
2. Carboplatin, administered intravenously over 30-60 minutes to achieve an initial target area under the concentration-time curve (AUC) of 5 mg/mL/min (Calvert formula dosing), followed by
3. Etoposide (100 mg/$m^2$), administered intravenously over 60 minutes.

The carboplatin dose of AUC 5 was calculated using the Calvert formula (Calvert et al. (1989) *J Clin Oncol* 7:1748-56):

Calvert Formula:

$$\text{Total dose (mg)} = (\text{target } AUC) \times (\text{glomerular filtration rate}[GFR] + 25)$$

The GFR used in the Calvert formula to calculate AUC-based dosing was not to exceed 125 mL/min. For the purposes of this protocol, the GFR was considered to be equivalent to the creatinine clearance (CRCL). The CRCL is calculated by institutional guidelines or by the method described in Cockcroft and Gault (1976) *Nephron* 16:31-41, using the following formula:

$$CRCL = \frac{(140-\text{age})(\text{wt})}{72 \times Scr} (\times 0.85 \text{ if female})$$

Where: CRCL=creatinine clearance in mL/min age=patient's age in years wt=patient's weight in kg Scr=serum creatinine in mg/dL For patients with an abnormally low serum creatinine level, estimate the GFR was estimated through use of a minimum creatinine level of 0.8 mg/dL or the estimated GFR was capped at 125 mL/min. It was recommended that physicians cap the dose of carboplatin for desired exposure (AUC) to avoid potential toxicity due to overdosing. On the basis of the Calvert formula described in the carboplatin label, the maximum doses were calculated as follows:

$$\text{Maximum carboplatin dose (mg)} = \text{target } AUC \text{ (mg} \times \text{min/mL)} \times (GFR + 25 \text{ mL/min})$$

The maximum dose was based on a GFR estimate that is capped at 125 mL/min for patients with normal renal function. No higher estimated GFR values were used. For a target AUC=5, the maximum dose was 5×150=750 mg. For a target AUC=4, the maximum dose was 4×150=600 mg. Additional details regarding carboplatin dosing are provide in: www(dot)fda(dot)gov/aboutfda/centersoffices/officeofmedicalproductsandtobacco/cder/ucm228 974.htm During the induction phase, etoposide (100 mg/$m^2$) was also administered intravenously over 60 minutes on Days 2 and 3. Cycles in which no chemotherapy was given did not count toward the total number of induction chemotherapy cycles. After the induction phase, patients began maintenance therapy with atezolizumab/placebo (i.e., 1200 mg, infused, as described above, on Day 1 of every subsequent 21-day cycle, see FIG. 1 and the study schema above). No dose modifications to atezolizumab/placebo were permitted.

Tumor and Response Evaluations

Screening assessments included computer tomography (CT) scans (with oral/IV contrast unless contraindicated) or magnetic resonance images (MRIs) of the chest and abdomen. A CT or MRI scan of the pelvis was required at screening and as clinically indicated or as per local standard-of-care at subsequent response evaluations. Spiral CT scans of the chest were obtained, if possible, but were not a requirement.

A CT (with contrast if not contraindicated) or MRI scan of the head was required at screening to evaluate CNS metastasis in all patients. An MRI scan of the brain was required to confirm or refute the diagnosis of CNS metastases at baseline in the event of an equivocal scan. Patients with active or untreated CNS metastases were not eligible for the study (see Exclusion Criteria).

If a CT scan for tumor assessment was performed in a positron emission tomography (PET)/CT scanner, the CT acquisition was required to be consistent with the standards for a full contrast diagnostic CT scan.

Bone scans and CT scans of the neck were also performed if clinically indicated. At the investigator's discretion, other methods of assessment of measurable disease as per RECIST v1.1 were used.

It was permissible to use tumor assessments performed as standard-of-care prior to obtaining informed consent and within 28 days of Cycle 1, Day 1 rather than repeating tests. Documentation of all known sites of disease at screening was required, and documentation reassessed at each subsequent tumor evaluation. The same radiographic procedure used to assess disease sites at screening should was throughout the study (e.g., the same contrast protocol for CT scans). Response was assessed by the investigator using RECIST v1.1 (see Eisenhauer et al. (2009) New response evaluation criteria in solid tumors: Revised RECIST guideline (Version 1.1). *Eur J Cancer.* 45:228-47) and modified RECIST criteria. Modified RECIST criteria were derived from RECIST v1.1 (Eisenhauer et al.; Topalian et al. (2012) N Engl J Med. 366:2443-54; and Wolchok et al. (2009) Clin Can Res 15:7412-20) and immune-related response criteria (Wolchoik et al.; Nishino et al. (2014) J Immunother Can. 2:17; and Nishino et al. (2013) Clin Can Res. 19:3936-43). Assessments were performed by the same evaluator, if possible, to ensure internal consistency across visits. Results were reviewed by the investigator before dosing at the next cycle.

Patients underwent tumor assessments at baseline and every 6 weeks (±7 days) for 48 weeks following Cycle 1, Day 1, regardless of treatment dose delays. After completion of the Week 48 tumor assessment, tumor assessments were required every 9 weeks (±7 days) thereafter, regardless of treatment dose delays. Patients underwent tumor assessments until radiographic disease progression per RECIST v1.1, withdrawal of consent, study termination by the Sponsor, or death, whichever occurred first. Patients who continued treatment beyond radiographic disease progression per RECIST v1.1 continued to undergo tumor assessments every 6 weeks (±7 days), or sooner if symptomatic deterioration occurred. For these patients, tumor assessments continued every 6 weeks (±7 days) regardless of time in the study, until study treatment was discontinued.

Patients who discontinued treatment for reasons other than radiographic disease progression per RECIST v1.1 (e.g., toxicity, symptomatic deterioration) continued scheduled tumor assessments at the same frequency as would have been followed if the patient had remained on study treatment (i.e., every 6 weeks [±7 days] for 48 weeks following Cycle 1, Day 1 and then every 9 weeks [±7 days] thereafter, regardless of treatment dose delays) until radiographic disease progression per RECIST v1.1, withdrawal of consent, study termination by Sponsor, or death, whichever occurred first, regardless of whether patients started a new anti-cancer therapy.

Results

The results of the study are presented in Table 9 below:

TABLE 9

Summary of Primary Efficacy Endpoints

| | ITT | PBO + CE (N = 202) | Atezo + CE (N = 201) |
|---|---|---|---|
| OS | Median (months) | 10.3 | 12.3 |
| | Stratified HR (95% CI) | 0.7 (0.54, 0.91) | |
| | Stratified Log rank p | p = 0.0069 | |
| PFS | Median (months) | 4.3 | 5.2 |
| | Stratified HR (95% CI) | 0.77 (0.62, 0.96) | |
| | Stratified Log rank p | p = 0.017 | |

Table 9 shows that the study met its co-primary endpoints of overall survival (OS) and investigator-assessed progression-free survival (PFS) per RCECIST v1.1. Overall survival improvement is statistically significant and clinically meaningful.

Figure 2:
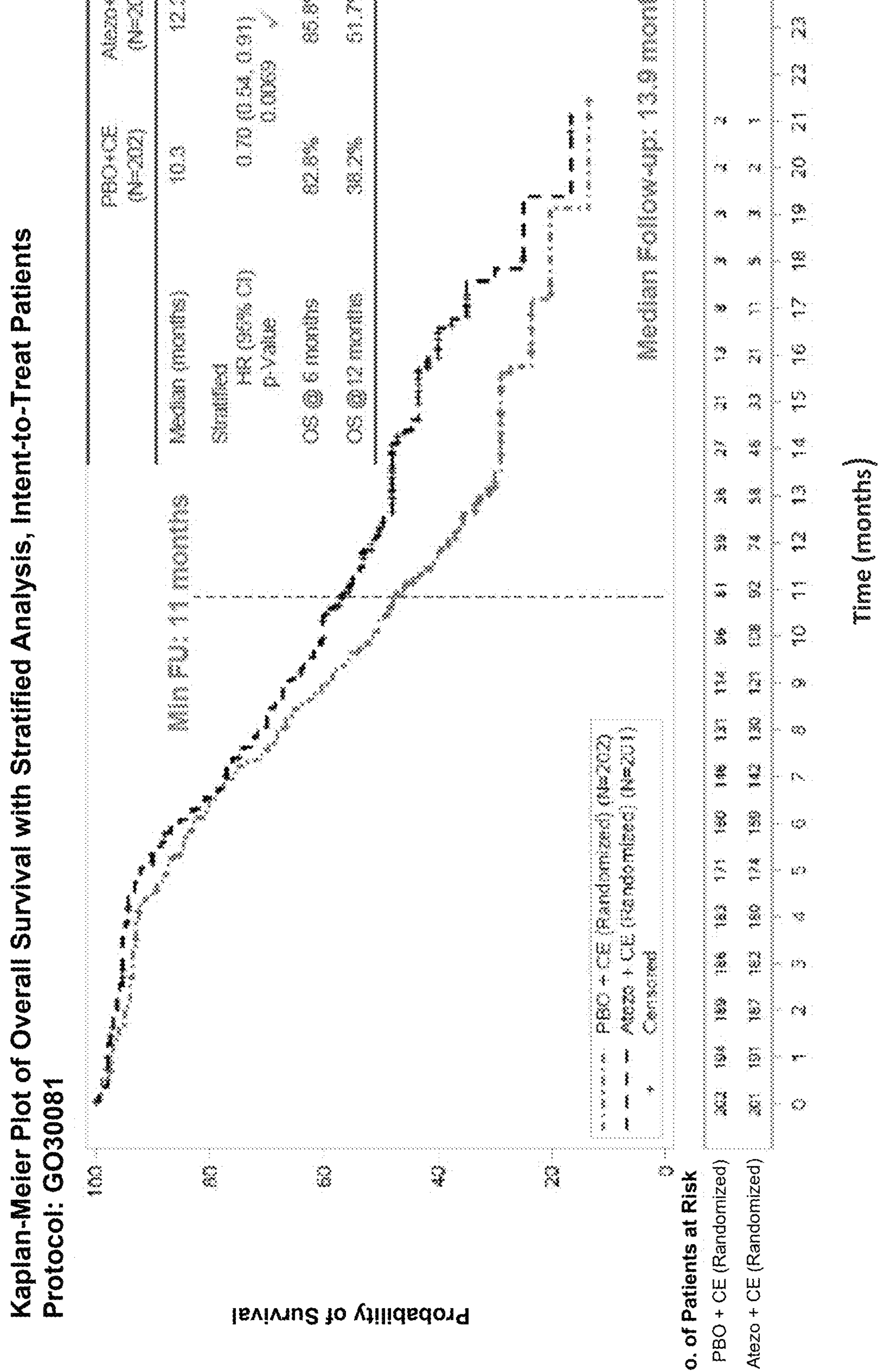
FIG. 2 provides a Kaplan-Meier Plot of overall survival (OS) of patients in Arm A (atezolizumab+carboplatin+etoposide) vs. Arm B (placebo+carboplatin+etoposide).
Figure 3:
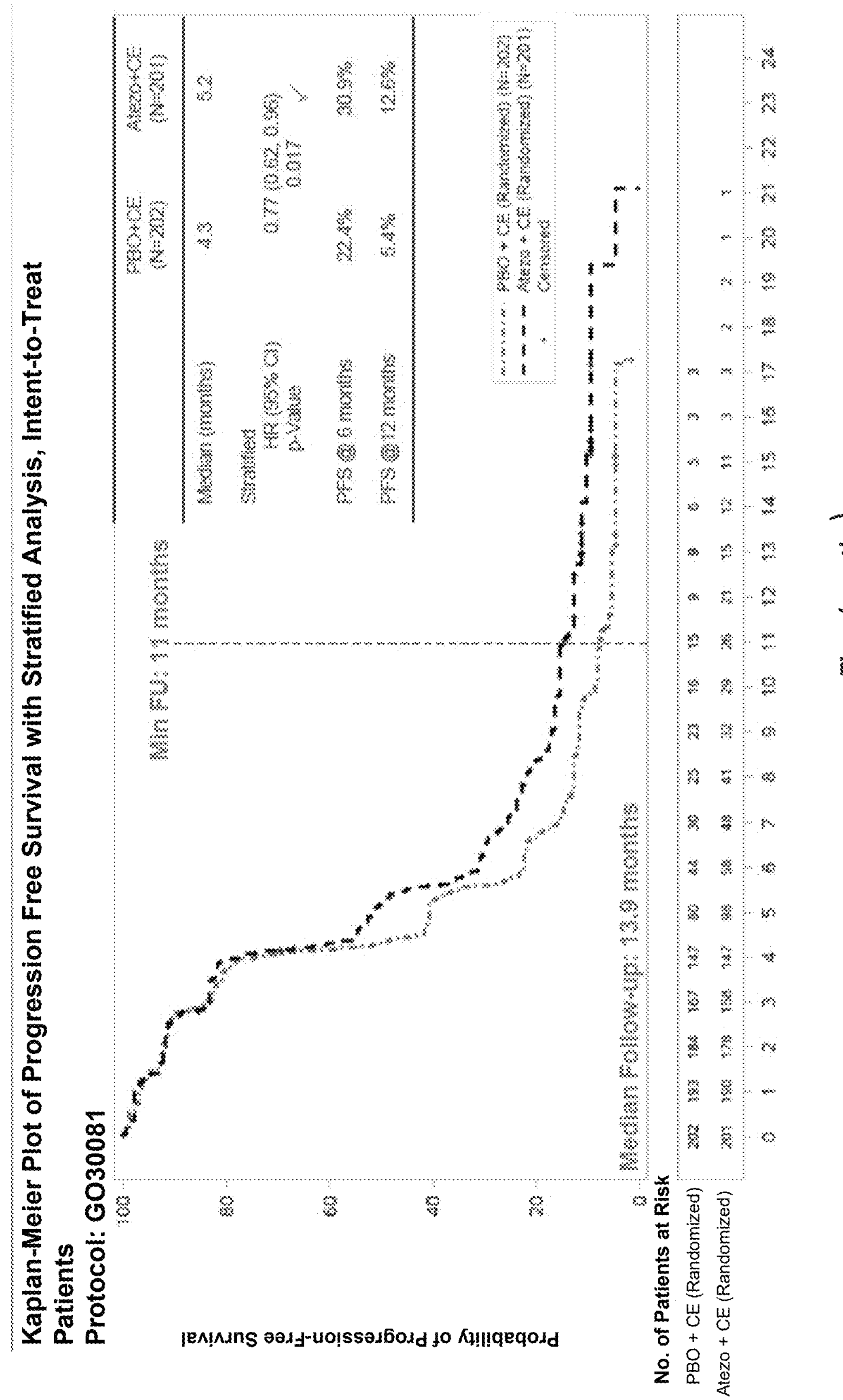
FIG. 3 provides a Kaplan-Meier Plot of progression-free survival (PFS) of patients in Arm A (atezolizumab+carboplatin+etoposide) vs. Arm B (placebo+carboplatin+etoposide).

Patients treated with Atezo+CE demonstrated extended overall survival as compared to patients treated with Placebo+CE. See FIG. 2. The 6 month OS of patients receiving Atezo+CE was 85.8% vs. 82.8% in patients receiving Placebo+CE. The 12 month OS of patients receiving Atezo+CE was 51.7% vs. 38.2% in patients receiving Placebo+CE. Patients treated with Atezo+CE also demonstrated extended progression-free survival as compared to patients treated with Placebo+CE. See FIG. 3. The 6 month PFS of patients receiving Atezo+CE was 30.9% vs. 22.4% in patients receiving Placebo+CE. The 12 month PFS of patients receiving Atezo+CE was 12.6% vs. 5.4% in patients receiving Placebo+CE.

The one-year overall survival rate of patients treated with Atezo+CE was 51.7%, whereas the one-year overall survival rate of patients receiving Placebo+CE was 38.2%.

Figure 4:
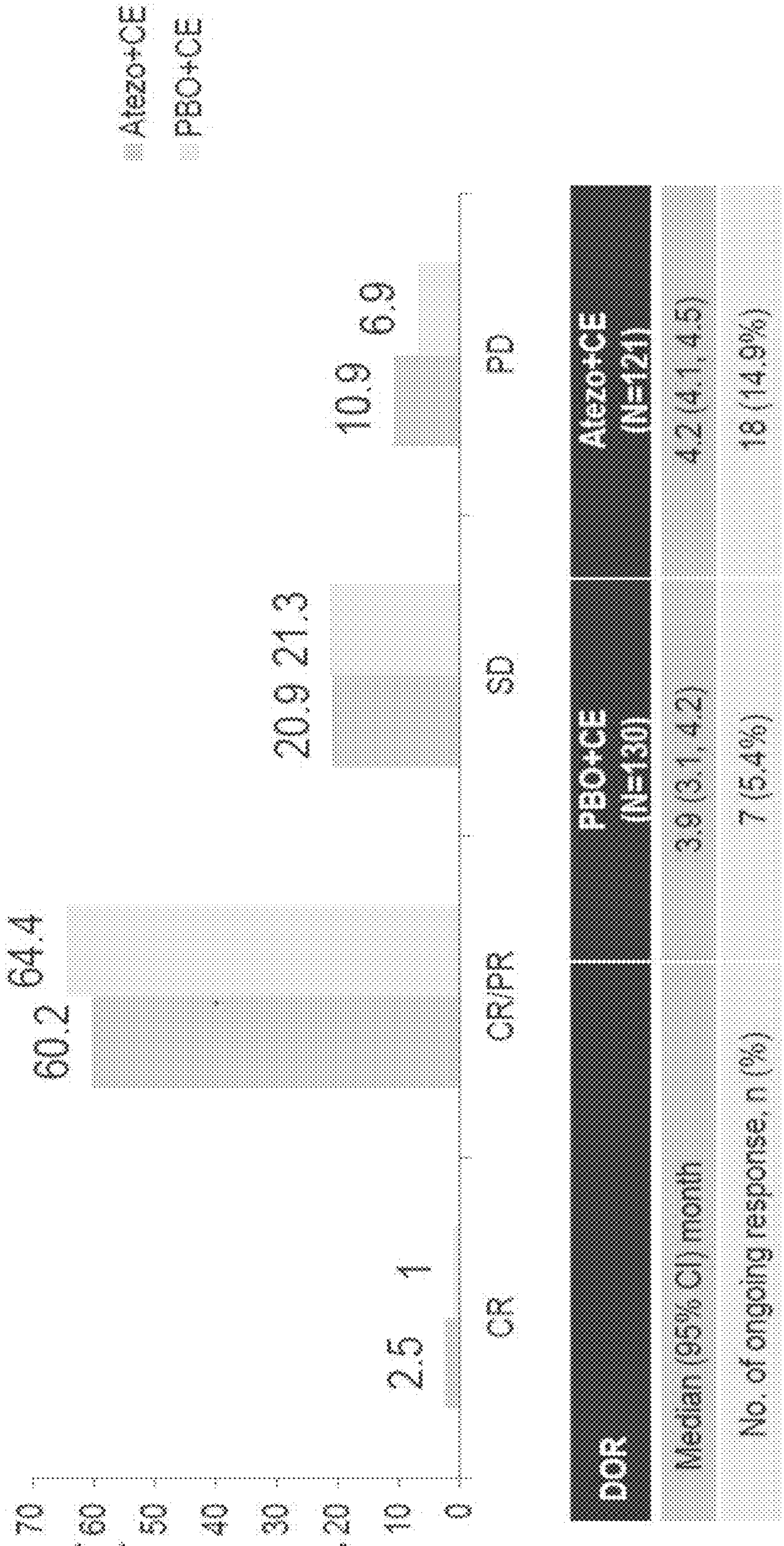
FIG. 4 provides a comparison of overall response rate (ORR) and duration of response (DOR) in patients in Arm A. vs. Arm B. (CR=complete response; CR/PR=complete response/partial response; SD=stable disease; PD=progressive disease.) ORR and DOR were assessed according to RECIST v1.1 criteria.

In addition, the overall response rates (ORR) were similar between the two treatment arms, with confirmed ORR of 60% in patients receiving atezolizumab+carboplatin+etoposide vs. 64% in patients receiving placebo+carboplatin+etoposide (CR: 2.5% in the atzeolizumab+carboplatin+etoposide arm vs. 1% in the placebo+carboplatin+etoposide arm). See FIG. 4 (CR=complete response; CR/PR=complete response/partial response; SD=stable disease; PD =progressive disease.) See also Table 10 below. Duration of response (DOR) was also similar between the two treatment arms, with a median DOR of 4.2 months in the atzeolizumab+carboplatin+etoposide arm vs. 3.9 months in the placebo+carboplatin+etoposide arm. ORR and DOR were assessed according to RECIST v1.1 criteria.

TABLE 10

Confirmed Investigator-Assessed Objective Response Rate and Duration of Response (Intention-to-Treat Population with Measurable Disease at Baseline).

| Variable | Atezolizumab Group | Placebo Group |
|---|---|---|
| Response† | | |
| No. of evaluable patients | 201 | 202 |
| Objective confirmed response-no. (%) | 121 (60.2 [53.1-67.0]) | 130 (64.4 [57.3-71.0]) |
| Complete | 5 (2.5 [0.8-5.7]) | 2 (1.0 [0.1-3.5]) |
| Partial | 116 (57.7 [50.6-64.6]) | 128 (63.4 [56.3-70.0]) |
| Stable disease-no. (% [95% CI]) | 42 (20.9 [15.5-27.2]) | 43 (21.3 [15.9-27.6]) |
| Progressive disease-no. (% [95% CI]) | 22 (10.9 [7.0-16.1]) | 14 (6.9 [3.8-11.4]) |
| Patients with missing data or who could not be evaluated-no. (%) | 16 (8.0) | 15 (7.4) |
| Duration of response‡ | | |
| No. of evaluations patients | 121 | 130 |
| Median duration of response (range)-mo | 4.2 (1.4+–19.5) | 3.9 (2.0–16.1+) |
| Patients with ongoing response at data cutoff date-no. (%) | 18 (14.9) | 7 (5.4) |

†Objective response was defined as complete response or partial response as determined by the investigator according to RECIST v1.1 criteria.
‡Duration of response was assessed among patients who had an objective response and was defined as the time from first occurrence of a documented objective response to the time of disease progression as determined by the investigator using RECIST or death from any cause, whichever occurred first.
+denotes a censored observation; CI denotes confidence interval.

Figure 5A:
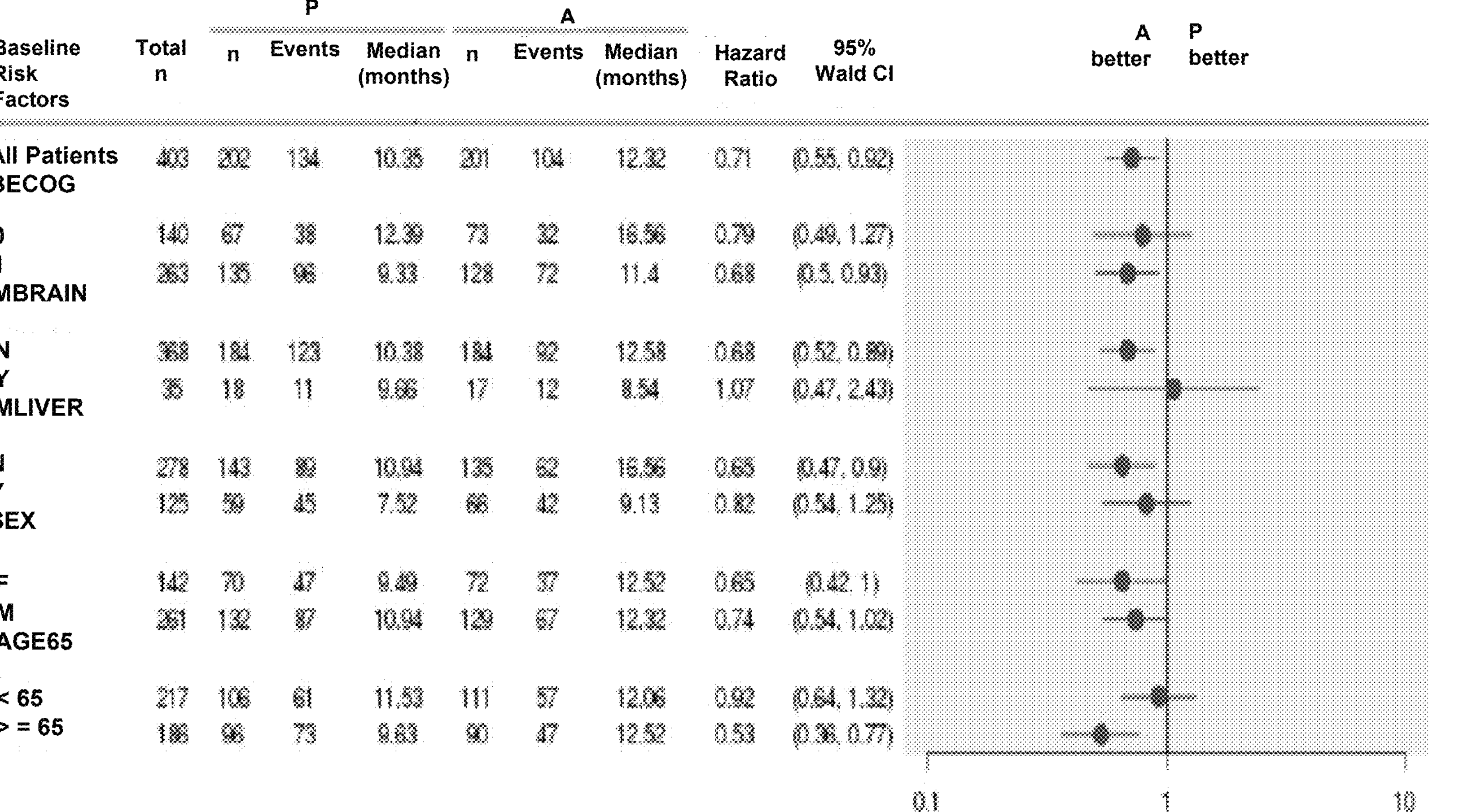
FIG. 5A provides a Forest Plot showing subgroup analyses of OS in patients with various baseline risk factors in Arm A (atezolizumab+carboplatin+etoposide) vs. Arm B (placebo+carboplatin+etoposide). (P=placebo; A=atezolizumab.) Medians were estimated from KM method. Hazard ratios relative to P+CE and the associated confidence intervals were estimated using unstratified Cox regression. Liver metastasis was based on target lesions only.
Figure 5B:
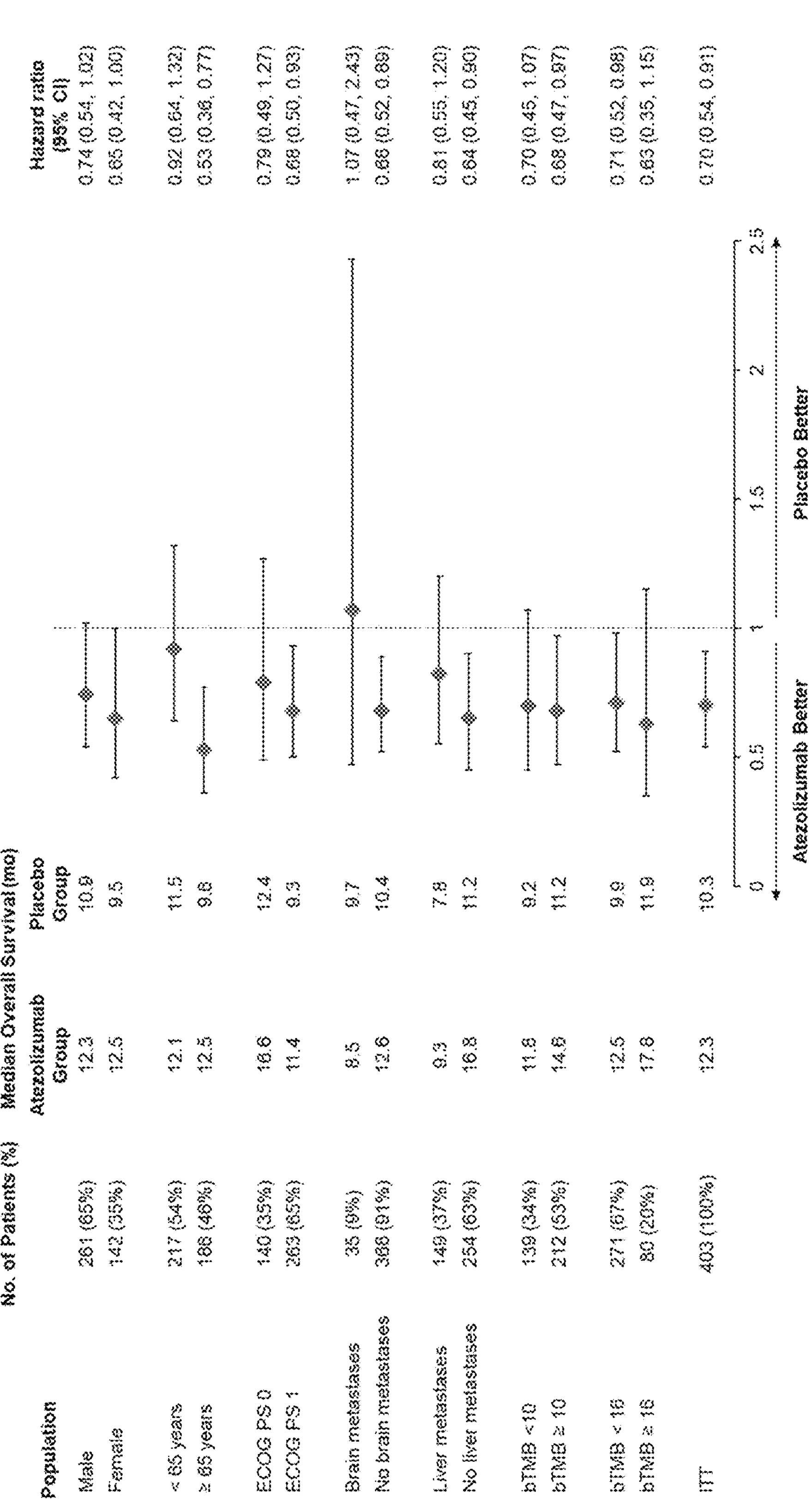
FIG. 5B also provides a Forest Plot showing subgroup analyses of OS in patients with various baseline risk factors in Arm A (atezolizumab+carboplatin+etoposide) vs. Arm B (placebo+carboplatin+etoposide).
Figure 6A:
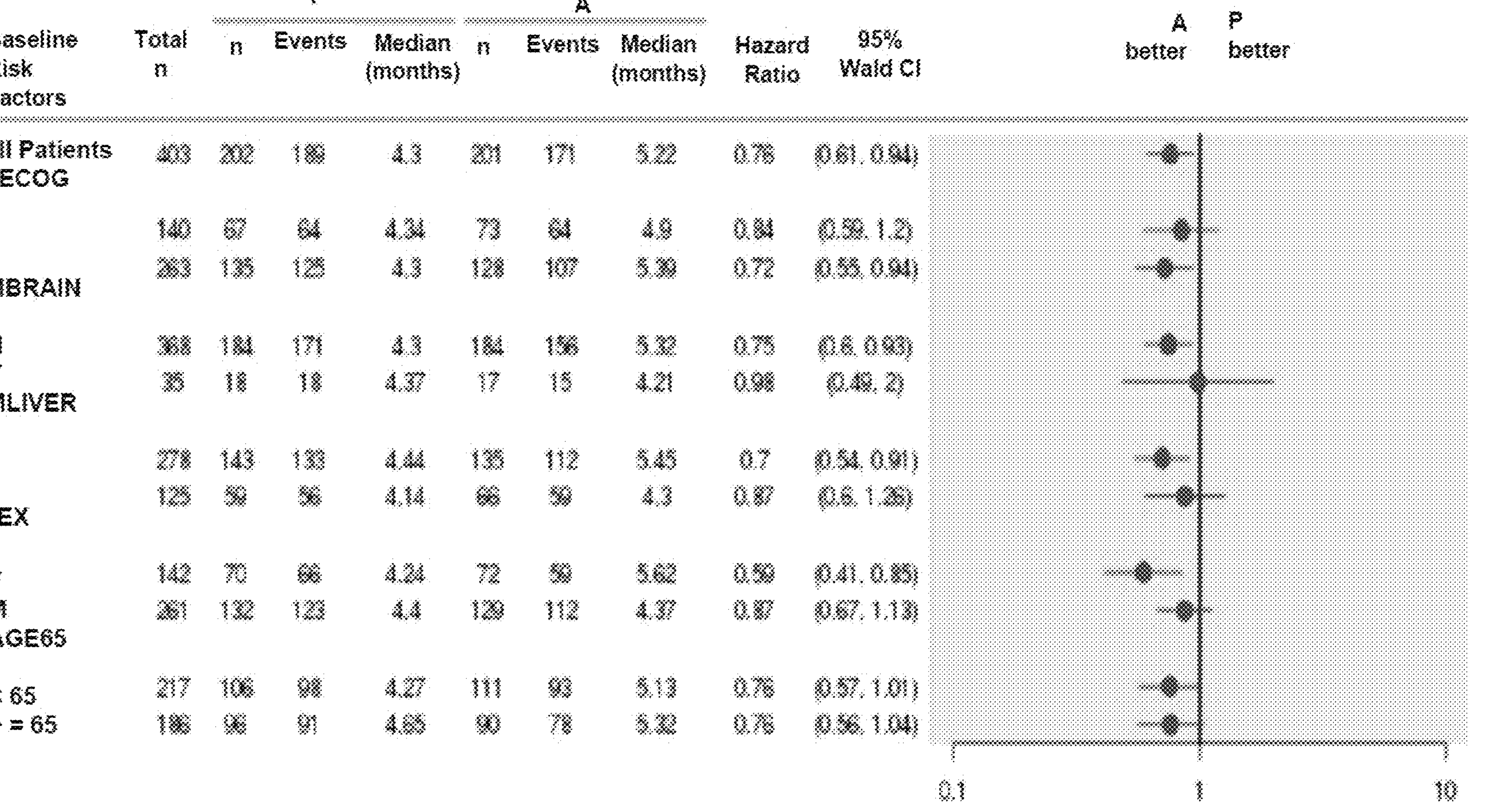
FIG. 6A provides a Forest Plot showing subgroup analyses of PFS in patients with various baseline risk factors in Arm A (atezolizumab+carboplatin+etoposide) vs. Arm B (placebo+carboplatin+etoposide). (P=placebo; A=atezolizumab.) Medians were estimated from KM method. Hazard ratios relative to P+CE and the associated confidence intervals were estimated using unstratified Cox regression. Liver metastasis was based on target lesions only.
Figure 6B:
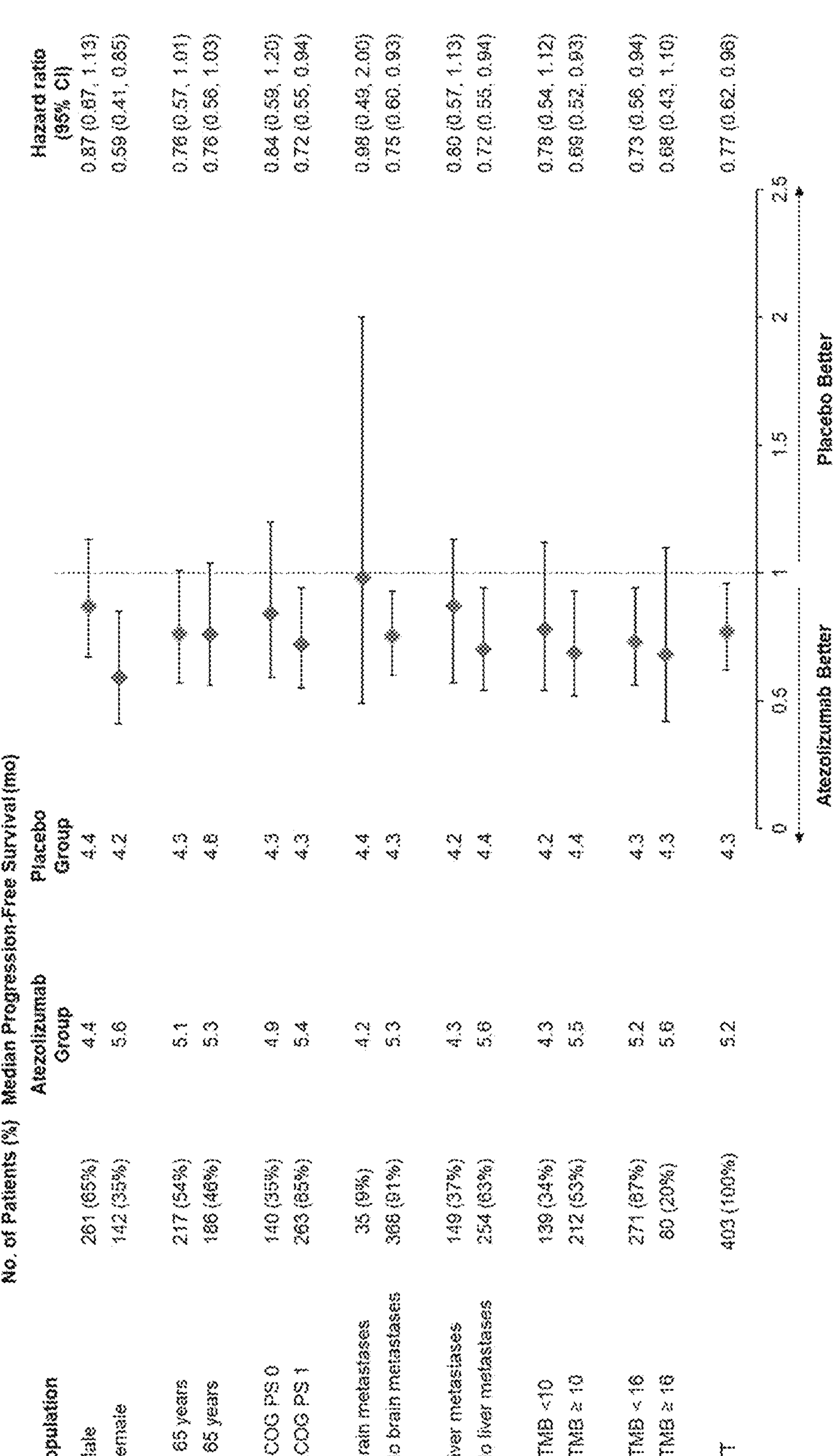
FIG. 6B also provides a Forest Plot showing subgroup analyses of PFS in patients with various baseline risk factors in Arm A (atezolizumab+carboplatin+etoposide) vs. Arm B (placebo+carboplatin+etoposide).
Figure 7A:
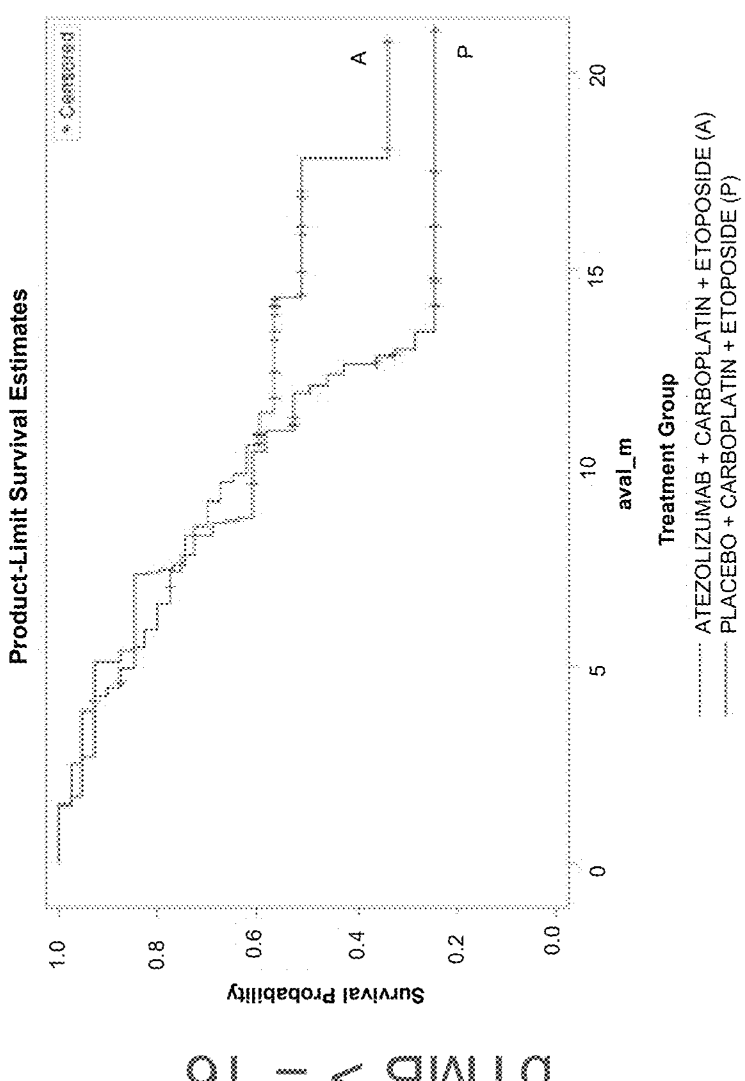
FIG. 7A provides a Kaplan Meier plot of overall survival of patients with a bTMB≥16 in Arm A (atezolizumab+carboplatin+etoposide) vs. Arm B (placebo+carboplatin+etoposide).
Figure 7B:
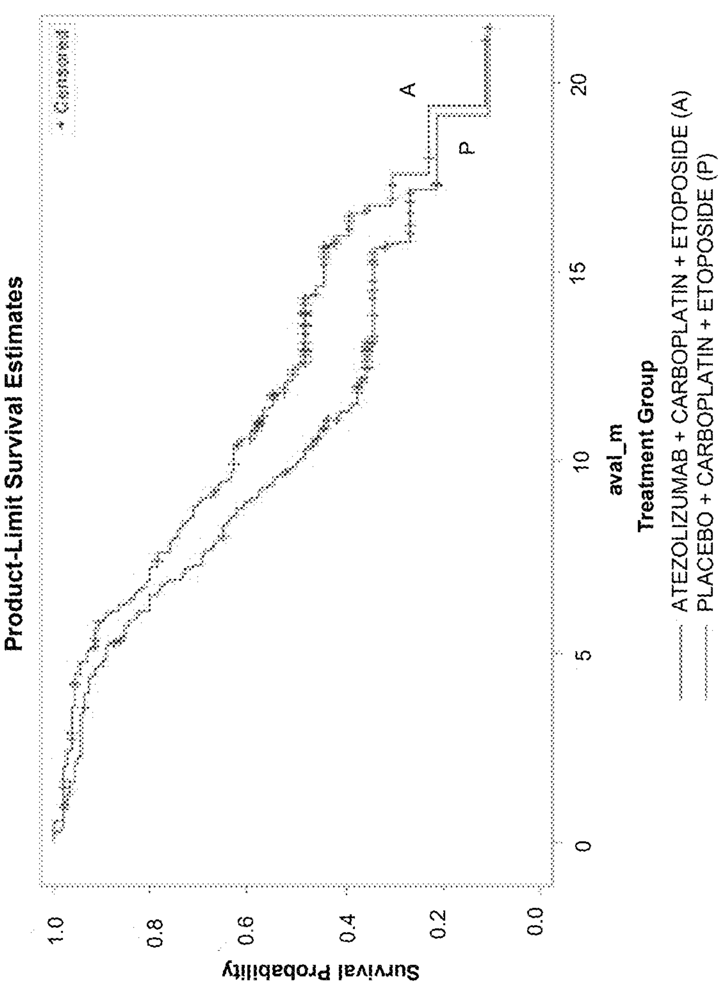
FIG. 7B provides a Kaplan Meier plot of overall survival of patients with a bTMB≤16 in Arm A (atezolizumab+carboplatin+etoposide) vs. Arm B (placebo+carboplatin+etoposide).
Figure 8A:
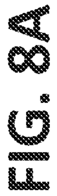
FIG. 8A provides a Kaplan Meier plot of overall survival of patients with a bTMB≥10 in Arm A (atezolizumab+carboplatin+etoposide) vs. Arm B (placebo+carboplatin+etoposide).
Figure 8A:
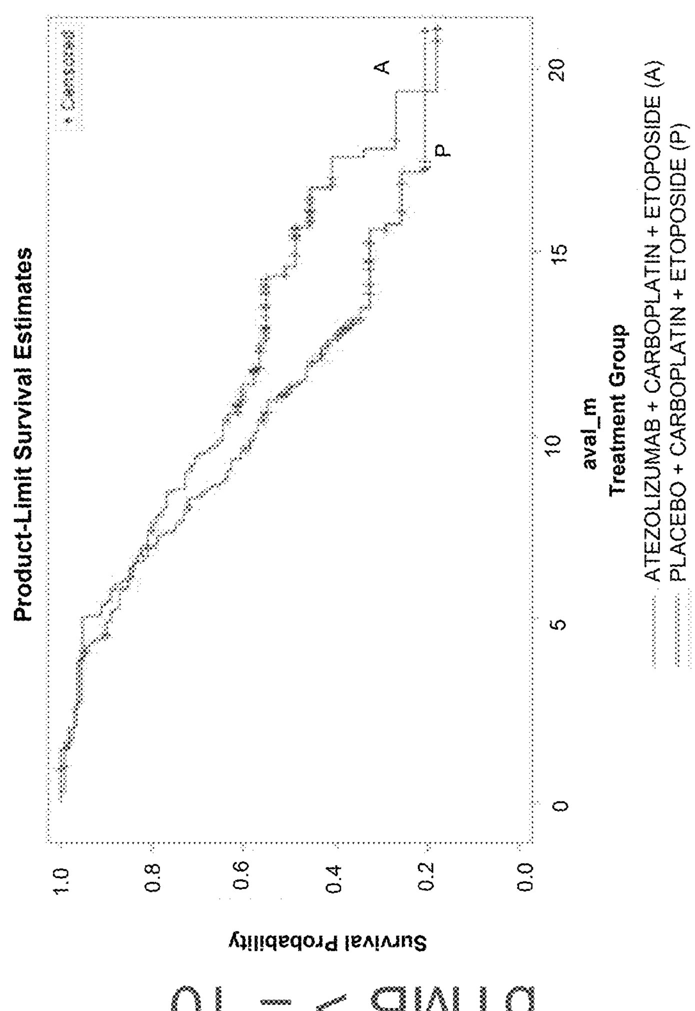
Figure 9A:
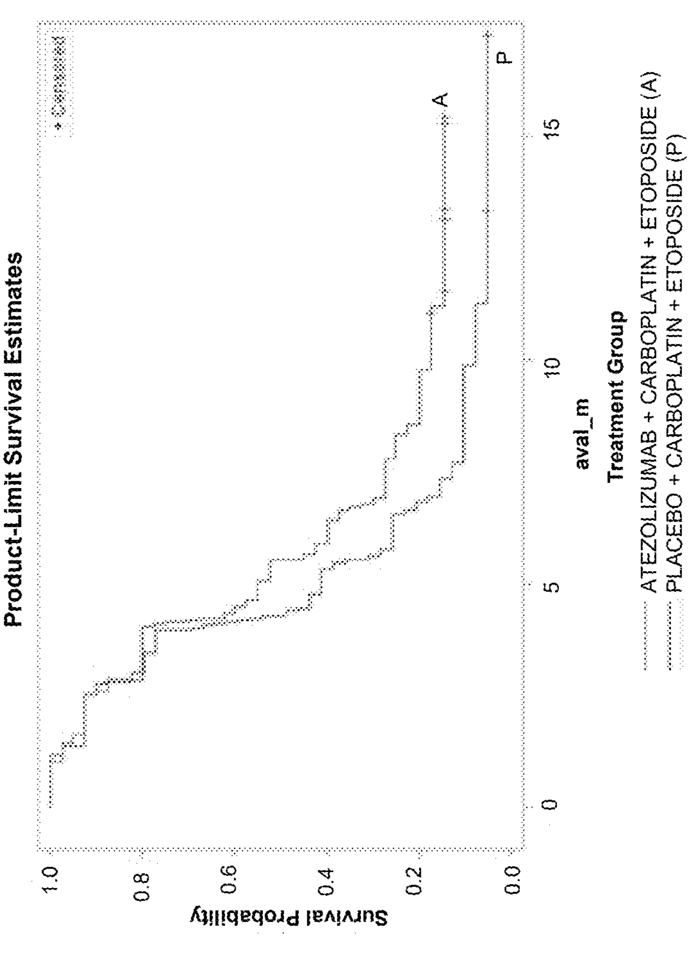
FIG. 9A provides a Kaplan Meier plot of progression-free survival of patients with a bTMB ≥16 in Arm A (atezolizumab+carboplatin+etoposide) vs. Arm B (placebo+carboplatin +etoposide).
Figure 9B:
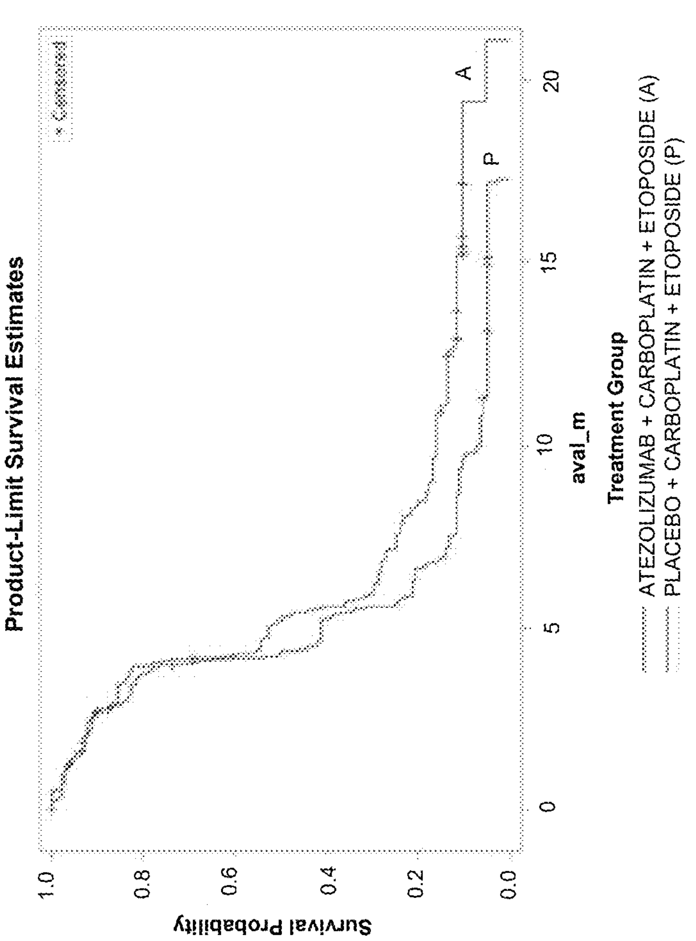
FIG. 9B provides a Kaplan Meier plot of progression-free survival of patients with a bTMB<16 in Arm A (atezolizumab+carboplatin+etoposide) vs. Arm B (placebo+carboplatin +etoposide).
Figure 10A:
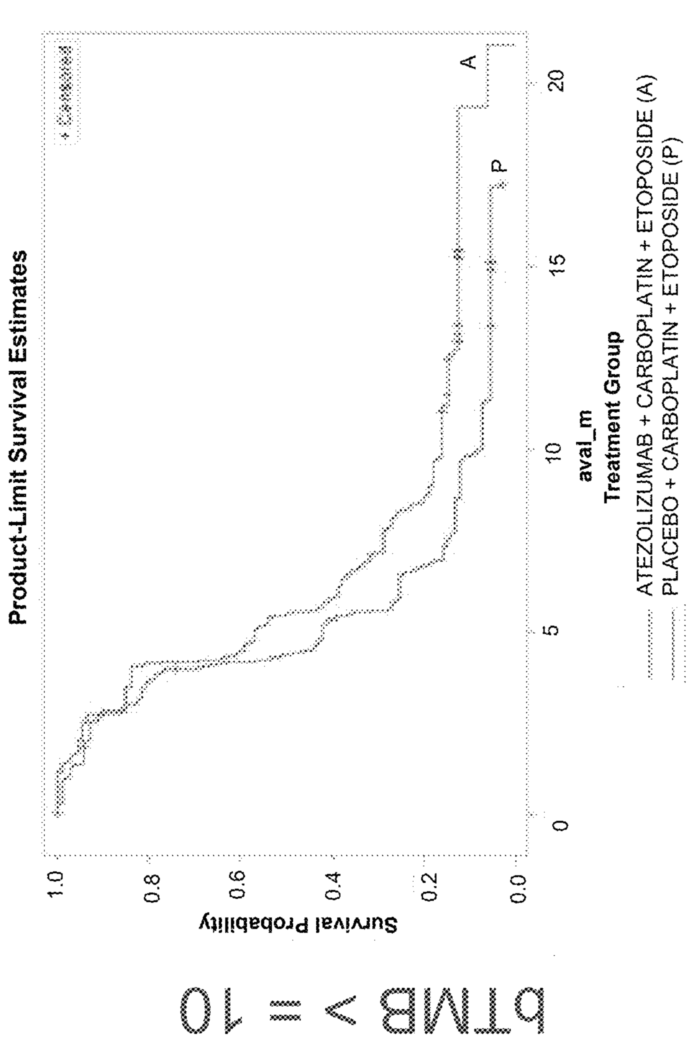
FIG. 10A provides a Kaplan Meier plot of progression-free survival of patients with a bTMB ≥10 in Arm A (atezolizumab+carboplatin+etoposide) vs. Arm B (placebo +carboplatin+etoposide).
Figure 10B:
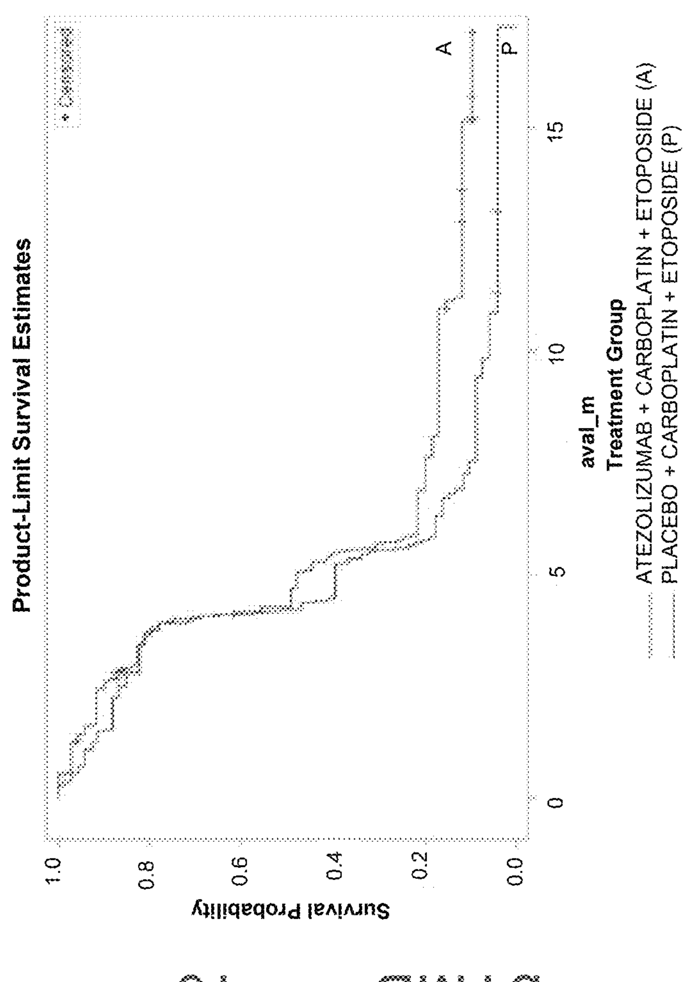
FIG. 10B provides a Kaplan Meier plot of progression-free survival of patients with a bTMB<10 in Arm A (atezolizumab+carboplatin+etoposide) vs. Arm B (placebo+carboplatin +etoposide).

The OS benefit and PFS benefit were observed across all subgroups analyzed. See FIGS. 5 and 6, respectively. The OS benefit was observed regardless of blood tumor mutational burden (bTMB). See FIG. 7A, which shows a Kaplan Meier plot of the OS of patients in each treatment arm with a bTMB ≥16, vs. FIG. 7B, which shows a Kaplan Meier plot of the OS of patients in each treatment arm with a bTMB <16. See also FIG. 8A, which shows a Kaplan Meier plot of the OS of patients in each treatment arm with a bTMB ≥10, vs. FIG. 8B, which shows a Kaplan Meier plot of the OS of patients in each treatment arm with a bTMB <10. Similarly, the PFS benefit was observed regardless of blood tumor mutational burden (bTMB). See FIG. 9A, which shows a Kaplan Meier plot of the PFS of patients in each treatment arm with a bTMB ≥16, vs. FIG. 9B, which shows a Kaplan Meier plot of the PFS of patients in each treatment arm with a bTMB <16. See also FIG. 10A, which shows a Kaplan Meier plot of the PFS of patients in each treatment arm with a bTMB ≥10, vs. FIG. 10B, which shows a Kaplan Meier plot of the PFS of patients in each treatment arm with a bTMB <10.

The safety profile of patients receiving atezolizumab+carboplatin+etoposide was consistent with the known risks of the individual treatment components. No new safety signals were identified. Chemotherapy exposure was similar in both treatment arms, suggesting that the administration of atezolizumab did not compromise the delivery of carboplatin+etoposide in the atezolizumab+carboplatin+etoposide treatment regimen. Toxicities associated with myelosuppression (such as neutropenia and thrombocytopenia) were consistent between both treatment arms and in line with rates associated with chemotherapy.

This study demonstrated that initial (first-line) treatment with the combination of atezolizumab plus chemotherapy (carboplatin and etoposide) helped people with extensive-stage small cell lung cancer (ES-SCLC) live significantly longer compared to chemotherapy alone. The atezolizumab plus chemotherapy (carboplatin and etoposide) combination also reduced the risk of disease worsening or death (PFS) compared to chemotherapy alone. These are the first positive survival results for concurrent treatment with an immunotherapy-based combination in the initial treatment of extensive-stage small cell lung cancer, a particularly difficult-to-treat type of disease. Moreover, this is the first study in over two decades to show a clinically and statistically significant improvement in overall survival over chemotherapy alone in the initial treatment of ES-SCLC. The 1-year survival rate was 13% higher in the atezolizumab group, suggesting the potential for long-term survival benefit in this lethal disease.

Example 2: Patient-Reported Outcomes (PROs) from Example 1

Patients who participated in the study described in Example 1 completed the European Organisation for Research and Treatment of Cancer Quality of Life Questionnaire C30 (EORTC QLQ-C30) and Quality of Life Questionnaire LC13 (QLQ-LC13) at baseline and every three weeks thereafter. Analyses included change from baseline, cumulative distribution function curves of change to week 12 and time to deterioration (TTD). Clinical meaningfulness was based on a ≥10-point change from baseline (score range 0-100).

Completion rates were ≥85% at baseline and ≥70% up to week 75 in both arms of the study. Baseline patient reported outcome scores were comparable between arms. Patients in both arms reported early, notable symptom improvements with a numeric trend of greater improvement with Atezo+CE as compared to Placebo+CE. See Table 11. By week 12, higher proportions of patients receiving Atezo+CE reported relief from their lung cancer (LC)-related symptoms as compared to patients receiving Placebo+CE (see Table 11). No apparent differences in TTD of cough or chest pain were observed, but a numeric delay in TTD of dyspnea favored patients receiving Atezo+CE (HR 0.75 [95% CI 0.55-1.02]). Patients in the Atezo+CE arm reported improved physical/role function and health-related quality of life (HRQoL; ≥10-point increases) that persisted at most visits through week 54. Changes in treatment-related symptoms (e.g., diarrhea, nausea/vomiting) were similar between arms.

First line treatment with Atezo+CE provided OS and PFS benefits in addition to immediate and tangible improvements in patient-reported lung cancer symptoms as compared to treatment with Placebo+CE. Patient reported outcomes indicating sustained function and health-related quality of life improvements with minimal impact from treatment toxicities further support the positive benefit: risk of adding Atezo+CE in first line ES-SCLC.

TABLE 11

| | Range of mean changes up to wk 12 (negative change indicates symptom improvement) | |
|---|---|---|
| | Atezo + CE (n = 124) | Placebo + CE (n = 131) |
| Arm/shoulder pain | −7.0 | −2.5 |
| Chest pain | −7.8 | −4.1 |
| Cough | −14.8 | −15.5 |
| Dyspnoea | −6.5 | −2.3 |

Example 3: Additional Data Regarding the Efficacy of Atezolizumab+Carboplatin+Etoposide Compared with Placebo+Carboplatin+Etoposide in the ITT Population as Measured by Overall Survival (OS)

Additional results from Example 1 regarding the efficacy of atezolizumab+carboplatin+etoposide compared with placebo+carboplatin+etoposide in the ITT population, as measured by overall survival (OS), are described below.

6-, 12-, 18-, and 24-Month Overall Survival

As discussed in Example 1, patients treated with Atezo+CE demonstrated extended overall survival as compared to patients treated with Placebo+CE. See FIG. 2. The 6 month OS of patients receiving Atezo+CE was 85.8% vs. 82.8% in patients receiving Placebo+CE. The 12 month OS of patients receiving Atezo+CE was 51.7% vs. 38.2% in patients receiving Placebo+CE. Patients treated with Atezo+CE also demonstrated extended progression-free survival as compared to patients treated with Placebo+CE. See FIG. 3. The 6 month PFS of patients receiving Atezo+CE was 30.9% vs. 22.4% in patients receiving Placebo+CE. The 12 month PFS of patients receiving Atezo+CE was 12.6% vs. 5.4% in patients receiving Placebo+CE. The one-year overall survival rate of patients treated with Atezo+CE was 51.7%, whereas the one-year overall survival rate of patients receiving Placebo+CE was 38.2%.

In a further analysis performed 22.9 months after randomization, the median OS treated with Atezo+CE was about 23.3 months, and the median OS or patients treated with Placebo+CE was 10.3 months (stratified HR (95% CI)=0.755 (0.601, 0.949); stratified Log-rank p-Value-0.0154). The 6-month, 12-month, 18-month, and 24-month overall survival rates of patents treated with Atezo+CE vs. patients treated with Placebo+CE at the 22.9 month follow-up are provided in Table 12 below:

TABLE 12

| Updated Overall Survival Analyses | | |
|---|---|---|
| | PBO + CE (n = 202) | Atezo + CE (n = 201) |
| 6-month | 82.8% (n = 160) | 85.8% (n = 159) |
| 12-month | 39.0% (n = 74) | 51.9% (n = 93) |
| 18-month | 21.0%) (= 39) | 34.0% (n = 61) |
| 24-month | 16.8% (n = 8) | 22.0% (n = 21) |

The 6-month OS of patients receiving Atezo+CE was 85.8% vs. 82.8% in patients receiving Placebo+CE, as previously described in Example 1. The 12-month OS of patients receiving Atezo+CE was 51.9% vs. 39% in patients receiving Placebo+CE, i.e., very similar to the results described in Example 1. The 18-month OS of patients receiving Atezo+CE was 34% vs. 21% in patients receiving Placebo+CE. The 24-month OS of patients receiving Atezo +CE was 22% vs. 16.8% in patients receiving Placebo+CE.

Subgroup Analyses

Figure 11B:
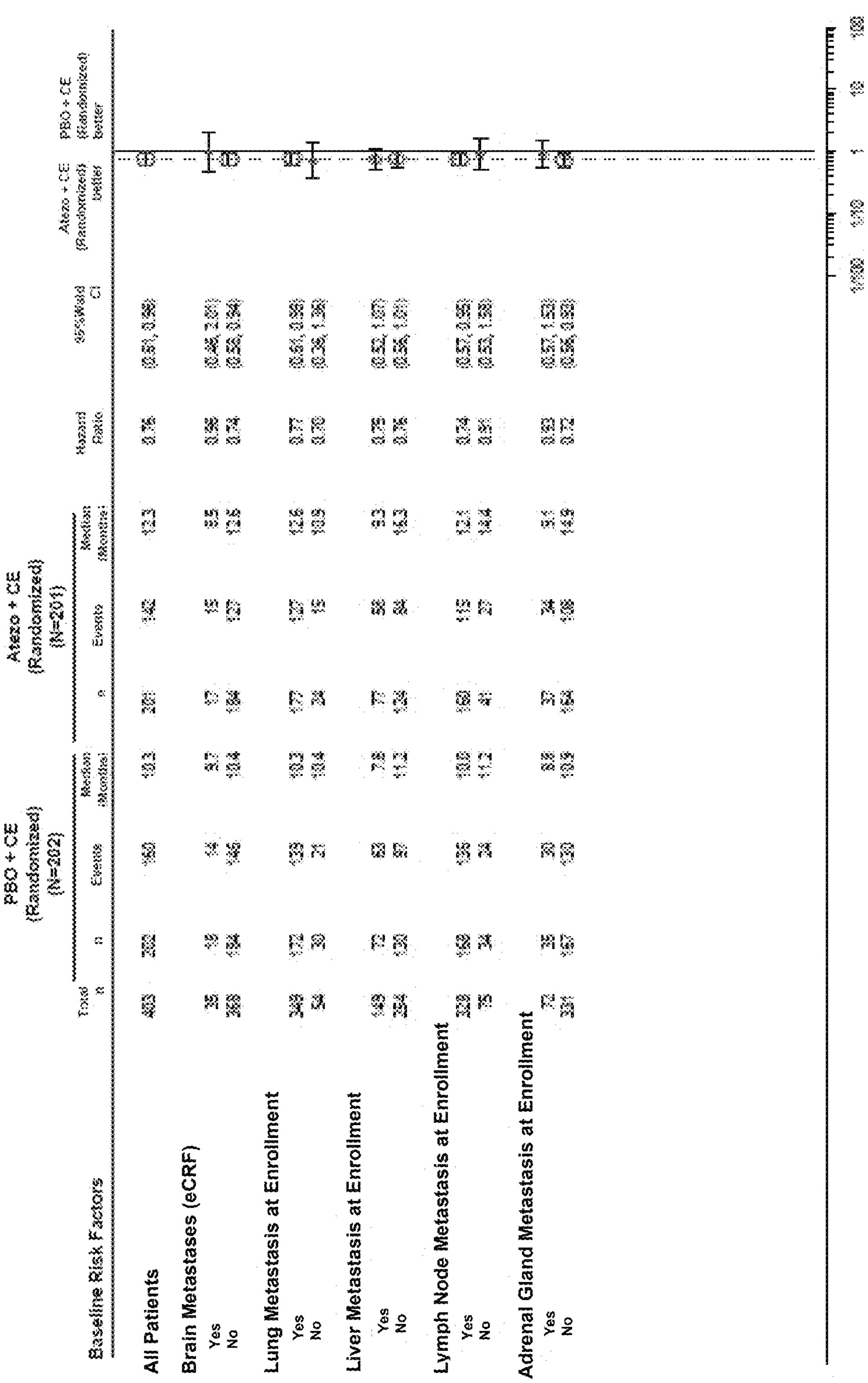
FIG. 11B provides another Forest Plot showing subgroup analyses of OS in patients with various baseline risk factors in Arm A Arm A (atezolizumab+carboplatin+etoposide) vs. Arm B (placebo+carboplatin+etoposide).
Figure 11C:
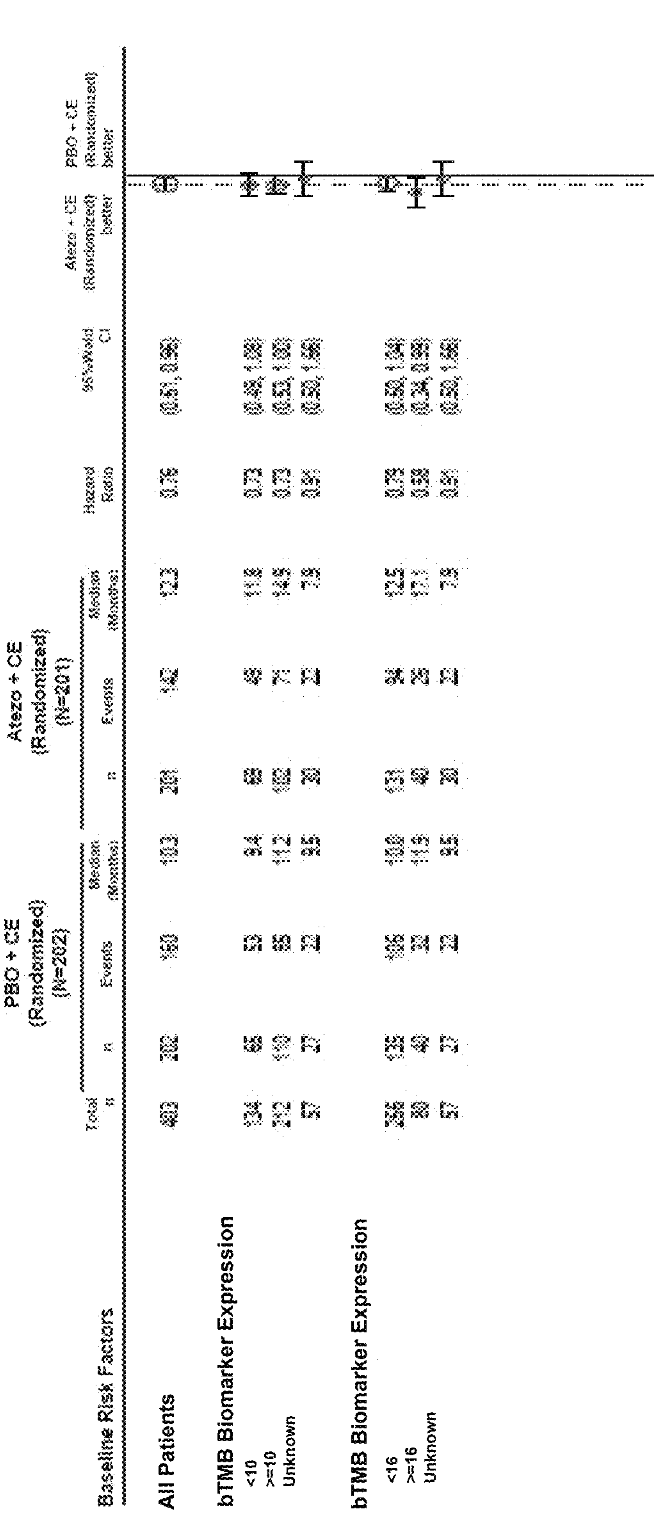
FIG. 11C provides another Forest Plot showing subgroup analyses of OS in patients with various baseline risk factors in Arm A Arm A (atezolizumab+carboplatin+etoposide) vs. Arm B (placebo+carboplatin+etoposide).

Additional updated subgroup analysis data are provided in FIGS. 11A-11C. The OS benefit observed in Example 1 was confirmed in all subgroups analyzed, including, e.g., patients <65 years of age, between 65-74 years of age, between 75-84 years of age, and ≥85 years of age; in both male and female patients; in Native American, Alaskan, Asian, Black, African American, and White patients; in patient patients who had never used tobacco, who were current users of tobacco, and who were previous users of tobacco; in patients with or without metastases in the brain (at enrollment), in the lung (at enrollment), in the liver (at enrollment), in the lymph node (at enrollment), and/or in the adrenal gland (at enrollment); and in all patients regardless of bTMB.

Biomarker Sub-Group Analyses

Patients with ES-SCLC whose disease was unselected for PD-L1 expression were enrolled in the trial described in Example 1. As described in Example 1, where possible, pre-treatment tumor tissue samples were obtained from patients enrolled in the trial for analysis in order to assess the relationship between tumor biomarkers (e.g., PD-L1) and response to treatment. PD-L1 prevalence amongst biomarker-evaluable patients is shown in Table 13.

TABLE 13

| PD-L1 Prevalence in Biomarker-Evaluable Patients | | | |
|---|---|---|---|
| | PBO + CE (n = 202) | Atezo + CE (n = 201) | Total (n = 403) |
| BEP1 (Section age <=1 Yr) | 73 (36%) | 64 (32%) | 137 (34%) |
| TC>=50% or IC>=50% | 0 | 0 | 0 |
| TC>=25% or IC>=25% | 0 | 1 (1.6%) | 1 (0.7%) |
| TC>=5% or IC>=5% | 14 (19.2%) | 15 (23.4%) | 29 (21.2%) |
| TC>=1% or IC>=1% | 36 (49.3%) | 36 (56.3%) | 72 (52.6%) |
| TC<1% and IC<1% | 37 (50.7%) | 28 (43.8%) | 65 (47.4%) |
| BEP2 (Any section age) | 93 (46%) | 75 (37%) | 168 (42%) |
| TC>=50% or IC>=50% | 0 | 0 | 0 |
| TC>=25% or IC>=25% | 0 | 1 (1.3%) | 1 (0.6%) |
| TC>=5% or IC>=5% | 22 (23.7%) | 17 (22.7%) | 39 (23.2%) |
| TC>=1% or IC>=1% | 51 (54.8%) | 42 (56.0%) | 93 (55.4%) |
| TC<1% and IC<1% | 42 (45.2%) | 33 (44.0%) | 75 (44.6%) |

TC = PD-L1 expression on tumor cells
IC = PD-L1 expression on tumor-infiltrating immune cells.

BEP1 refers to the biomarker evaluable patients in the trial with a valid PD-L1 immunohistochemistry (IHC) result from a tumor tissue slide sectioned ≤1 year prior to IHC staining. BEP2 refers to the biomarker evaluable patients in the trial with a valid PD-L1 immunohistochemistry (IHC) result from a tumor tissue slide, regardless of slide age at IHC staining. The percentages for the PD-L1 prevalence at various cutoffs are based on the BEP1/2. The demographic and baseline characteristics of BEP1 and BEP2 were generally balanced between the treatment arms. See Tables 14A and 14B.

TABLE 14A

| Demographics and Baseline Characteristics of BEP1 | | | |
|---|---|---|---|
| Demographics/Baseline | | PBO + CE (n = 73) | Atezo + CE (n = 64) |
| Age (yrs) | <65 | 43 (58.9%) | 41 (61.4%) |
| Sex (eCRF) | Male | 46 (63.0%) | 39 (60.9%) |
| Race | White | 71 (97.3%) | 64 (100.0%) |
| | Asian | NA | NA |
| Tobacco Use History | Never | 1 (1.4%) | 5 (7.8%) |
| Brain mets (eCRF) | Yes | 4 (5.5%) | 3 (4.7%) |
| ECOG score (eCRF) | 0 | 24 (32.9%) | 21 (32.8%) |
| bTMB>=16 | Yes | 13 (19.1%) | 15 (25.9%) |
| bTMB>=10 | Yes | 38 (55.9%) | 36 (62.1%) |
| SLD at Baseline | Median | 123 | 125.5 |
| | Min-Max | (26.0-353.0) | (12.0-325.0) |

TABLE 14B

| Demographics and Baseline Characteristics of BEP2 | | | |
|---|---|---|---|
| Demographics/Baseline | | PBO + CE (n = 93) | Atezo + CE (n = 75) |
| Age (yrs) | <65 | 53 (57.0%) | 46 (61.3%) |
| Sex (eCRF) | Male | 60 (64.5%) | 44 (58.7%) |
| Race | White | 81 (87.1%) | 73 (97.3%) |
| | Asian | 10 (10.8%) | 2 (2.7%) |
| Tobacco Use History | Never | 1 (1.1%) | 6 (8.0%) |
| Brain mets (eCRF) | Yes | 5 (5.4%) | 5 (6.7%) |
| ECOG score (eCRF) | 0 | 32 (34.4%) | 23 (30.7%) |
| bTMB>=16 | Yes | 20 (23.3%) | 20 (29.4%) |
| bTMB>=10 | Yes | 52 (60.5%) | 44 (64.7%) |
| SLD at Baseline | Median | 116 | 122 |
| | Min-Max | (26.0-353.0) | (12.0-325.0) |

SLD = sum of the longest diameters of target lesion (tumor)

Figure 12A:
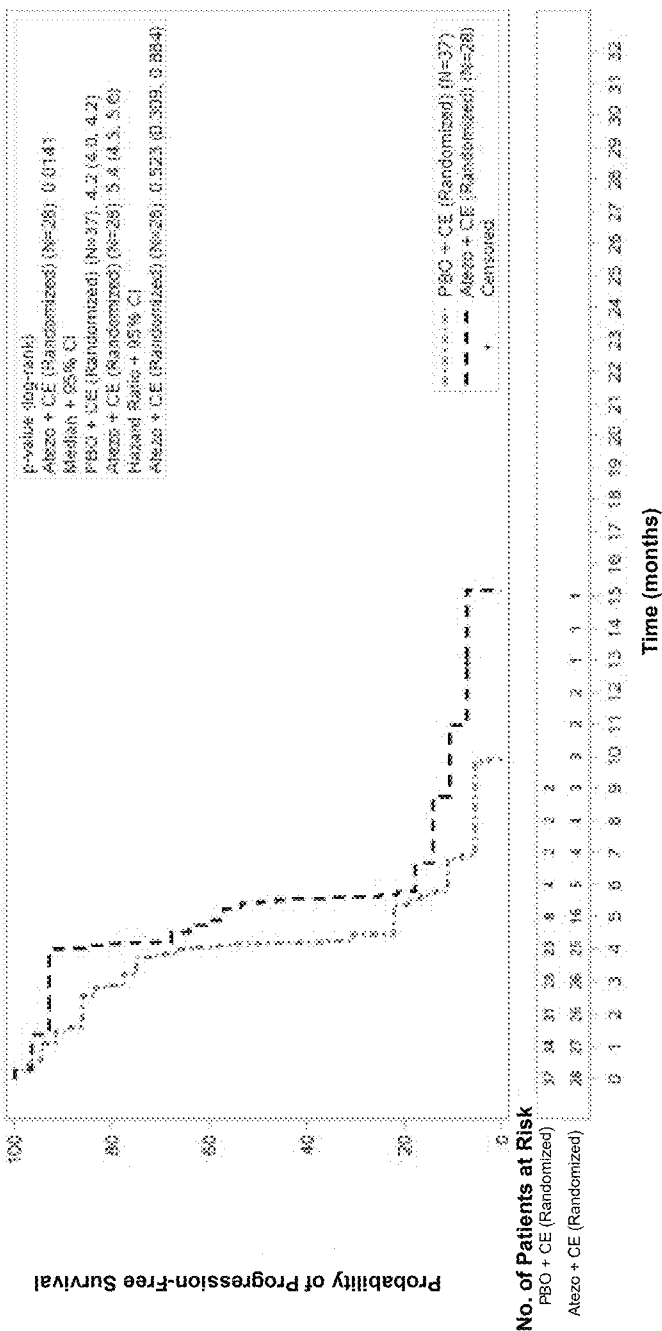
FIG. 12A provides a Kaplan Meier plot of progression-free survival of patients in BEP1 (Biomarker Evaluable Population 1) with PD-L1 expression levels <1% in Arm A (atezolizumab+carboplatin+etoposide) vs. Arm B (placebo+carboplatin+etoposide).
Figure 12B:
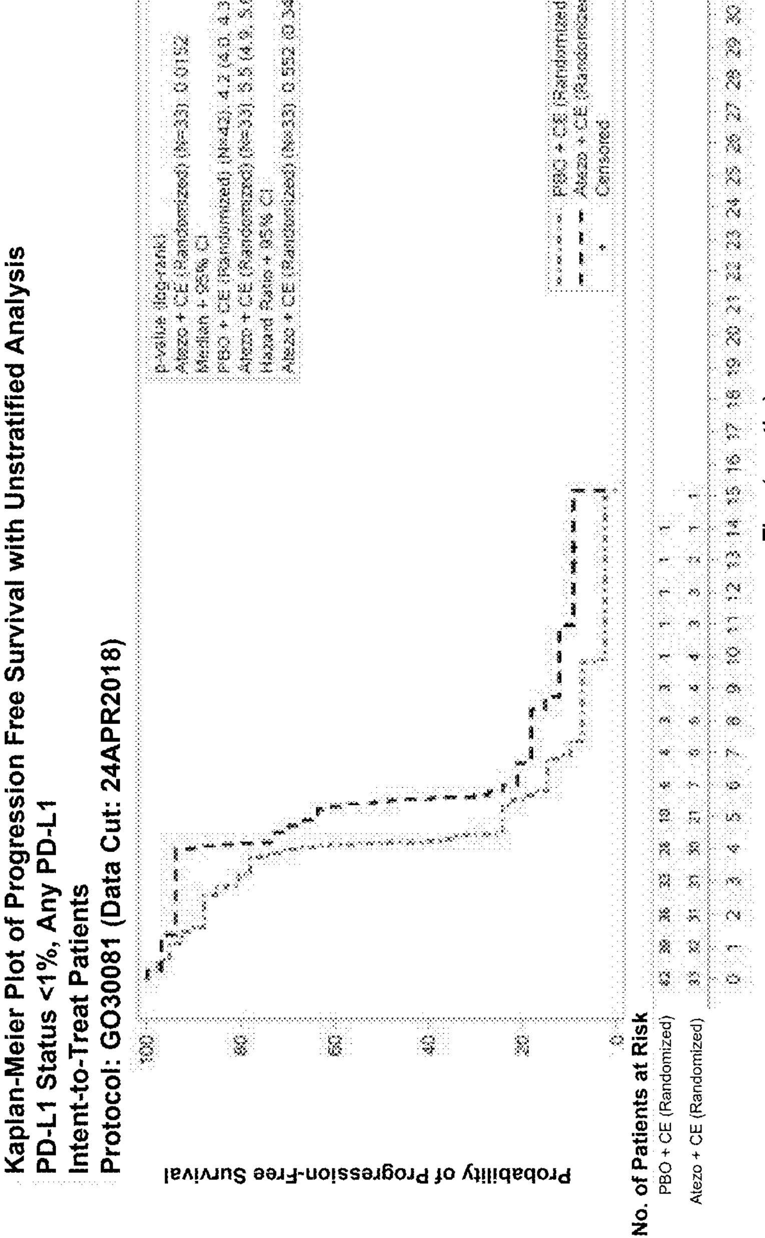
FIG. 12B provides a Kaplan Meier plot of progression-free survival of patients in BEP2 (Biomarker Evaluable Population 2) with PD-L1 expression levels <1% in Arm A (atezolizumab+carboplatin+etoposide) vs. Arm B (placebo+carboplatin+etoposide).

All patients in BEP1 and BEP2 treated with Atezo+CE demonstrated a PFS benefit compared to the patients in BEP1 and BEP2 who were treated with Placebo+CE. As shown in FIGS. 12A and 12B, the PFS benefit was also observed in the patients in BEP1 and BEP who treated with Atezo+CE as compared to the patients receiving Placebo+CE. Moreover, among the patients in BEP1 and BEP2 who had PD-L1 expression levels <1%, the overall response rate (ORR) in patients receiving Atezo+CE was higher than the ORR in patients receiving Placebo +CE. See Table 15.

TABLE 15

| Overall Response Rate in Patients with PD-LI Expression <1% | | |
|---|---|---|
| | Placebo + CE (n = 73) | Atezo + CE (n = 64) |
| BEP1 | | |
| Confirmed ORR TC < 1% and IC < 1% | 62.2% | 75.0% |
| Confirmed ORR TC < 1% and IC < 1% | 70.3% | 82.1% |

TABLE 15-continued

| Overall Response Rate in Patients with PD-LI Expression <1% | | |
|---|---|---|
| | Placebo + CE (n = 73) | Atezo + CE (n = 64) |
| BEP2 | | |
| Confirmed ORR TC < 1% and IC < 1% | 66.7% | 78.8% |
| Confirmed ORR TC < 1% and IC < 1% | 73.8% | 84.8% |

Figure 13A:
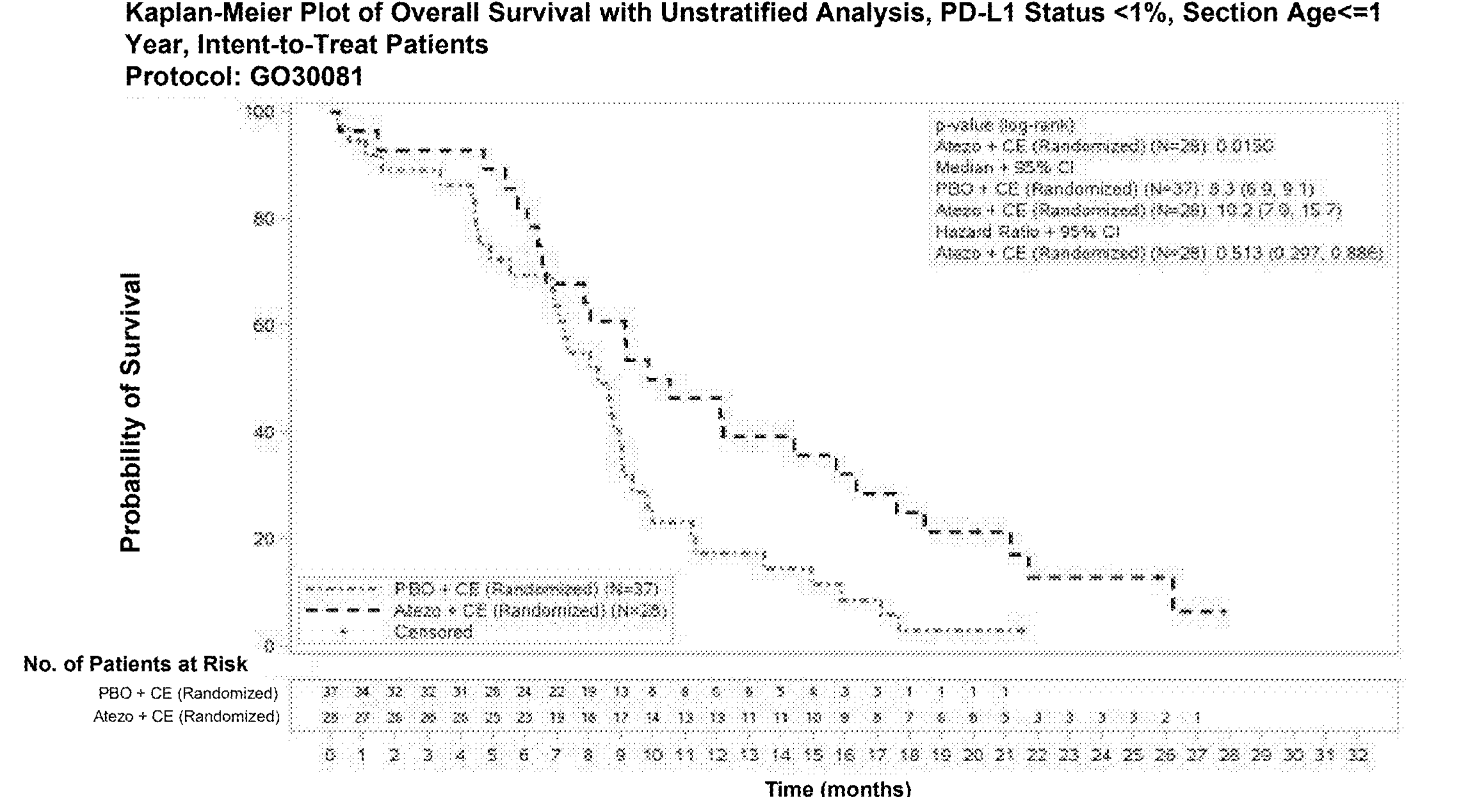
FIG. 13A provides a Kaplan Meier plot of overall survival of patients in BEP1 (Biomarker Evaluable Population 1) with PD-L1 expression levels <1% in Arm A (atezolizumab+carboplatin+etoposide) vs. Arm B (placebo+carboplatin+etoposide).
Figure 13B:
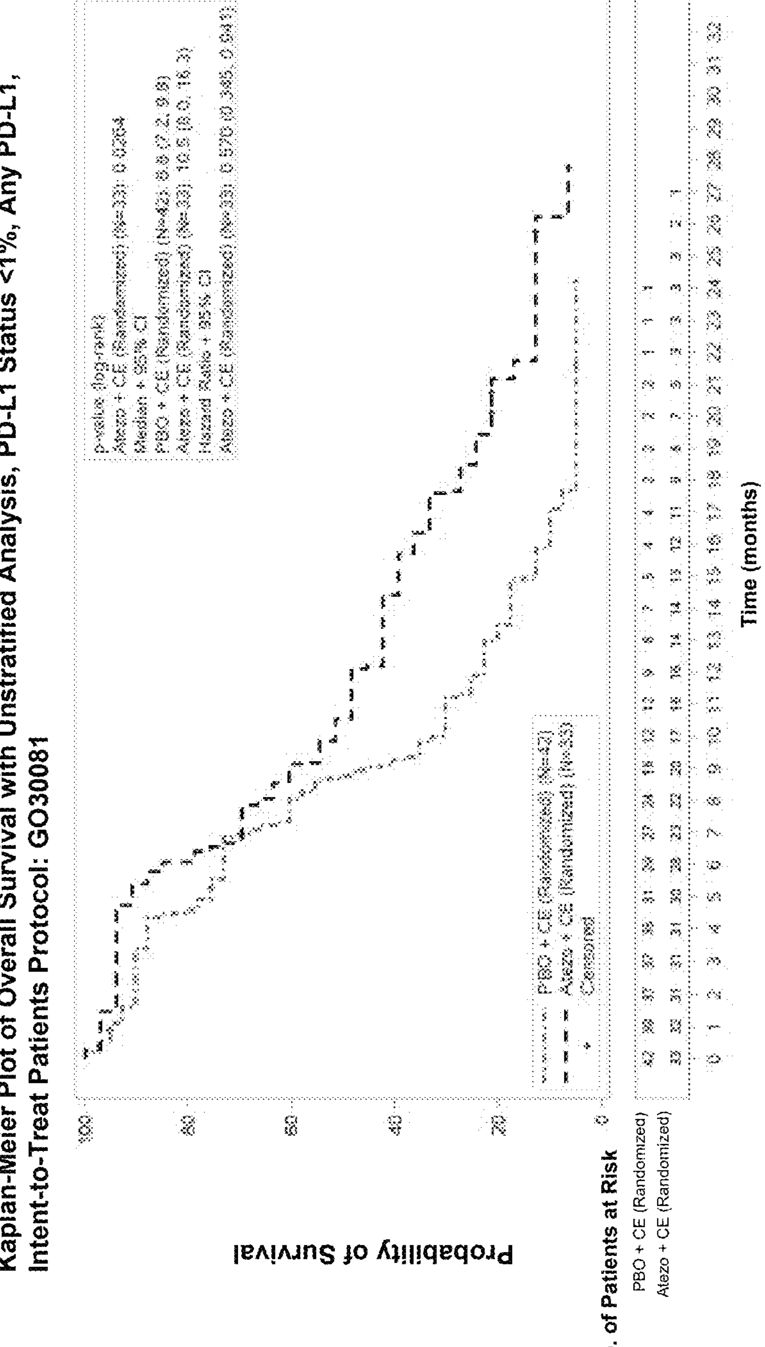
FIG. 13B provides a Kaplan Meier plot of overall survival of patients in BEP2 (Biomarker Evaluable Population 2) with PD-L1 expression levels <1% in Arm A (atezolizumab+carboplatin+etoposide) vs. Arm B (placebo+carboplatin+etoposide).

All patients in BEP1 and BEP2 treated with Atezo+CE demonstrated an OS benefit compared to the patients in BEP1 and BEP2 who were treated with Placebo+CE. As shown in FIGS. 13A and 13B, the PFS benefit was also observed in the patients in BEP1 and BEP who treated with Atezo+CE as compared to the patients receiving Placebo+CE.

Thus, the PD-L1 negative subgroup (i.e., patients having <1% PD-L1 expression on tumor cells or on tumor-infiltrating immune cells) was found to derive clinical benefit from treatment with Atezo+CE as compared with patients treated with Placebo+CE. Such result indicates and all-comer treatment benefit.

Although the present disclosure has been described in some detail by way of illustration and example for purposes of clarity of understanding, the descriptions and examples should not be construed as limiting the scope of the present disclosure. The disclosures of all patent and scientific literature cited herein are expressly incorporated in their entirety by reference.

The invention claimed is:

1. A method for the treatment of a patient having extensive-stage small cell lung cancer (ES-SCLC), comprising administering to the patient a treatment comprising an effective amount of atezolizumab, an effective amount of carboplatin, and an effective amount of etoposide, wherein the atezolizumab, the carboplatin, and the etoposide are each administered in four 21-day dosing cycles (Cycles 1-4), wherein the atezolizumab is administered at a dose of 1200 mg on day 1 of each of Cycles 1-4, the carboplatin is administered at a dose sufficient to achieve AUC=5 mg/ml/min on day 1 of each of Cycles 1-4, and the etoposide is administered at a dose of 100 $mg/m^2$ on each of days 1, 2, and 3 of each of Cycles 1-4, and wherein on day 1 of each of Cycles 1-4, the atezolizumab is administered prior to administration of the carboplatin and the etoposide.

2. The method of claim 1, wherein the atezolizumab, the carboplatin, and the etoposide are each administered intravenously.

3. The method of claim 1, wherein the ES-SCLC has metastasized to the lung or to the lymph nodes.

4. The method of claim 1, wherein the treatment is a first-line treatment.

5. The method of claim 1, wherein the patient is at least 65 years old.

6. The method of claim 1, wherein a blood sample obtained from the patient prior to treatment has been determined to have a blood tumor mutation burden (bTMB) of greater than or equal to 10 and less than 16.

7. The method of claim 1, wherein a tumor sample obtained from the patient prior to treatment has been determined to have an expression level of PD-L1 on tumor cells or tumor-infiltrating immune cells that comprise less than 1% of the tumor sample.

8. The method of claim 1, wherein the atezolizumab is further administered in one or more 21-day dosing cycles following Cycle 4 at a dose of 1200 mg on day 1 of each of the one or more 21-day dosing cycles following Cycle 4.

9. The method of claim 1, wherein on day 1 of each of Cycles 1-4, atezolizumab is administered prior to administration of carboplatin, and carboplatin is administered prior to administration of etoposide.

10. A method for the treatment of a patient having ES-SCLC, comprising administering to the patient a treatment comprising an effective amount of atezolizumab, an effective amount of carboplatin, and an effective amount of etoposide, wherein the atezolizumab, the carboplatin, and the etoposide are each administered in four 21-day dosing cycles (Cycles 1-4), wherein the atezolizumab is administered at a dose of 1200 mg on day 1 of each of Cycles 1-4, the carboplatin is administered at a dose sufficient to achieve AUC=5 mg/ml/min on day 1 of each of Cycles 1-4, and the etoposide is administered at a dose of 100 $mg/m^2$ on each of days 1, 2, and 3 of each of Cycles 1-4, wherein on day 1 of each of Cycles 1-4, the atezolizumab is administered prior to administration of the carboplatin and the etoposide, and administering the treatment to patients having ES-SCLC increases the median overall survival (OS) time of the patients that have been administered the treatment as compared to a reference OS time, wherein the reference OS time is the median OS time of patients having ES-SCLC that have been administered a reference treatment comprising carboplatin and etoposide in the absence of atezolizumab, and wherein the OS time of each patient administered the treatment or the reference treatment is measured as the period of time from the start of the treatment or the reference treatment to death of the patient from any cause.

11. The method of claim 10, wherein the median OS time is increased by about 2 months as compared to the reference OS time.

12. The method of claim 10, wherein the treatment increases the rate of OS of patients having ES-SCLC that have been administered the treatment as compared to a reference rate of OS, wherein the rate of OS at 12 months increases by about 13% as compared to the reference rate of OS, wherein the reference rate of OS is the rate of OS of patients having ES-SCLC that have been administered a reference treatment comprising carboplatin and etoposide in the absence of atezolizumab, and wherein the OS of each patient administered the treatment or the reference treatment is measured as the period of time from the start of the treatment or the reference treatment to death of the patient from any cause.

13. The method of claim 10, wherein the treatment increases the median progression free survival (PFS) time of a population of individuals having ES-SCLC that have been administered an effective amount of atezolizumab, the carboplatin, and the etoposide, as compared to a reference PFS time, wherein the reference PFS time is the median PFS time of a population of individuals having ES-SCLC that have been administered a treatment comprising carboplatin and etoposide in the absence of atezolizumab, and wherein the median PFS time or the reference PFS time is measured as the period of time from the start of treatment to a first occurrence of disease progression or death from any cause.

14. The method of claim 13, wherein the median PFS time is increased by about 1 month as compared to the reference PFS time.

15. The method of claim 10, wherein the treatment increases the rate of PFS of patients having ES-SCLC that have been administered the treatment as compared to a reference rate of PFS, wherein the rate of PFS at 12 months increases by about 7% as compared to the reference rate of PFS, wherein the reference rate of PFS is the rate of PFS of patients having ES-SCLC that have been administered a reference treatment comprising carboplatin and etoposide in the absence of atezolizumab, and wherein the PFS of each patient administered the treatment or the reference treatment is measured as the period of time from the start of the treatment or the reference treatment to a first occurrence of disease progression in the patient or death of the patient from any cause.

16. The method of claim 10, wherein the atezolizumab, the carboplatin, and the etoposide are each administered intravenously.

17. The method of claim 10, wherein the ES-SCLC has metastasized to the lung or to the lymph nodes.

18. The method of claim 10, wherein the treatment is a first-line treatment.

19. The method of claim 10, wherein the patient is at least 65 years old.

20. The method of claim 10, wherein a blood sample obtained from the patient prior to treatment has been determined to have a bTMB of greater than or equal to 10 and less than 16.

21. The method of claim 10, wherein a tumor sample obtained from the patient prior to treatment has been determined to have an expression level of PD-L1 on tumor cells or tumor-infiltrating immune cells that comprise less than 1% of the tumor sample.

22. The method of claim 10, wherein the atezolizumab is further administered in one or more 21-day dosing cycles following Cycle 4 at a dose of 1200 mg on day 1 of each of the one or more 21-day dosing cycles following Cycle 4.

23. The method of claim 10, wherein on day 1 of each of Cycles 1-4, atezolizumab is administered prior to administration of carboplatin, and carboplatin is administered prior to administration of etoposide.

24. A method of extending OS time of patients having ES-SCLC, the method comprising:

(a) administering to the patients an effective amount of atezolizumab, an effective amount of carboplatin, and an effective amount of etoposide, wherein the atezolizumab, the carboplatin, and the etoposide are each administered in four 21-day dosing cycles (Cycles 1-4), wherein the atezolizumab is administered at a dose of 1200 mg on day 1 of each of Cycles 1-4, the carboplatin is administered at a dose sufficient to achieve AUC=5 mg/ml/min on day 1 of each of Cycles 1-4, and the etoposide is administered at a dose of 100 $mg/m^2$ on each of days 1, 2, and 3 of each of Cycles 1-4, wherein on day 1 of each of Cycles 1-4, the atezolizumab is administered prior to administration of the carboplatin and the etoposide, and administering the treatment to patients having ES-SCLC increases the median OS time of the patients that have been administered the treatment as compared to a reference OS time, wherein the reference OS time is the median OS time of patients having ES-SCLC that have been administered a reference treatment comprising carboplatin and etoposide in the absence of atezolizumab, and wherein the OS time of each patient administered the treatment or the reference treatment is measured as the period of time from the start of the treatment or the reference treatment to death of the patient from any cause; and (b) measuring OS time of the patients to confirm it is extended.

25. The method of claim 24, wherein the treatment increases the median PFS time of the patients that have been administered the treatment as compared to a reference PFS time, wherein the reference PFS time is the median PFS time of patients having ES-SCLC that have been administered a reference treatment comprising carboplatin and etoposide in the absence of atezolizumab, and wherein the PFS time of each patient administered the treatment or the reference treatment is measured as the period of time from the start of the treatment or the reference treatment to a first occurrence of disease progression in the patient or death of the patient from any cause.

26. The method of claim 24, wherein the treatment is a first-line treatment.

27. The method of claim 24, wherein on day 1 of each of Cycles 1-4, atezolizumab is administered prior to administration of carboplatin, and carboplatin is administered prior to administration of etoposide.

28. A method for the treatment of a patient having ES-SCLC, comprising administering to the patient a treatment comprising an effective amount of atezolizumab, an effective amount of carboplatin, and an effective amount of etoposide, wherein the atezolizumab, the carboplatin, and the etoposide are each administered in four 21-day dosing cycles (Cycles 1-4), wherein the atezolizumab is administered at a dose of 1200 mg on day 1 of each of Cycles 1-4, the carboplatin is administered at a dose sufficient to achieve AUC=5 mg/ml/min on day 1 of each of Cycles 1-4, and the etoposide is administered at a dose of 100 $mg/m^2$ on each of days 1, 2, and 3 of each of Cycles 1-4, wherein on day 1 of each of Cycles 1-4, the atezolizumab is administered prior to administration of the carboplatin and the etoposide, wherein the atezolizumab is further administered in one or more 21-day dosing cycles following Cycle 4 at a dose of 1200 mg on day 1 of each of the one or more 21-day dosing cycles following Cycle 4, wherein the patients are administered atezolizumab for a duration of at least 12 months in total starting from Cycle 1, and administering the treatment to patients having ES-SCLC increases the median OS time of the patients that have been administered the treatment as compared to a reference OS time, wherein the reference OS time is the median OS time of patients having ES-SCLC that have been administered a reference treatment comprising carboplatin and etoposide in the absence of atezolizumab, and wherein the OS time of each patient administered the treatment or the reference treatment is measured as the period of time from the start of the treatment or the reference treatment to death of the patient from any cause.

29. The method of claim 28, wherein the treatment is a first-line treatment.

30. The method of claim 28, wherein the treatment increases the median PFS time of the patients that have been administered the treatment as compared to a reference PFS time, wherein the reference PFS time is the median PFS time of patients having ES-SCLC that have been administered a reference treatment comprising carboplatin and etoposide in the absence of atezolizumab, and wherein the PFS time of each patient administered the treatment or the reference treatment is measured as the period of time from the start of the treatment or the reference treatment to a first occurrence of disease progression in the patient or death of the patient from any cause.

31. The method of claim 28, wherein on day 1 of each of Cycles 1-4, atezolizumab is administered prior to administration of carboplatin, and carboplatin is administered prior to administration of etoposide.

32. A method for extending OS time of patients having ES-SCLC, comprising administering to the patients a treatment comprising an effective amount of atezolizumab, an effective amount of carboplatin, and an effective amount of etoposide, wherein the atezolizumab, the carboplatin, and the etoposide are each administered in four 21-day dosing cycles (Cycles 1-4), wherein the atezolizumab is administered at a dose of 1200 mg on day 1 of each of Cycles 1-4, the carboplatin is administered at a dose sufficient to achieve AUC=5 mg/ml/min on day 1 of each of Cycles 1-4, and the etoposide is administered at a dose of 100 $mg/m^2$ on each of days 1, 2, and 3 of each of Cycles 1-4, wherein on day 1 of each of Cycles 1-4, the atezolizumab is administered prior to administration of the carboplatin and the etoposide, wherein the atezolizumab is further administered in one or more 21-day dosing cycles following Cycle 4 at a dose of 1200 mg on day 1 of each of the one or more 21-day dosing cycles following Cycle 4, wherein the patients are administered atezolizumab for a duration of at least 12 months in total starting from Cycle 1, and administering the treatment to patients having ES-SCLC increases the median OS time of the patients that have been administered the treatment as compared to a reference OS time, wherein the reference OS time is the median OS time of patients having ES-SCLC that have been administered a reference treatment comprising carboplatin and etoposide in the absence of atezolizumab, and wherein the OS time of each patient administered the treatment or the reference treatment is measured as the period of time from the start of the treatment or the reference treatment to death of the patient from any cause.

33. The method of claim 32, wherein the treatment is a first-line treatment.

34. The method of claim 32, wherein the treatment increases the median PFS time of the patients that have been administered the treatment as compared to a reference PFS time, wherein the reference PFS time is the median PFS time of patients having ES-SCLC that have been administered a reference treatment comprising carboplatin and etoposide in the absence of atezolizumab, and wherein the PFS time of each patient administered the treatment or the reference treatment is measured as the period of time from the start of the treatment or the reference treatment to a first occurrence of disease progression in the patient or death of the patient from any cause.

35. The method of claim 32, wherein on day 1 of each of Cycles 1-4, atezolizumab is administered prior to administration of carboplatin, and carboplatin is administered prior to administration of etoposide.

* * * * *

SEQUENCE LISTING

```
Sequence total quantity: 20
SEQ ID NO: 1            moltype = AA  length = 10
FEATURE                 Location/Qualifiers
REGION                  1..10
                        note = Synthetic Construct
source                  1..10
                        mol_type = protein
                        organism = synthetic construct
SEQUENCE: 1
GFTFSDSWIH                                                      10

SEQ ID NO: 2            moltype = AA  length = 18
FEATURE                 Location/Qualifiers
REGION                  1..18
                        note = Synthetic Construct
source                  1..18
                        mol_type = protein
                        organism = synthetic construct
SEQUENCE: 2
AWISPYGGST YYADSVKG                                             18

SEQ ID NO: 3            moltype = AA  length = 9
FEATURE                 Location/Qualifiers
REGION                  1..9
                        note = Synthetic Construct
source                  1..9
                        mol_type = protein
                        organism = synthetic construct
SEQUENCE: 3
RHWPGGFDY                                                       9

SEQ ID NO: 4            moltype = AA  length = 11
FEATURE                 Location/Qualifiers
REGION                  1..11
                        note = Synthetic Construct
source                  1..11
                        mol_type = protein
                        organism = synthetic construct
SEQUENCE: 4
RASQDVSTAV A                                                    11

SEQ ID NO: 5            moltype = AA  length = 7
FEATURE                 Location/Qualifiers
REGION                  1..7
                        note = Synthetic Construct
source                  1..7
                        mol_type = protein
                        organism = synthetic construct
SEQUENCE: 5
SASFLYS                                                         7

SEQ ID NO: 6            moltype = AA  length = 9
FEATURE                 Location/Qualifiers
REGION                  1..9
                        note = Synthetic Construct
source                  1..9
                        mol_type = protein
```

```
                         organism = synthetic construct
SEQUENCE: 6
QQYLYHPAT                                                          9

SEQ ID NO: 7             moltype = AA  length = 118
FEATURE                  Location/Qualifiers
REGION                   1..118
                         note = Synthetic Construct
source                   1..118
                         mol_type = protein
                         organism = synthetic construct
SEQUENCE: 7
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSS    118

SEQ ID NO: 8             moltype = AA  length = 108
FEATURE                  Location/Qualifiers
REGION                   1..108
                         note = Synthetic Construct
source                   1..108
                         mol_type = protein
                         organism = synthetic construct
SEQUENCE: 8
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKR               108

SEQ ID NO: 9             moltype = AA  length = 447
FEATURE                  Location/Qualifiers
REGION                   1..447
                         note = Synthetic Construct
source                   1..447
                         mol_type = protein
                         organism = synthetic construct
SEQUENCE: 9
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYAST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                     447

SEQ ID NO: 10            moltype = AA  length = 214
FEATURE                  Location/Qualifiers
REGION                   1..214
                         note = Synthetic Construct
source                   1..214
                         mol_type = protein
                         organism = synthetic construct
SEQUENCE: 10
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 11            moltype = AA  length = 440
FEATURE                  Location/Qualifiers
REGION                   1..440
                         note = Synthetic Construct
source                   1..440
                         mol_type = protein
                         organism = synthetic construct
SEQUENCE: 11
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSSASTKGPS  120
VFPLAPCSRS TSESTAALGC LVKDYFPEPV TVSWNSGALT SGVHTFPAVL QSSGLYSLSS  180
VVTVPSSSLG TKTYTCNVDH KPSNTKVDKR VESKYGPPCP PCPAPEFLGG PSVFLFPPKP  240
KDTLMISRTP EVTCVVVDVS QEDPEVQFNW YVDGVEVHNA KTKPREEQFN STYRVVSVLT  300
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
MHEALHNHYT QKSLSLSLGK                                              440

SEQ ID NO: 12            moltype = AA  length = 214
FEATURE                  Location/Qualifiers
REGION                   1..214
                         note = Synthetic Construct
source                   1..214
                         mol_type = protein
```

```
                          organism = synthetic construct
SEQUENCE: 12
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 13             moltype = AA  length = 447
FEATURE                   Location/Qualifiers
REGION                    1..447
                          note = Synthetic Construct
source                    1..447
                          mol_type = protein
                          organism = synthetic construct
SEQUENCE: 13
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                       447

SEQ ID NO: 14             moltype = AA  length = 218
FEATURE                   Location/Qualifiers
REGION                    1..218
                          note = Synthetic Construct
source                    1..218
                          mol_type = protein
                          organism = synthetic construct
SEQUENCE: 14
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                           218

SEQ ID NO: 15             moltype = AA  length = 449
FEATURE                   Location/Qualifiers
REGION                    1..449
                          note = Synthetic Construct
source                    1..449
                          mol_type = protein
                          organism = synthetic construct
SEQUENCE: 15
EVQLLESGGG LVQPGGSLRL SCAASGFTFS SYIMMWVRQA PGKGLEWVSS IYPSGGITFY  60
ADTVKGRFTI SRDNSKNTLY LQMNSLRAED TAVYYCARIK LGTVTTVDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                     449

SEQ ID NO: 16             moltype = AA  length = 216
FEATURE                   Location/Qualifiers
REGION                    1..216
                          note = Synthetic Construct
source                    1..216
                          mol_type = protein
                          organism = synthetic construct
SEQUENCE: 16
QSALTQPASV SGSPGQSITI SCTGTSSDVG GYNYVSWYQQ HPGKAPKLMI YDVSNRPSGV  60
SNRFSGSKSG NTASLTISGL QAEDEADYYC SSYTSSSTRV FGTGTKVTVL GQPKANPTVT  120
LFPPSSEELQ ANKATLVCLI SDFYPGAVTV AWKADGSPVK AGVETTKPSK QSNNKYAASS  180
YLSLTPEQWK SHRSYSCQVT HEGSTVEKTV APTECS                             216

SEQ ID NO: 17             moltype = AA  length = 450
FEATURE                   Location/Qualifiers
REGION                    1..450
                          note = Synthetic Construct
source                    1..450
                          mol_type = protein
                          organism = synthetic construct
SEQUENCE: 17
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
```

-continued

```
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPASIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG                                  450

SEQ ID NO: 18          moltype = AA  length = 215
FEATURE                Location/Qualifiers
REGION                 1..215
                       note = Synthetic Construct
source                 1..215
                       mol_type = protein
                       organism = synthetic construct
SEQUENCE: 18
EIVLTQSPGT LSLSPGERAT LSCRASQRVS SSYLAWYQQK PGQAPRLLIY DASSRATGIP  60
DRFSGSGSGT DFTLTISRLE PEDFAVYYCQ QYGSLPWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215

SEQ ID NO: 19          moltype = AA  length = 447
FEATURE                Location/Qualifiers
REGION                 1..447
                       note = Synthetic Construct
source                 1..447
                       mol_type = protein
                       organism = synthetic construct
SEQUENCE: 19
QVQLVQSGSE LKKPGASVKI SCKASGYTFT NYGMNWVRQA PGQGLQWMGW INTDSGESTY  60
AEEFKGRFVF SLDTSVNTAY LQITSLTAED TGMYFCVRVG YDALDYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKRVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSREEMTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 20          moltype = AA  length = 213
FEATURE                Location/Qualifiers
REGION                 1..213
                       note = Synthetic Construct
source                 1..213
                       mol_type = protein
                       organism = synthetic construct
SEQUENCE: 20
EIVLTQSPSS LSASVGDRVT ITCSARSSVS YMHWFQQKPG KAPKLWIYRT SNLASGVPSR  60
FSGSGSGTSY CLTINSLQPE DFATYYCQQR SSFPLTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213
```